US012635867B2

(12) United States Patent
Li et al.

(10) Patent No.: US 12,635,867 B2
(45) Date of Patent: May 26, 2026

(54) IMAGE QUALITY ASSESSMENT AND MULTI MODE DYNAMIC CAMERA FOR DENTAL IMAGES

(71) Applicant: ALIGN TECHNOLOGY, INC., San Jose, CA (US)

(72) Inventors: Guotu Li, Apex, NC (US); Chao Shi, Morrisville, NC (US); Chad Clayton Brown, Cary, NC (US); Christopher E. Cramer, Durham, NC (US); Phillip Thomas Harris, Cary, NC (US); Adam Sill, Raleigh, NC (US); Will Neville, Bluffton, SC (US); Ritvik Bansal, San Francisco, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 224 days.

(21) Appl. No.: 18/487,942

(22) Filed: Oct. 16, 2023

(65) Prior Publication Data

US 2024/0122463 A1      Apr. 18, 2024

Related U.S. Application Data

(60) Provisional application No. 63/384,525, filed on Nov. 21, 2022, provisional application No. 63/416,930, filed on Oct. 17, 2022.

(51) Int. Cl.
*G16H 40/63*      (2018.01)
*A61B 1/00*       (2006.01)
(Continued)

(52) U.S. Cl.
CPC ............ *A61B 1/24* (2013.01); *A61B 1/00006* (2013.01); *A61B 1/000096* (2022.02); *A61B 1/045* (2013.01); *A61B 1/32* (2013.01); *G06T 7/0012* (2013.01); *G06T 7/11* (2017.01); *G06V 20/50* (2022.01); *G06V 40/166* (2022.01);
(Continued)

(58) Field of Classification Search
CPC . A61B 1/24; A61B 1/00006; A61B 1/000096; A61B 1/045; A61B 1/32; A61B 1/00172; A61B 1/00194; G06T 7/0012; G06T 7/11; G06T 2207/20084; G06T 2207/20132; G06T 2207/30036; G06T 2207/30168; G06V 20/50; G06V 40/166; G06V 40/171; G06V 2201/034; G06V 10/44; G06V 10/764; G06V 10/774; G06V 10/82; G06V 10/993; G06V 20/60; G06V 40/161; G06V 2201/03; H04N 23/611; H04N 23/64; H04N 23/667; G16H 30/20
See application file for complete search history.

(56) References Cited

U.S. PATENT DOCUMENTS

| | | | |
|---|---|---|---|
| 5,975,893 | A | 11/1999 | Chishti et al. |
| 6,227,850 | B1 | 5/2001 | Chishti et al. |

(Continued)

*Primary Examiner* — Howard D Brown, Jr.
(74) *Attorney, Agent, or Firm* — FisherBroyles, LLP

(57) ABSTRACT

Various apparatuses are disclosed (e.g., system, device, method, or the like) for guiding the capture and assessing the quality of an image, including dental images. The apparatuses may use trained neural networks to examine images and provide users feedback regarding image quality. The neural networks may be trained based on images within image groups that have been ranked based on perceived image quality.

25 Claims, 39 Drawing Sheets

(51) Int. Cl.

| | |
|---|---|
| *A61B 1/045* | (2006.01) |
| *A61B 1/24* | (2006.01) |
| *A61B 1/32* | (2006.01) |
| *G06T 7/00* | (2017.01) |
| *G06T 7/11* | (2017.01) |
| *G06V 20/50* | (2022.01) |
| *G06V 40/16* | (2022.01) |
| *H04N 23/60* | (2023.01) |
| *H04N 23/611* | (2023.01) |
| *H04N 23/667* | (2023.01) |

(52) U.S. Cl.
CPC ......... *G06V 40/171* (2022.01); *H04N 23/611* (2023.01); *H04N 23/64* (2023.01); *H04N 23/667* (2023.01); *G06T 2207/20084* (2013.01); *G06T 2207/20132* (2013.01); *G06T 2207/30036* (2013.01); *G06T 2207/30168* (2013.01); *G06V 2201/034* (2022.01)

(56) References Cited

U.S. PATENT DOCUMENTS

| | | | |
|---|---|---|---|
| 6,227,851 | B1 | 5/2001 | Chishti et al. |
| 6,299,440 | B1 | 10/2001 | Phan et al. |
| 6,318,994 | B1 | 11/2001 | Chishti et al. |
| 6,371,761 | B1 | 4/2002 | Cheang et al. |
| 6,386,878 | B1 | 5/2002 | Pavlovskaia et al. |
| 6,406,292 | B1 | 6/2002 | Chishti et al. |
| 6,409,504 | B1 | 6/2002 | Jones et al. |
| 6,457,972 | B1 | 10/2002 | Chishti et al. |
| 6,488,499 | B1 | 12/2002 | Miller |
| 6,514,074 | B1 | 2/2003 | Chishti et al. |
| 6,554,611 | B2 | 4/2003 | Chishti et al. |
| 6,582,229 | B1 | 6/2003 | Miller et al. |
| 6,602,070 | B2 | 8/2003 | Miller et al. |
| 6,621,491 | B1 | 9/2003 | Baumrind et al. |
| 6,688,886 | B2 | 2/2004 | Hughes et al. |
| 6,726,478 | B1 | 4/2004 | Isiderio et al. |
| 6,729,876 | B2 | 5/2004 | Chishti et al. |
| 6,739,869 | B1 | 5/2004 | Taub et al. |
| 6,767,208 | B2 | 7/2004 | Kaza |
| 6,783,360 | B2 | 8/2004 | Chishti |
| 7,040,896 | B2 | 5/2006 | Pavlovskaia et al. |
| 7,063,532 | B1 | 6/2006 | Jones et al. |
| 7,074,038 | B1 | 7/2006 | Miller |
| 7,074,039 | B2 | 7/2006 | Kopelman et al. |
| 7,077,647 | B2 | 7/2006 | Choi et al. |
| 7,108,508 | B2 | 9/2006 | Hedge et al. |
| 7,134,874 | B2 | 11/2006 | Chishti et al. |
| 7,156,661 | B2 | 1/2007 | Choi et al. |
| 7,160,107 | B2 | 1/2007 | Kopelman et al. |
| 7,241,142 | B2 | 7/2007 | Abolfathi et al. |
| 7,293,988 | B2 | 11/2007 | Wen |
| 7,309,230 | B2 | 12/2007 | Wen |
| 7,357,634 | B2 | 4/2008 | Knopp |
| 7,555,403 | B2 | 6/2009 | Kopelman et al. |
| 7,637,740 | B2 | 12/2009 | Knopp |
| 7,689,398 | B2 | 3/2010 | Cheng et al. |
| 7,736,147 | B2 | 6/2010 | Kaza et al. |
| 7,746,339 | B2 | 6/2010 | Matov et al. |
| 7,844,356 | B2 | 11/2010 | Matov et al. |
| 7,844,429 | B2 | 11/2010 | Matov et al. |
| 7,865,259 | B2 | 1/2011 | Kuo et al. |
| 7,878,804 | B2 | 2/2011 | Korytov et al. |
| 7,880,751 | B2 | 2/2011 | Kuo et al. |
| 7,904,308 | B2 | 3/2011 | Arnone et al. |
| 7,930,189 | B2 | 4/2011 | Kuo |
| 7,942,672 | B2 | 5/2011 | Kuo |
| 7,970,627 | B2 | 6/2011 | Kuo et al. |
| 7,970,628 | B2 | 6/2011 | Kuo et al. |
| 8,038,444 | B2 | 10/2011 | Kitching et al. |
| 8,044,954 | B2 | 10/2011 | Kitching et al. |
| 8,075,306 | B2 | 12/2011 | Kitching et al. |
| 8,092,215 | B2 | 1/2012 | Stone-Collonge et al. |
| 8,099,268 | B2 | 1/2012 | Kitching et al. |
| 8,108,189 | B2 | 1/2012 | Chelnokov et al. |
| 8,126,726 | B2 | 2/2012 | Matov et al. |
| 8,260,591 | B2 | 9/2012 | Kass et al. |
| 8,275,180 | B2 | 9/2012 | Kuo |
| 8,401,826 | B2 | 3/2013 | Cheng et al. |
| 8,439,672 | B2 | 5/2013 | Matov et al. |
| 8,562,338 | B2 | 10/2013 | Kitching et al. |
| 8,591,225 | B2 | 11/2013 | Wu et al. |
| 8,788,285 | B2 | 7/2014 | Kuo |
| 8,843,381 | B2 | 9/2014 | Kuo et al. |
| 8,874,452 | B2 | 10/2014 | Kuo |
| 8,896,592 | B2 | 11/2014 | Boltunov et al. |
| 8,930,219 | B2 | 1/2015 | Trosien et al. |
| 9,037,439 | B2 | 5/2015 | Kuo et al. |
| 9,060,829 | B2 | 6/2015 | Sterental et al. |
| 9,125,709 | B2 | 9/2015 | Matty |
| 9,211,166 | B2 | 12/2015 | Kuo et al. |
| 9,220,580 | B2 | 12/2015 | Borovinskih et al. |
| 9,364,296 | B2 | 6/2016 | Kuo |
| 9,375,300 | B2 | 6/2016 | Matov et al. |
| 9,414,897 | B2 | 8/2016 | Wu et al. |
| 9,492,245 | B2 | 11/2016 | Sherwood et al. |
| 9,642,678 | B2 | 5/2017 | Kuo |
| 10,248,883 | B2 | 4/2019 | Borovinskih et al. |
| 10,342,638 | B2 | 7/2019 | Kitching et al. |
| 10,463,452 | B2 | 11/2019 | Matov et al. |
| 10,595,966 | B2 | 3/2020 | Carrier, Jr. et al. |
| 10,617,489 | B2 | 4/2020 | Grove et al. |
| 10,722,328 | B2 | 7/2020 | Velazquez et al. |
| 10,758,322 | B2 | 9/2020 | Pokotilov et al. |
| 10,779,718 | B2 | 9/2020 | Meyer et al. |
| 10,792,127 | B2 | 10/2020 | Kopelman et al. |
| 10,798,339 | B2 * | 10/2020 | McMillan .............. A61B 90/37 |
| 10,828,130 | B2 | 11/2020 | Pokotilov et al. |
| 10,835,349 | B2 | 11/2020 | Cramer et al. |
| 10,943,407 | B1 * | 3/2021 | Morgan ................. G16H 15/00 |
| 10,973,611 | B2 | 4/2021 | Pokotilov et al. |
| 10,996,813 | B2 | 5/2021 | Makarenkova et al. |
| 10,997,727 | B2 | 5/2021 | Xue et al. |
| 11,020,205 | B2 | 6/2021 | Li et al. |
| 11,020,206 | B2 | 6/2021 | Shi et al. |
| 11,026,766 | B2 | 6/2021 | Chekh et al. |
| 11,033,359 | B2 | 6/2021 | Velazquez et al. |
| 11,071,608 | B2 | 7/2021 | Derakhshan et al. |
| 11,096,763 | B2 | 8/2021 | Akopov et al. |
| 11,116,605 | B2 | 9/2021 | Nyukhtikov et al. |
| 11,147,652 | B2 | 10/2021 | Mason et al. |
| 11,151,753 | B2 | 10/2021 | Gao et al. |
| 11,154,381 | B2 | 10/2021 | Roschin et al. |
| 11,259,896 | B2 | 3/2022 | Matov et al. |
| 11,357,598 | B2 | 6/2022 | Cramer |
| 11,395,717 | B2 | 7/2022 | Yuryev et al. |
| 11,432,908 | B2 | 9/2022 | Kopelman et al. |
| 11,464,604 | B2 | 10/2022 | Makarenkova et al. |
| 11,478,334 | B2 | 10/2022 | Matov et al. |
| 11,484,389 | B2 | 11/2022 | Sterental et al. |
| 11,521,732 | B2 | 12/2022 | Levin et al. |
| 11,534,272 | B2 | 12/2022 | Li et al. |
| 11,553,988 | B2 | 1/2023 | Mednikov et al. |
| 11,633,268 | B2 | 4/2023 | Moalem et al. |
| 11,642,195 | B2 | 5/2023 | Gao et al. |
| 11,651,494 | B2 | 5/2023 | Brown et al. |
| 11,654,001 | B2 | 5/2023 | Roschin et al. |
| 11,707,344 | B2 | 7/2023 | Roschin et al. |
| 11,810,271 | B2 | 11/2023 | Shi et al. |
| 2003/0008259 | A1 | 1/2003 | Kuo et al. |
| 2003/0143509 | A1 | 7/2003 | Kopelman et al. |
| 2003/0207227 | A1 | 11/2003 | Abolfathi |
| 2004/0137400 | A1 | 7/2004 | Chishti et al. |
| 2004/0152036 | A1 | 8/2004 | Abolfathi |
| 2004/0197728 | A1 | 10/2004 | Abolfathi et al. |
| 2004/0259049 | A1 | 12/2004 | Kopelman et al. |
| 2005/0182654 | A1 | 8/2005 | Abolfathi et al. |
| 2005/0244791 | A1 | 11/2005 | Davis et al. |
| 2006/0127836 | A1 | 6/2006 | Wen |
| 2006/0127852 | A1 | 6/2006 | Wen |
| 2006/0127854 | A1 | 6/2006 | Wen |
| 2006/0275731 | A1 | 12/2006 | Wen et al. |

(56) References Cited

U.S. PATENT DOCUMENTS

| | | | |
|---|---|---|---|
| 2006/0275736 A1 | 12/2006 | Wen et al. | |
| 2008/0306724 A1 | 12/2008 | Kitching et al. | |
| 2010/0009308 A1 | 1/2010 | Wen et al. | |
| 2010/0063845 A1* | 3/2010 | Yeluri | G16H 10/60 |
| | | | 705/2 |
| 2010/0068672 A1 | 3/2010 | Arjomand et al. | |
| 2010/0068676 A1 | 3/2010 | Mason et al. | |
| 2010/0092907 A1 | 4/2010 | Knopp | |
| 2010/0167243 A1 | 7/2010 | Spiridonov et al. | |
| 2013/0204599 A1 | 8/2013 | Matov et al. | |
| 2015/0320320 A1* | 11/2015 | Kopelman | A61B 5/0088 |
| | | | 433/215 |
| 2016/0310235 A1 | 10/2016 | Derakhshan et al. | |
| 2017/0273760 A1 | 9/2017 | Morton et al. | |
| 2018/0280118 A1 | 10/2018 | Cramer | |
| 2019/0328234 A1* | 10/2019 | Seibel | A61B 5/14539 |
| 2019/0328487 A1 | 10/2019 | Levin et al. | |
| 2019/0328488 A1 | 10/2019 | Levin et al. | |
| 2020/0155274 A1 | 5/2020 | Pimenov et al. | |
| 2020/0297458 A1 | 9/2020 | Roschin et al. | |
| 2020/0306011 A1 | 10/2020 | Chekhonin et al. | |
| 2021/0134436 A1 | 5/2021 | Meyer et al. | |
| 2021/0279871 A1* | 9/2021 | Johnson | G06T 7/12 |
| 2022/0130532 A1* | 4/2022 | Lemchen | A61C 7/16 |
| 2022/0165388 A1 | 5/2022 | Chernov et al. | |
| 2022/0238194 A1* | 7/2022 | Ruetschi | G16H 80/00 |
| 2022/0338802 A1* | 10/2022 | Gassman | A61B 5/6802 |
| 2022/0384032 A1* | 12/2022 | Sandor | A61B 5/7475 |
| 2023/0009652 A1* | 1/2023 | Wood | G06T 17/00 |
| 2023/0072470 A1* | 3/2023 | Miller | H04N 23/611 |
| 2023/0386045 A1* | 11/2023 | Amelon | A61B 5/4547 |
| 2024/0122463 A1* | 4/2024 | Li | H04N 23/667 |

* cited by examiner

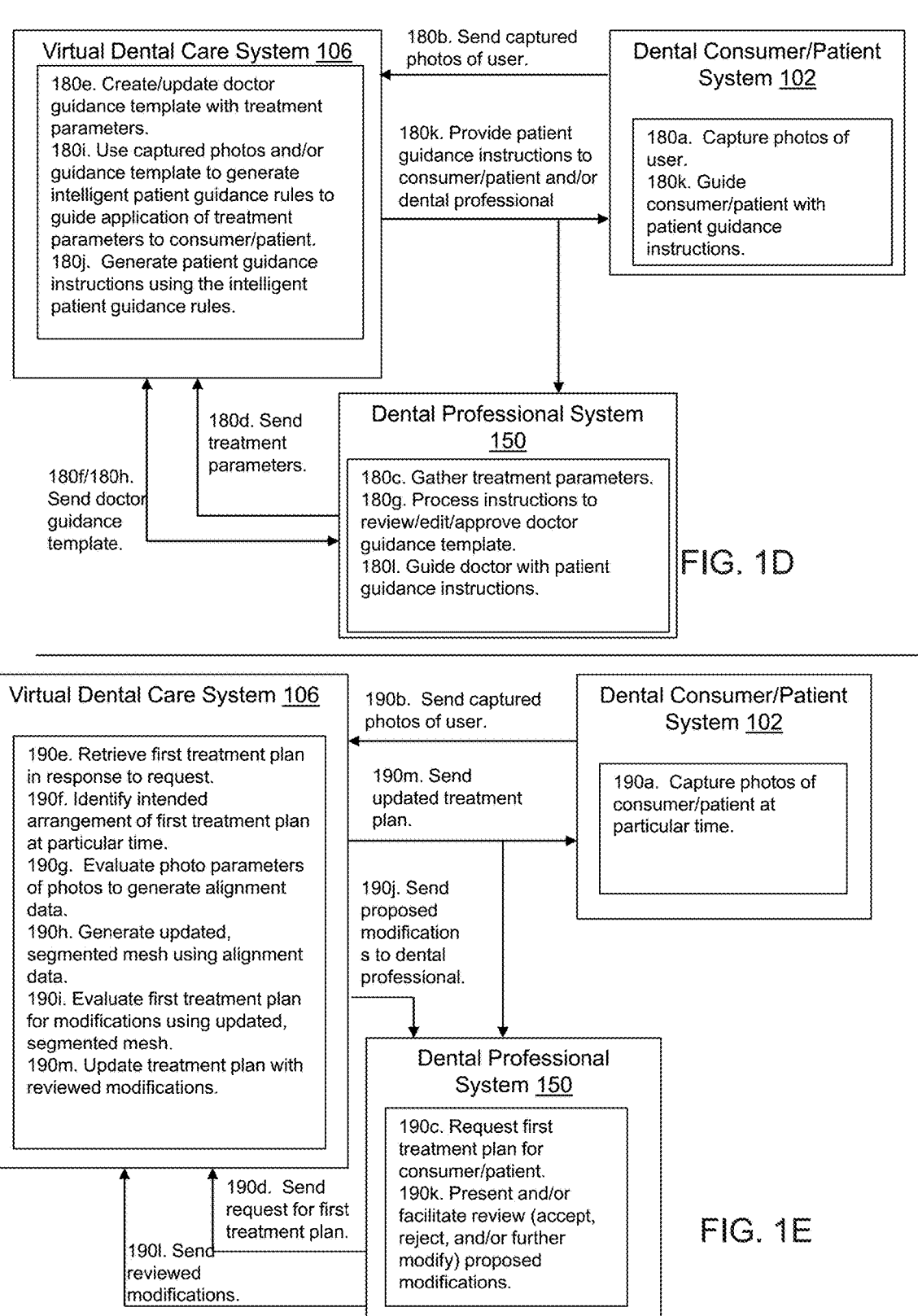

Virtual Dental Care System 106

180e. Create/update doctor guidance template with treatment parameters.
180i. Use captured photos and/or guidance template to generate intelligent patient guidance rules to guide application of treatment parameters to consumer/patient.
180j. Generate patient guidance instructions using the intelligent patient guidance rules.

180b. Send captured photos of user.

180k. Provide patient guidance instructions to consumer/patient and/or dental professional

Dental Consumer/Patient System 102

180a. Capture photos of user.
180k. Guide consumer/patient with patient guidance instructions.

180d. Send treatment parameters.

180f/180h. Send doctor guidance template.

Dental Professional System 150

180c. Gather treatment parameters.
180g. Process instructions to review/edit/approve doctor guidance template.
180l. Guide doctor with patient guidance instructions.

FIG. 1D

Virtual Dental Care System 106

190e. Retrieve first treatment plan in response to request.
190f. Identify intended arrangement of first treatment plan at particular time.
190g. Evaluate photo parameters of photos to generate alignment data.
190h. Generate updated, segmented mesh using alignment data.
190i. Evaluate first treatment plan for modifications using updated, segmented mesh.
190m. Update treatment plan with reviewed modifications.

190b. Send captured photos of user.

190m. Send updated treatment plan.

190j. Send proposed modifications to dental professional.

Dental Consumer/Patient System 102

190a. Capture photos of consumer/patient at particular time.

190d. Send request for first treatment plan.

190l. Send reviewed modifications.

Dental Professional System 150

190c. Request first treatment plan for consumer/patient.
190k. Present and/or facilitate review (accept, reject, and/or further modify) proposed modifications.

FIG. 1E

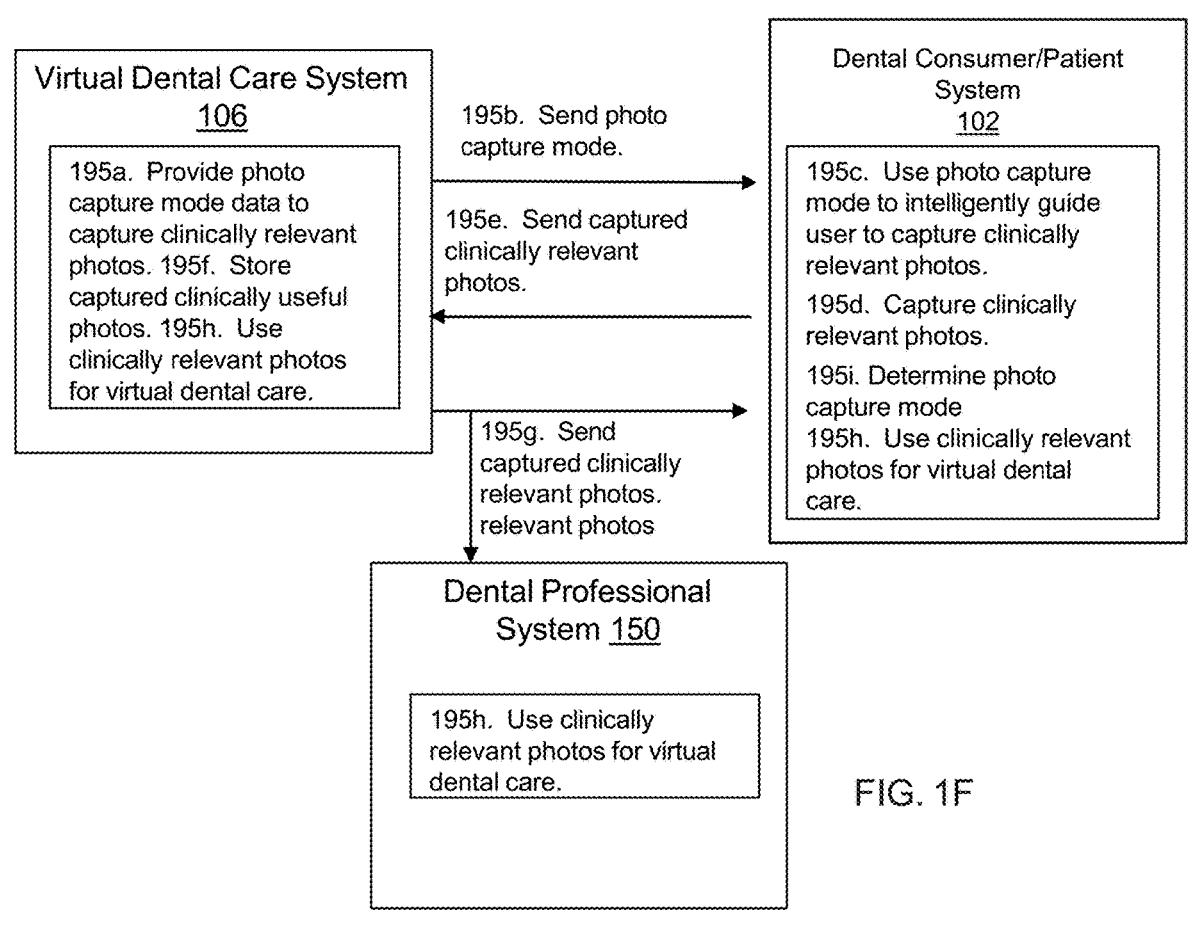

Virtual Dental Care System
106

195a.  Provide photo capture mode data to capture clinically relevant photos. 195f.  Store captured clinically useful photos. 195h.  Use clinically relevant photos for virtual dental care.

195b.  Send photo capture mode.

195e.  Send captured clinically relevant photos.

195g.  Send captured clinically relevant photos. relevant photos

Dental Consumer/Patient System
102

195c.  Use photo capture mode to intelligently guide user to capture clinically relevant photos.

195d.  Capture clinically relevant photos.

195i. Determine photo capture mode

195h.  Use clinically relevant photos for virtual dental care.

Dental Professional System 150

195h.  Use clinically relevant photos for virtual dental care.

FIG. 1F

300
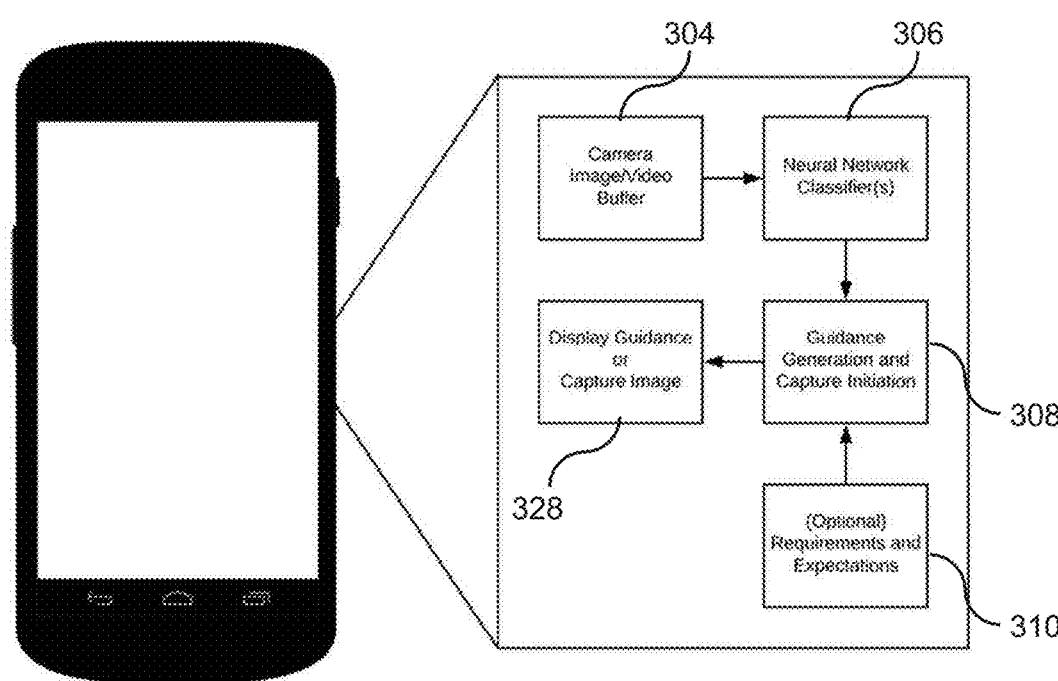
FIG. 3

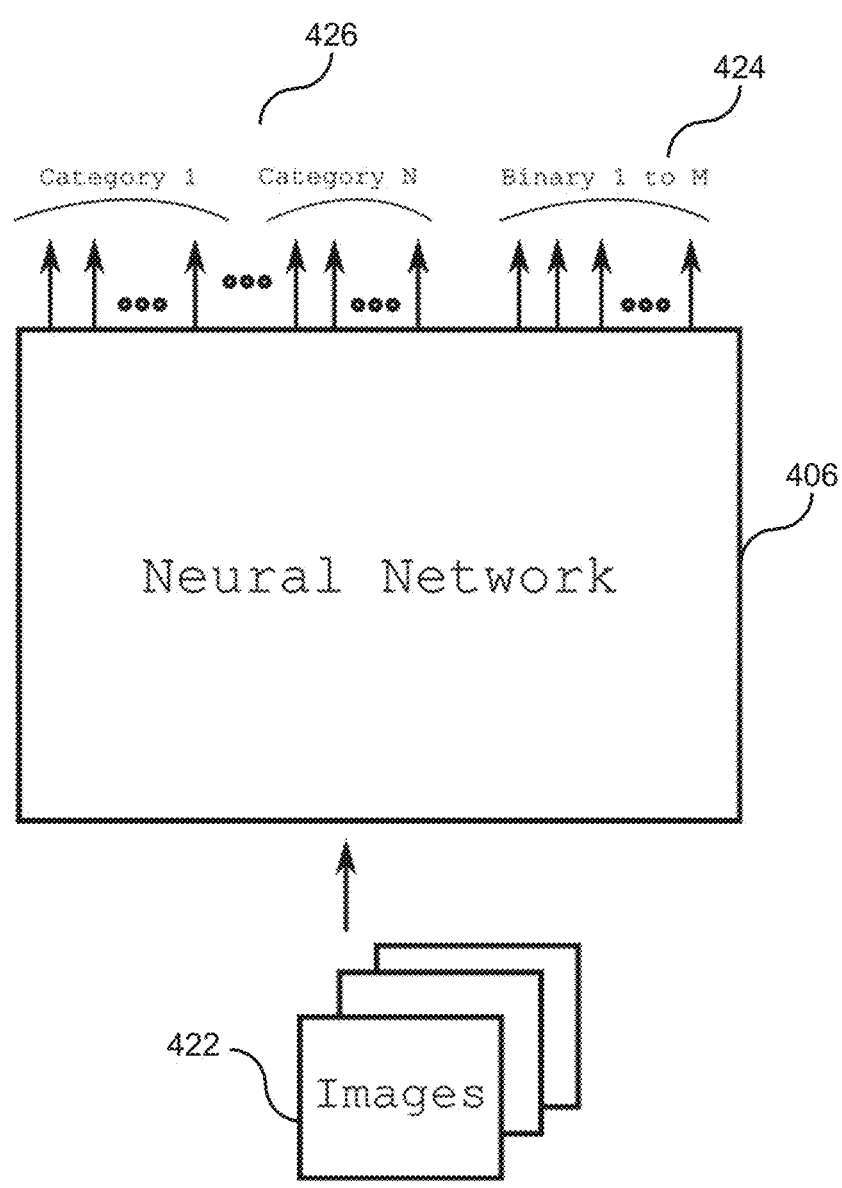
FIG. 4

500

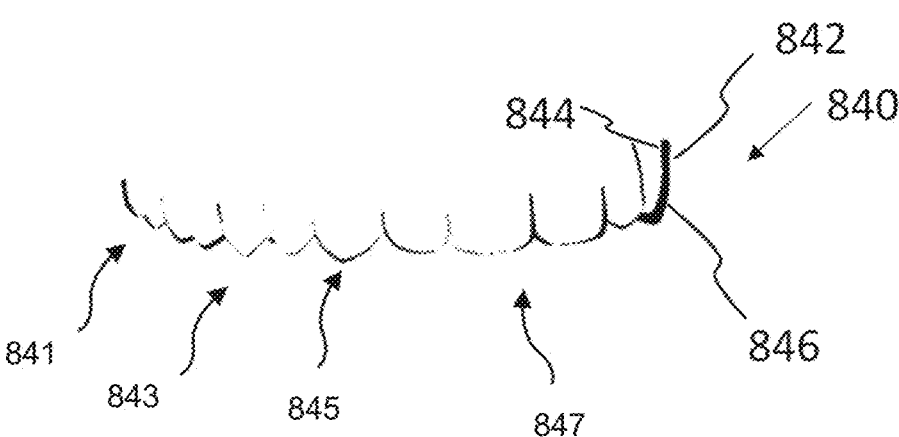
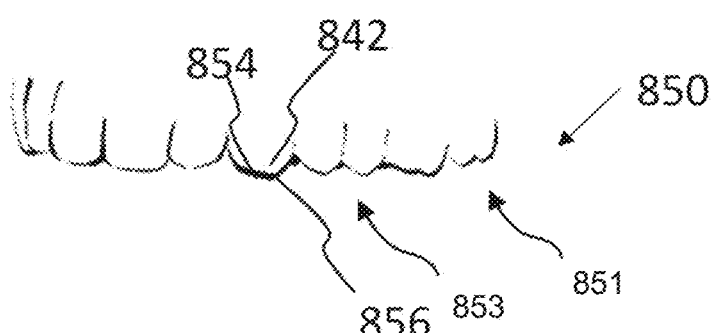
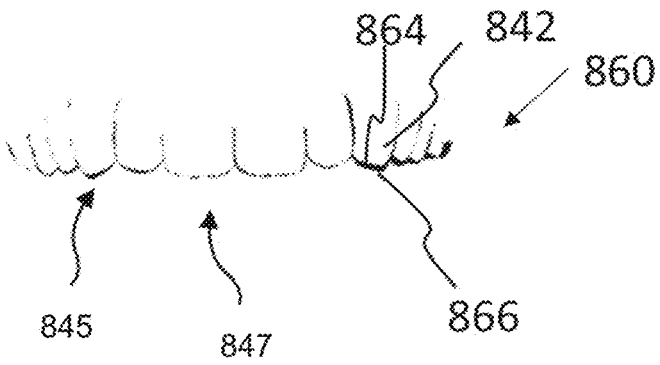
FIG. 8

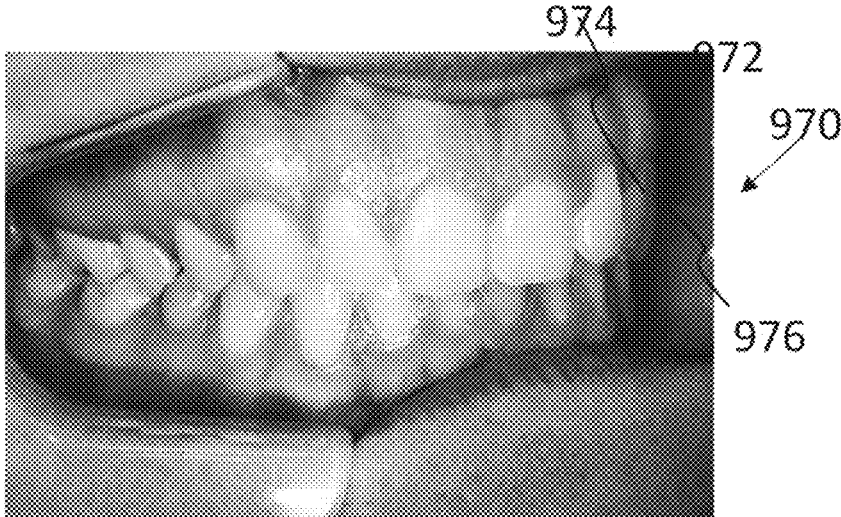
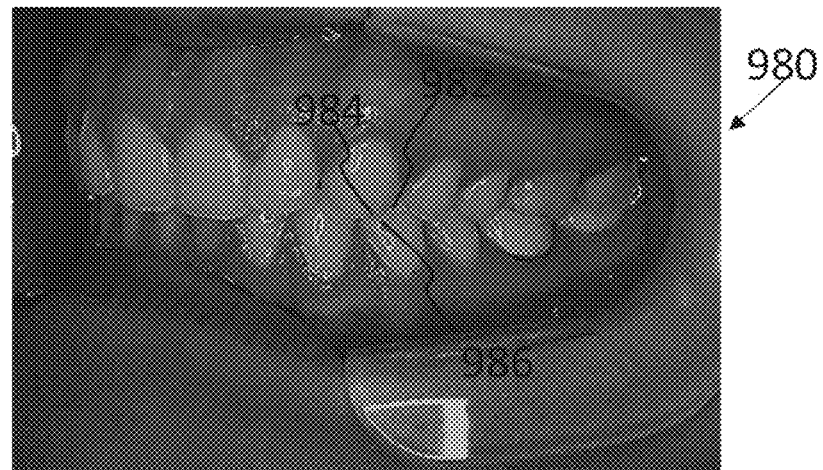
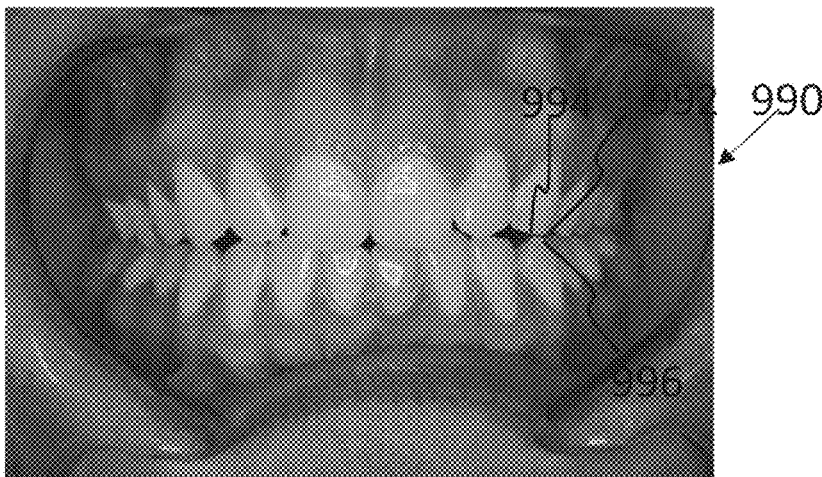
FIG. 9

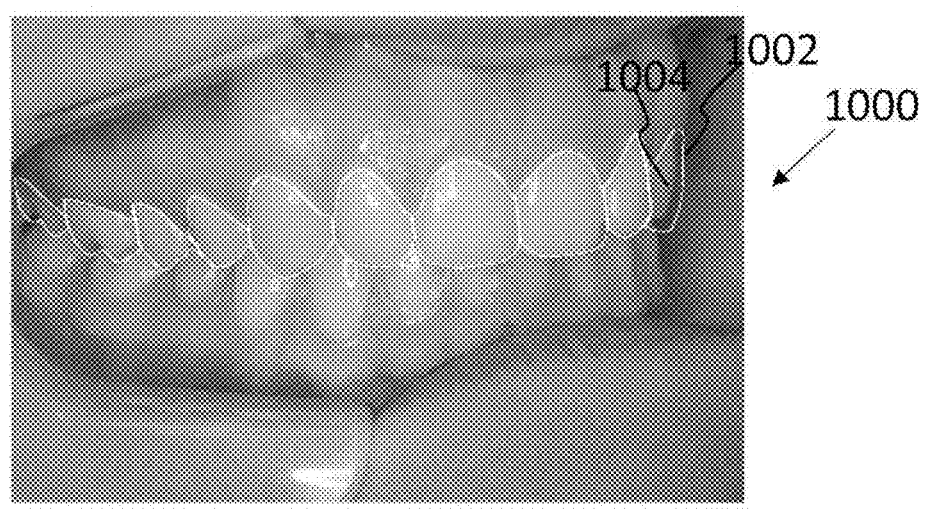
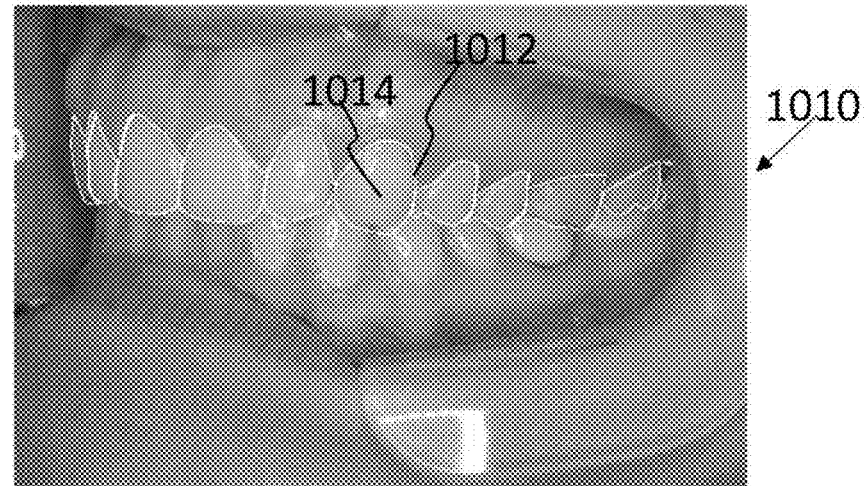
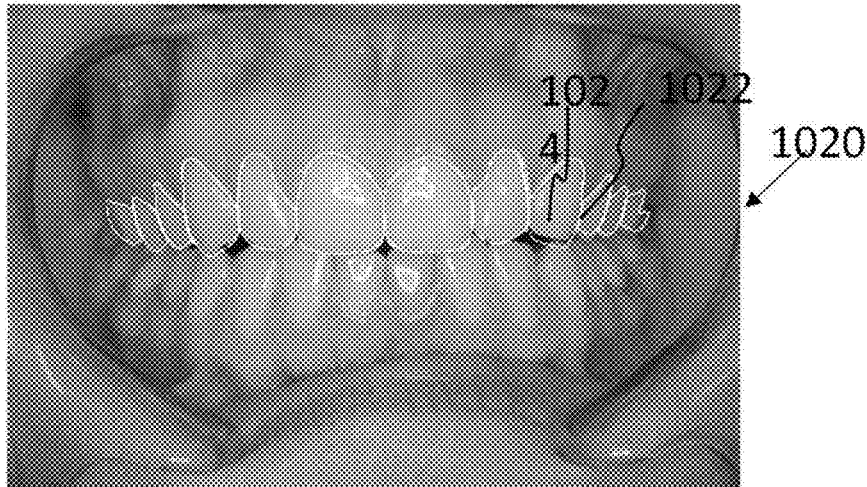
FIG. 10

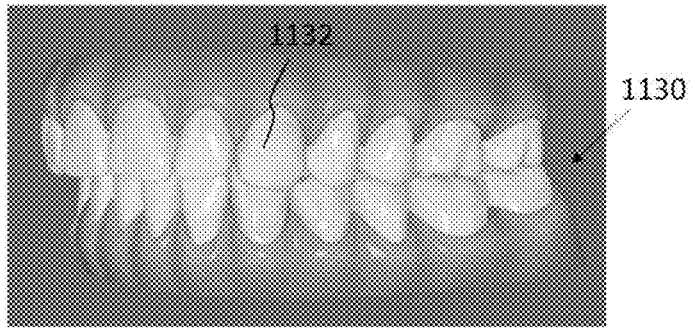
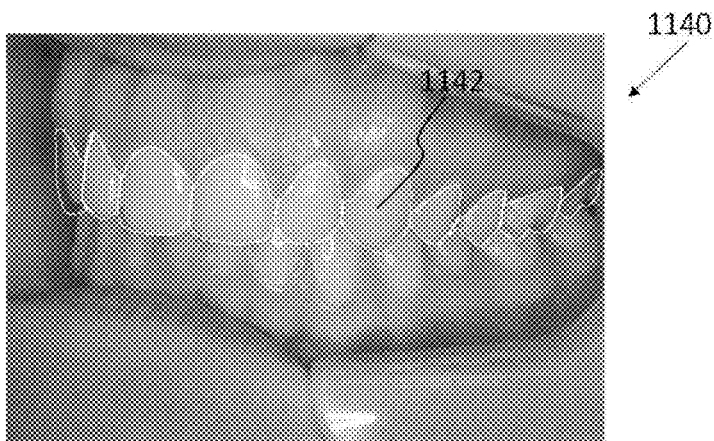
FIG. 11

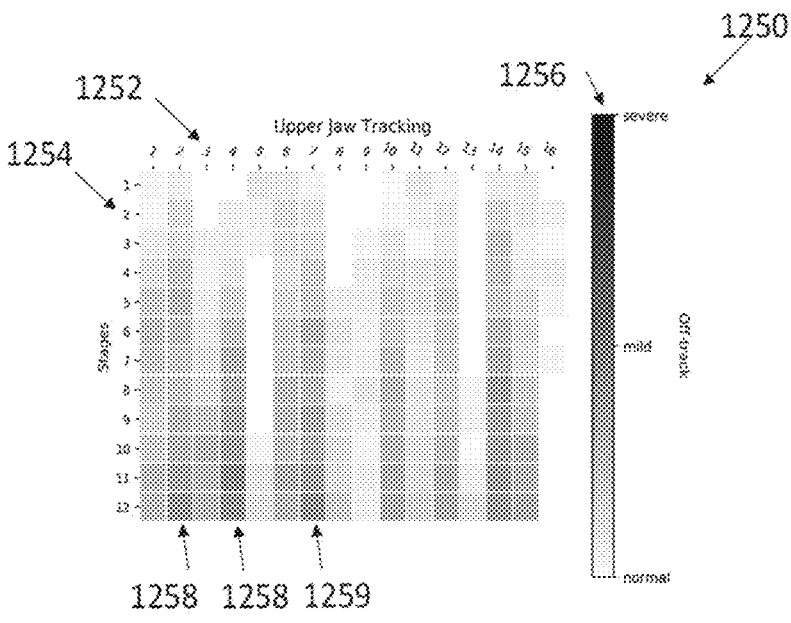
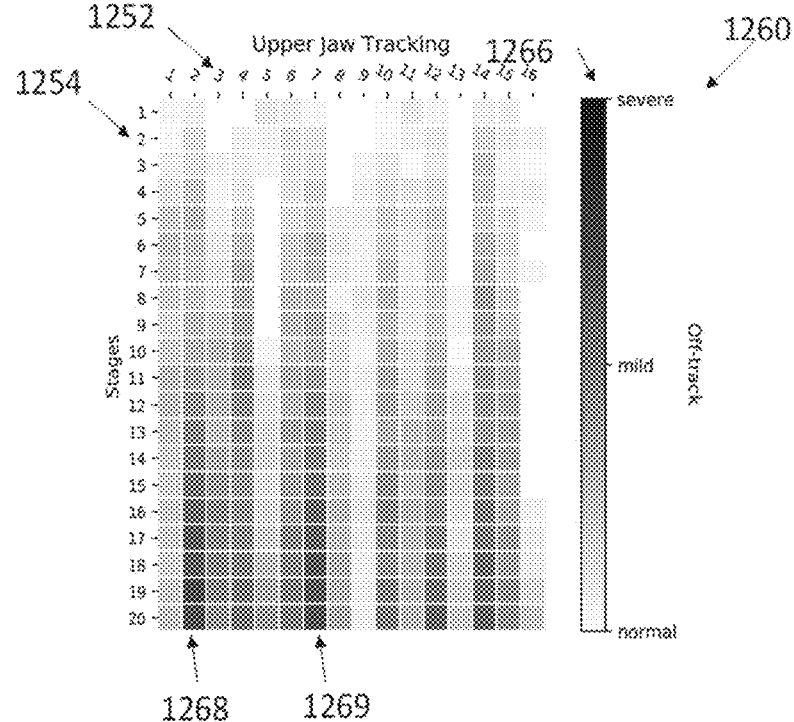
FIG. 12

1400

1700

1810
1802
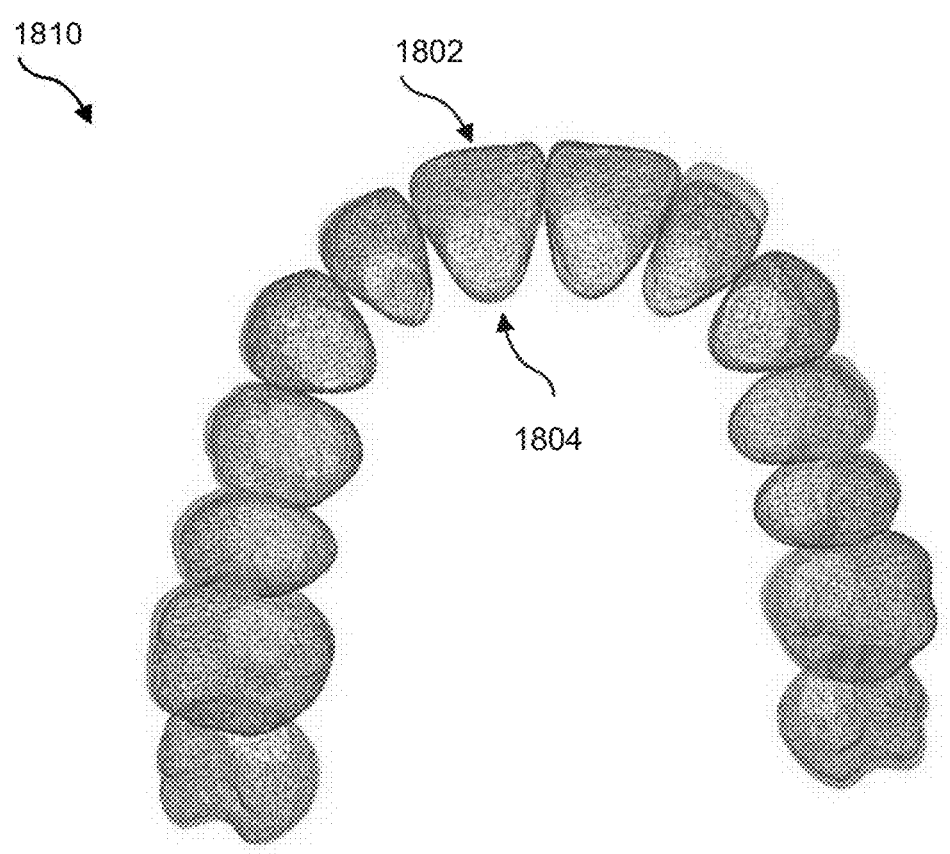
1804
1806
1820
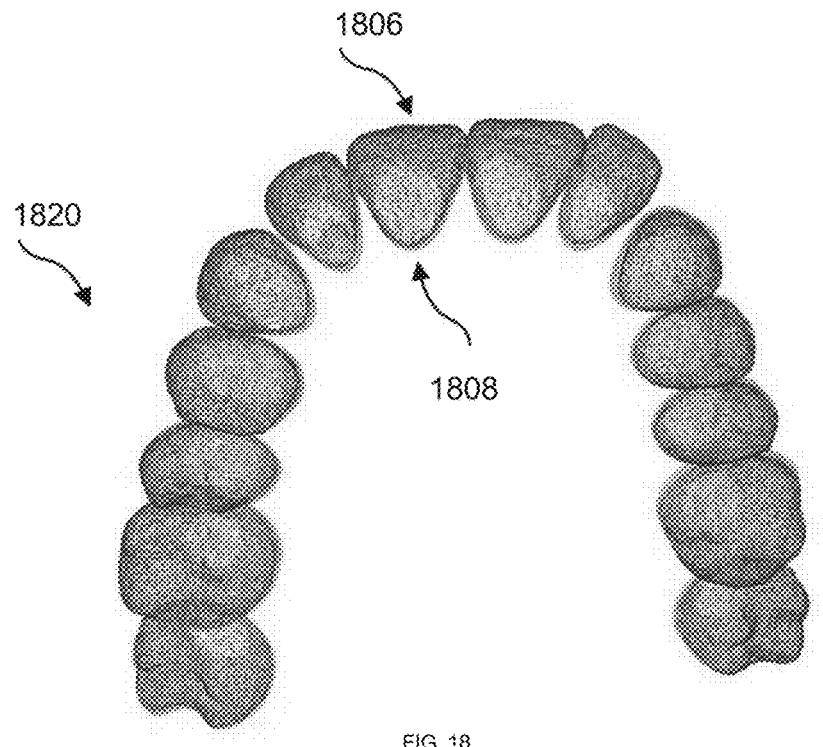
1808
FIG. 18

Network Architecture
2000

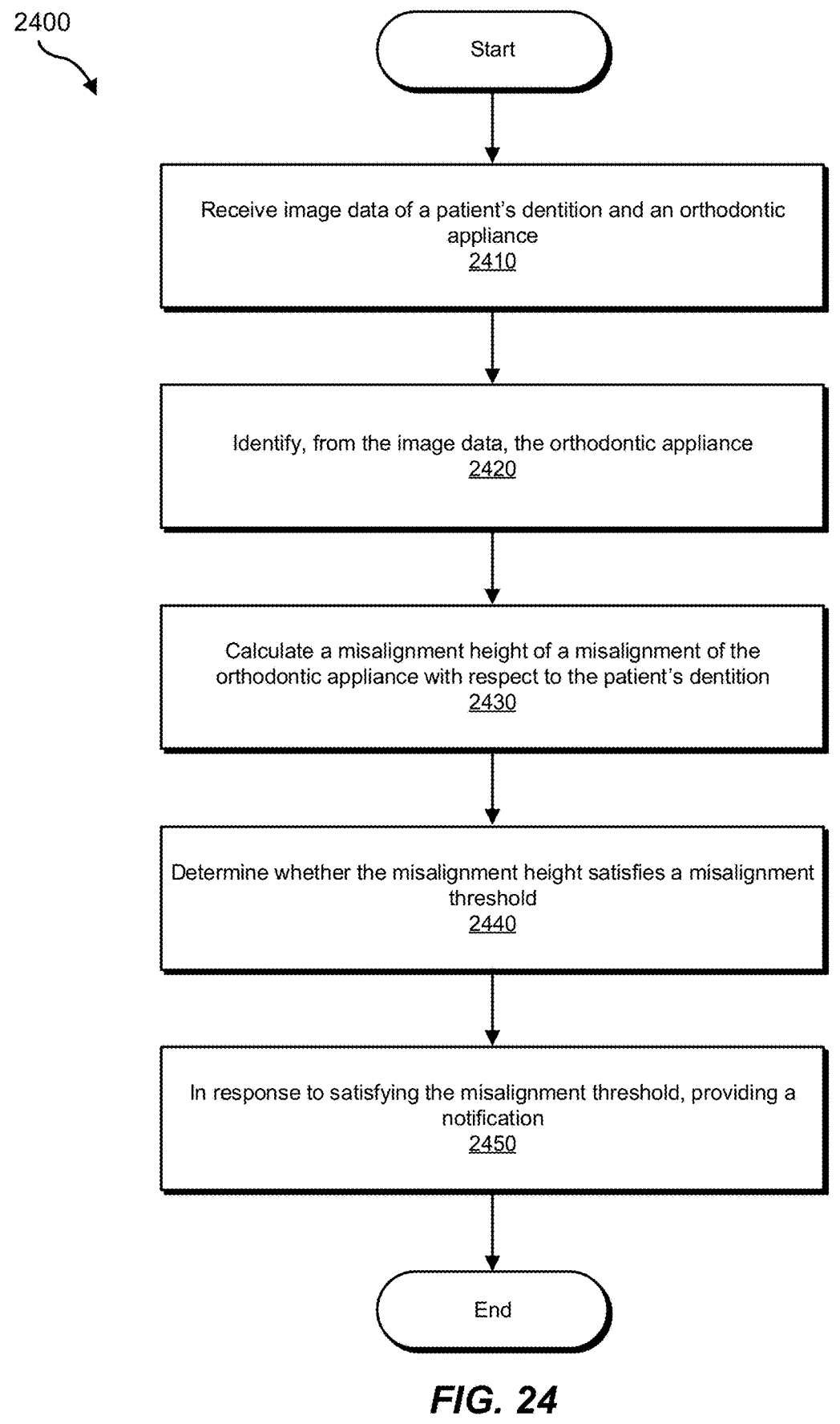

2400

Start

Receive image data of a patient's dentition and an orthodontic appliance
2410

Identify, from the image data, the orthodontic appliance
2420

Calculate a misalignment height of a misalignment of the orthodontic appliance with respect to the patient's dentition
2430

Determine whether the misalignment height satisfies a misalignment threshold
2440

In response to satisfying the misalignment threshold, providing a notification
2450

End

*FIG. 24*

2500
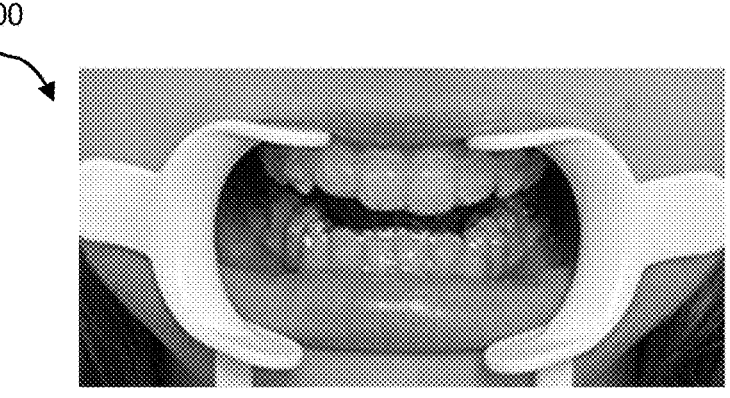
*FIG. 25A*
2502
2510
2530
2520
*FIG. 25B*
2504
2510
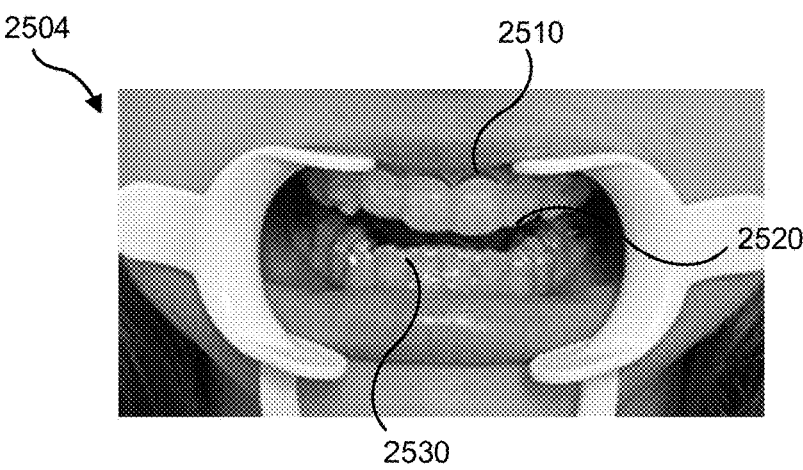
2520
2530
*FIG. 25C*

2600
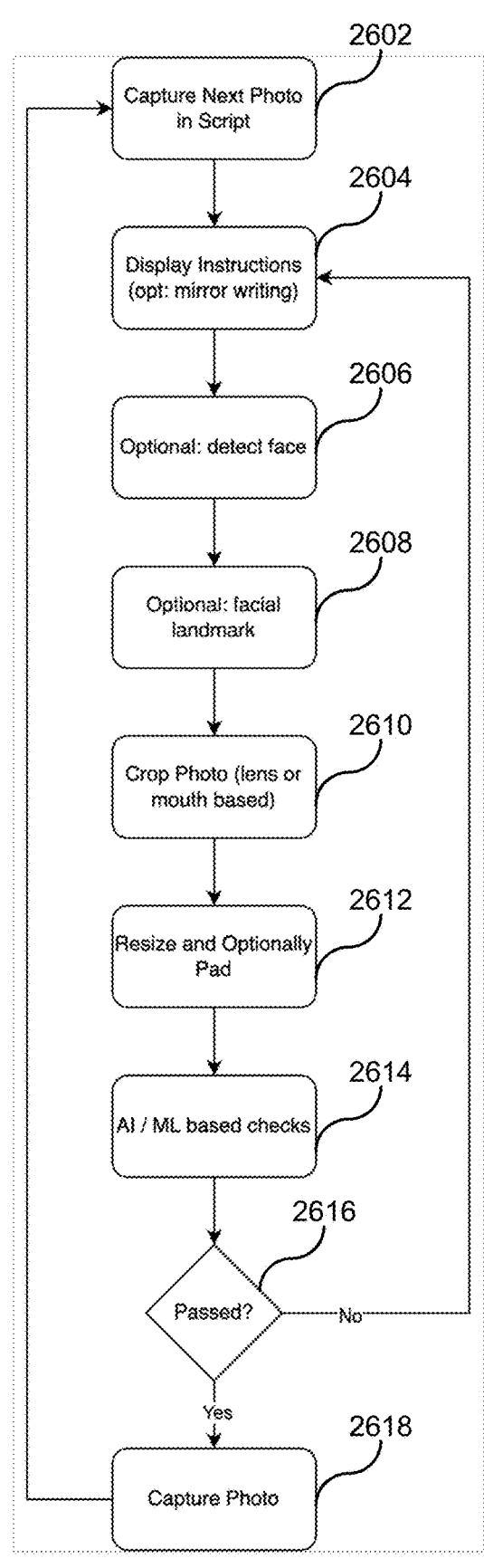
2602
Capture Next Photo in Script
2604
Display Instructions (opt: mirror writing)
2606
Optional: detect face
2608
Optional: facial landmark
2610
Crop Photo (lens or mouth based)
2612
Resize and Optionally Pad
2614
AI / ML based checks
2616
Passed?    No
Yes
2618
Capture Photo
*FIG. 26*

2700
2702
2704
2708
2706
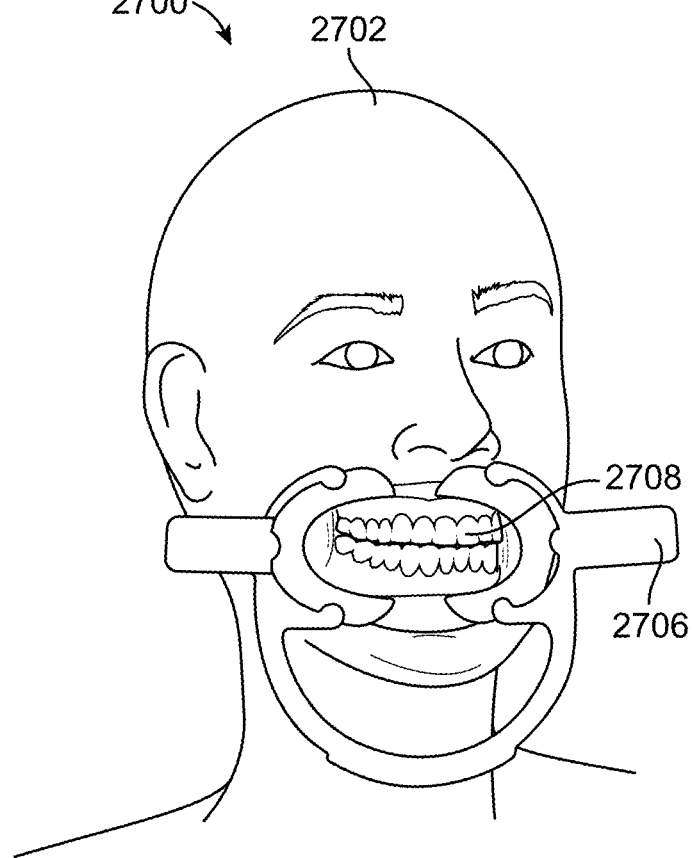
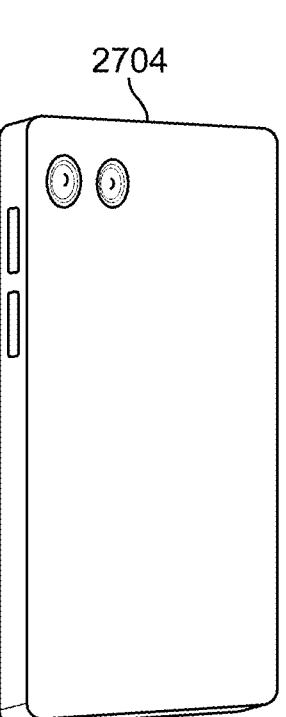
FIG. 27

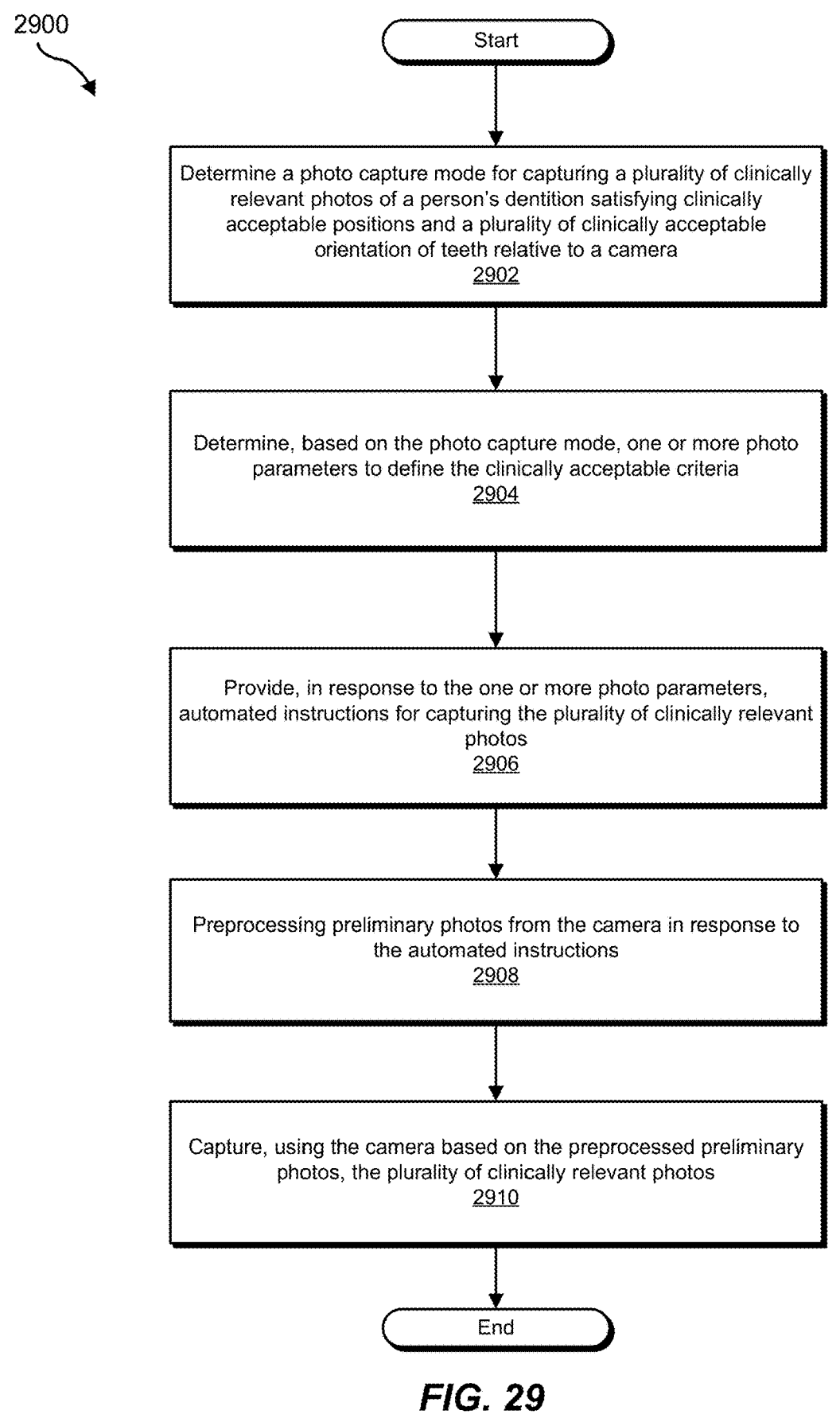

2900

Start

Determine a photo capture mode for capturing a plurality of clinically relevant photos of a person's dentition satisfying clinically acceptable positions and a plurality of clinically acceptable orientation of teeth relative to a camera
2902

Determine, based on the photo capture mode, one or more photo parameters to define the clinically acceptable criteria
2904

Provide, in response to the one or more photo parameters, automated instructions for capturing the plurality of clinically relevant photos
2906

Preprocessing preliminary photos from the camera in response to the automated instructions
2908

Capture, using the camera based on the preprocessed preliminary photos, the plurality of clinically relevant photos
2910

End

*FIG. 29*

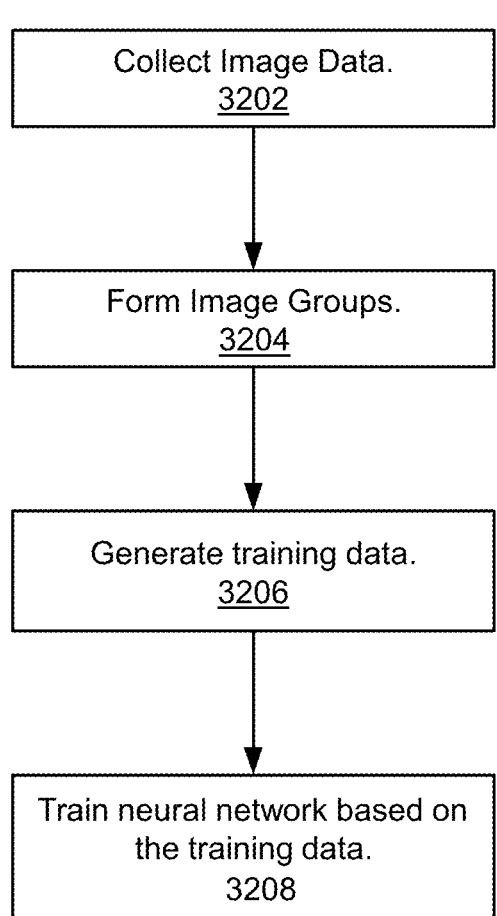
Collect Image Data.
3202
Form Image Groups.
3204
Generate training data.
3206
Train neural network based on
the training data.
3208
FIG. 32

3310                   3311

3320                   3322

3330                   3331

3400

3410

3400'

3411

IMAGE QUALITY ASSESSMENT AND MULTI MODE DYNAMIC CAMERA FOR DENTAL IMAGES

BACKGROUND

The practice of medicine is evolving toward tele-medi-cine—the remote treatment of patients. Telemedicine allows doctors to assess the patient's needs and in some instances, provide treatment suggestions for the patients without the hassle and risks involved in in person treatments. However, current systems and methods related to dental care are less than desirable in many ways. For example, many dental care contexts require a patient to physically consult with a dentist for various purposes, such as initial assessments, obtaining diagnoses for various conditions, obtaining treatment plans and/or appliances prescribed by treatment plans, and track-ing progress of a treatment. Existing dental care solutions may not be convenient or cost effective and rely on live consultations and/or diagnoses. Such in-person solutions can be particularly problematic during times when dental offices are inaccessible due to emergencies, pandemics, physical inaccessibility, and/or impracticality.

Orthodontic and dental treatments are carried out in person. Orthodontic treatment, such as those using a series of patient-removable appliances (e.g., "aligners") are very useful for treating patients. Treatment planning is typically performed in a dental office conjunction with the dental professional (e.g., dentist, orthodontist, dental technician, etc.), by generating a model of the patient's teeth in a final configuration and then breaking the treatment plan into a number of intermediate stages (steps) corresponding to individual appliances that are worn sequentially. This pro-cess may be interactive, adjusting the staging and in some cases the final target position, based on constraints on the movement of the teeth and the dental professional's prefer-ences. Once the final treatment plan is finalized, the series of aligners may be manufactured corresponding to the treat-ment planning. A patient's treatment plan may include obtaining images of the patient's teeth. The images may include photographic images, dental scans, x-ray images, stitched images, video images, and the like.

Clear, undistorted images of the patient's teeth may assist the clinician in generating the patient's treatment plan. If, however, the images of the patient's teeth are not of suffi-cient quality (clear, undistorted, including sufficient teeth), then the patient's recommended treatment may be inaccu-rate, or in some cases the clinician may not be able to generate a recommended treatment (e.g., treatment plan) at all.

Thus, there is a need for determining whether a dental image is of sufficient quality to use for treatment planning.

In addition, current systems and methods related to remote or virtual dental care rely on patients to capture images of their face and dentition without patient guidance for using assistive devices and the correct cameras or other image capture devices to capture accurate and clear images of the patient's face and dentition, including the teeth, gingiva, lips, mouth opening, and face. This often results in inconsistent images and images that do not capture clinically relevant information.

SUMMARY

As will be described in greater detail below, the present disclosure describes various systems and methods for virtual dental care to remote patients.

Smartphones and other mobile devices, having readily available high-resolution cameras, allow patients to take sufficiently high-resolution photos that may enable the prac-titioner to inspect patients. The systems and methods pro-vided in this disclosure may utilize artificial intelligence and machine learning to provide a patient with guidance on taking clinically relevant orthodontic photos and to assess the image quality of the photos. To aid in taking photos, patients may or may not use various assistive devices or accessories, such as a cheek retractor, or an attachment on the smartphone such as a photo tube device, such as the Invisalign Lens. However, patients may not know how to properly utilize such assistive devices. In addition, when being provided guidance, the guidance may need to be tailored to what assistive devices are in use as well as who is capturing the photos (e.g., by the patients themselves or via assistance).

As will be described further below, the systems and methods provided in this disclosure may utilize artificial intelligence to provide a patient with customized real-time guidance on taking clinically relevant orthodontic photos either with or without assistive devices. The systems and methods provided in this disclosure may improve the func-tioning of a computing device by more efficiently acquiring image data, which may further reduce storage requirements and network bandwidth. In addition, the systems and meth-ods described herein may improve the functioning of a computing device by reducing computing resources and overhead for acquiring and storing updated patient data, thereby improving processing efficiency of the computing device over conventional approaches.

In addition, the systems and methods provided herein may improve the field of virtual medicine by improving the functional capabilities of remote devices. Moreover, the systems and methods provided herein may improve the field of medical imaging by providing a near-real-time classifi-cation of images for various classifiers as well as stream-lining a process for acquiring relevant images. These sys-tems and methods may also improve the field of orthodontic treatment by analyzing data to efficiently target treatment areas and providing patients with access to more practitio-ners than conventionally available.

A computer-implemented method for assisted clinically relevant photo capture is provided. The method may include determining a photo capture mode for capturing a plurality of clinically relevant photos of a person's dentition satisfy-ing clinically acceptable criteria. The clinically acceptable criteria may include a plurality of clinically acceptable positions and a plurality of clinically acceptable orientations of teeth relative to a camera. The method may also include, determining, based on the photo capture mode, one or more photo parameters to define the clinically acceptable criteria. A response to the one or more photo parameters may be provided. The response may include providing, automated instructions for capturing the plurality of clinically relevant photos. Preliminary photos from the camera may be prepro-cessed in response to the automated instructions. The plu-rality of clinically relevant photos may be captured using the camera based on the preprocessed preliminary photos.

Described herein are various apparatus (e.g., system, device, method, or the like) that can determine and/or identify whether an image, such as a dental image, includes sufficient quality for use with dental treatment recommen-dations, monitoring and/or planning. In some examples, these apparatuses and methods may include a machine learning agent (e.g., neural network) that is trained to score the overall image quality of an image, and in particular, of a dental image.

In general, described herein are methods of assessing an image quality of an image (e.g., a dental or other medical image). Any of these methods may include: receiving a first image; cropping the first image; generating a score of overall image quality for the cropped first image using a trained neural network, wherein the trained neural network is trained using a plurality or ranked sub-sets of images (e.g., similar dental or medical images) and a loss function configured to preserve a relative ranking order of the ranked sub-sets of images, further wherein the sub-sets of images are ranked based on overall image quality; and outputting an indicator of the score of overall image quality. The overall image quality may also be referred to as the perceived overall image quality as perceived by the trainers (e.g., human labelers) generating the training data set. As described herein, the perceived overall image quality may include a variety of image quality factors, not limited to just focus (blurriness, fuzziness, etc.), sharpness, color, brightness, contrast, etc. that may not be explicitly defined. Further the quality of overall image quality refers to the overall image quality of the particular region of the image containing the teeth, or teeth and gingiva, or in some cases teeth and/or gingiva, and/or other oral regions (e.g., lips). Thus, other regions in the image, outside of the teeth and/or gingiva and/or lips, may be ignored and will not contribute to the overall image quality indicator or assessment.

Thus, in any of the methods and apparatuses described herein the images may be masked to remove non-target regions (e.g., for dental image, regions outside of the teeth and/or gingiva and/or lips). Any of these methods may include masking the cropped first dental image to mask out regions that do not correspond to teeth or teeth and gingiva prior to generating the score of overall image quality.

The methods described herein may generally process the image (e.g., first dental image) without normalizing the image; for example, without resizing the image. Resizing or otherwise normalizing the images being assessed may result in a loss of fidelity. Thus, the methods described herein may be performed on an un-resized first dental image when generating the overall image quality score.

In any of these methods, generating the score of overall image quality for the cropped and masked first dental image may comprising using the trained neural network, wherein the trained neural network is trained using a plurality of ranked sub-sets of dental images that are masked to mask out regions that do not correspond to teeth or teeth and gingiva. The formation and operation of the trained neural network is described in detail below.

The indicator of the score of overall image quality may be configured to indicate that the overall image quality is sufficient for use with a dental treatment plan. For example, the indicator may be determined based on a threshold that is set to a level appropriate for providing treatment recommendations, monitoring and/or planning, e.g., showing sufficient detail and quality to allow modeling of the patient's teeth.

In general, outputting the indicator of the score of overall image quality may comprise providing feedback to a user of an assessed overall image quality. The first dental image may be captured with any appropriate camera, including a patient- or user-operated camera, such as a tablet computer, a cell phone, or a laptop computer. Generating the score of overall image quality is performed on a local processor. The local processor may be one of: a processor of a cell phone, a processor of a tablet, or a processor of a laptop computer. In some examples these method and apparatuses (e.g., software) may operate on a user device such phone, laptop, table, etc. and may be operated via web browser or via dedicated local software. In some examples, any of the methods may be performed on a remote processor or through remotely accessed computing resources such as, but not limited to, internet accessed cloud-based resources.

In any of these methods receiving the first dental image may comprises receiving the first dental image from a cloud-based data storage device.

Any of these methods and apparatuses my include calculating the indicator of the score of overall image quality by applying a threshold to the score of overall image quality. The score of overall image quality may be a numeric score (e.g., a score between 0-1, 1-10, 0-10, etc.). and the threshold may be determined by the user (e.g., physician, technician, etc.) or may be predetermined. In some examples the threshold(s) may set one or more ranges of indicators such as "excellent," "good," "acceptable," "poor" and/or "unacceptable." In some examples only two indicators are provided (e.g., good/poor, acceptable/unacceptable). In some cases the numeric score (which may be normalized or adjusted, e.g., from 0-1 to 0-100%, etc.) may be used. In some examples the threshold indicates good or poor overall image quality.

The first image (e.g., first dental image) may be any appropriate image. For example, the first dental image may be a digital photographic image, an image from a video or scan (e.g., intraoral scan), an x-ray image, a panoramic dental scan image, a stitched image based on two or more individual images, or any combination of these. Although the examples described herein are specific to individual frames or images, in some examples the methods and apparatuses described herein may be applied to videos, video clips, video streams, etc., and may compare individual frames in a continuous (using all individual frames from the video) or discrete manner (e.g., using selected individual frames sampled from the video) and/or averaged video frames.

In any of the methods and apparatuses described herein outputting the indicator of the score of overall image quality may comprise indicating that a new dental image should be captured. In some examples outputting the indicator of the score of overall image quality comprises providing guidance to improve the image quality. For example, the method may include outputting a link to a video showing how to capture quality dental images. In some examples outputting the indicator of the score of overall image quality comprises displaying, in a browser window, the score of overall image quality (or a scaled representation of the numeric score).

The trained neural network may be trained using ranked sub-sets of dental images comprising ranked pairs of dental images. In any of these methods and apparatuses, the perceived overall image quality may include one or more of: perceived image darkness, perceived image blurriness, focus, inclusion of shadows, or a combination thereof.

As mentioned above the images being analyzed and/or the images on which the machine learning agent is trained may be masked. The masking may be based on a neural network trained to identify teeth within each of the dental images. The trained neural network may be a convolutional neural network.

For example, a method of assessing an image quality of a dental image may include: receiving a first dental image; cropping the first dental image; masking the cropped first dental image to mask out regions that do not correspond to teeth or teeth and gingiva; generating a score of overall image quality for the cropped and masked first dental image using a trained neural network, wherein the trained neural network is trained using a plurality or ranked sub-sets of dental images and a loss function configured to preserve a relative ranking order of the ranked sub-sets of dental images, further wherein the sub-sets of dental images are ranked based on perceived overall image quality, wherein the plurality or ranked sub-sets of dental images are masked to mask out regions that do not correspond to teeth or teeth and gingiva; and outputting an indicator of the score of overall image quality.

Also described herein are apparatuses configured to perform any of these methods. For example, described herein are apparatus for assessing an image quality of a dental image that include: one or more processors; and a memory storing instructions that, when executed by the one or more processors, causes the one or more processor to perform a method comprising: receiving a first dental image; cropping the first dental image; generating a score of overall image quality for the cropped first dental image using a trained neural network, wherein the trained neural network is trained using a plurality or ranked sub-sets of dental images and a loss function configured to preserve a relative ranking order of the ranked sub-sets of dental images, further wherein the sub-sets of dental images are ranked based on perceived overall image quality; and outputting an indicator of the score of overall image quality.

The instructions stored in the memory may encode any of the steps and features described above. For example, the instructions may cause the one or more processor to mask the cropped first dental image to mask out regions that do not correspond to teeth or teeth and gingiva prior to generating the score of overall image quality. The instructions may cause the one or more processor to generate the score of overall image quality for the cropped and unresized masked first dental image by using the trained neural network, wherein the trained neural network is trained using a plurality of ranked sub-sets of dental images that are masked to mask out regions that do not correspond to teeth or teeth and gingiva.

In any of these apparatuses, the instructions may cause the one or more processor to include an indicator of the score of overall image quality that is configured to indicate that the overall image quality is sufficient for use with a dental monitoring, recommendations and/or treatment planning. The indicator of the score of overall image quality may include providing feedback to a user of an assessed overall image quality. The instructions may cause the one or more processor to locally determine the score of overall image quality, e.g., performing it on the one or more, local, processors, or communicating with a remote (e.g., cloud) processor. The one or more local processors may be one of: a processor of a cell phone, a processor of a tablet, or a processor of a laptop computer. Receiving the first dental image may comprise receiving the first dental image from a cloud-based data storage device. The instructions may cause the one or more processor to calculate the indicator of the score of overall image quality by applying a threshold to the score of overall image quality. For example, the threshold may indicate good or poor overall image quality.

The instructions may cause the one or more processor to process any appropriate first (e.g., dental) image. For example, the instructions may be configured to operate on a first dental image that is a digital photographic image, an x-ray image, a panoramic dental scan image, a video image, a stitched image based on two or more individual images, or a combination thereof.

In any of these examples the instructions may cause the one or more processor to output the indicator of the score of overall image quality that comprises indicating that a new dental image should be captured. For example, outputting the indicator of the score of overall image quality may comprise providing a link to a video showing how to capture quality dental images. In some examples, the instructions may cause the one or more processor to output the indicator of the score of overall image quality comprises displaying, in a browser window, the score of overall image quality. The trained neural network may be trained using ranked sub-sets of dental images comprising ranked pairs of dental images. The perceived overall image quality may include one or more of: perceived image darkness, perceived image blurriness, focus, inclusion of shadows, or a combination thereof.

As mentioned above, the instructions may cause the one or more processor to mask the first dental image and/or the images used for training. Masking may be based on a neural network trained to identify teeth within each of the dental images.

In general, the trained neural network may be a convolutional neural network.

Also described herein is the software that may perform any of these methods. For example, described herein is non-transitory computer-readable storage medium storing instructions that, when executed by one or more processors of a device, cause the one or more processors to perform a method comprising: receiving a first dental image; cropping the first dental image; generating a score of overall image quality for the cropped first dental image using a trained neural network, wherein the trained neural network is trained using a plurality or ranked sub-sets of dental images and a loss function configured to preserve a relative ranking order of the ranked sub-sets of dental images, further wherein the sub-sets of dental images are ranked based on perceived overall image quality; and outputting an indicator of the score of overall image quality.

Also described herein are methods and apparatuses (e.g., systems) for training the machine learning agent (e.g., neural networks) described herein. For example, the neural network may be trained with training data that includes a plurality of images. The images may be arranged into groups. Within each of the groups, the images may be ranked or labeled to indicate which of the images have comparatively more quality. In this manner, the neural network may be trained to determine or indicate whether any considered images may include sufficient quality. In some examples, if the training data includes ranked and labeled images that include sufficient quality for use with dental monitoring, recommendations and/or treatment planning, then the neural network may be trained to determine whether any images include sufficient quality for use with dental monitoring, recommendations and/or treatment planning. The ranking and/or labelling may be based on a perceived image quality.

In general, a processor may train the neural network by determining an output of a loss function that compares the output of the neural network in response to the training data. The output of the loss function may be backpropagated to the neural network.

A neural network trained to identify images that include sufficient quality for use for dental monitoring, recommendations and/or treatment planning may advantageously be used to provide users, particularly unskilled users, feedback regarding images that may be submitted for use. The neural network can provide an indication of whether the image is acceptable for use without requiring the intervention of a trained technician. In this manner, successful image capture may be performed beyond clinical settings, in some cases in remote settings through virtual care, telehealth, or the like. In some examples, the neural network may be trained with 1000's or 100,000's of images. Such a vast training data set may enable the neural network to learn or incorporate several aspects of quality, even those aspects that may be considered subjective.

Described herein are various methods for training a machine learning model to assess dental image quality. For example, the methods may include obtaining a set of dental images, forming a plurality of image groups from the set of dental images, ranking, by a plurality of people, dental images within each of the plurality of image groups, wherein the ranking is based on a perceived image quality, and training, by a processor, a neural network to determine whether a dental image includes sufficient image quality to be used with a dental monitoring, recommendations and/or treatment planning based on the ranked dental images.

Generally, in any of the methods described herein, the set of dental images may include photographic images. In some examples, the set of dental images may include x-ray images, panoramic dental scan image, video images, images based on two or more individual images, or a combination thereof.

Generally, the plurality of image groups may include any number of dental images. In some examples, each of the plurality of image groups may include two dental images from the set of dental images. For example image groups that include two dental images, the ranking may indicate which dental image within each of the plurality of image groups has the better perceived image quality of the two images. In some examples, the ranking may indicate that both dental images within each of the plurality of image groups have approximately the same perceived image quality.

In any of the methods described herein, each of the plurality of image groups may include three or more dental images from the set of dental images. For example image groups that include three or more dental images, the ranking may indicate that all dental images within each of the plurality of image groups may have approximate the same perceived image quality.

Generally, in any of the methods described herein, the ranking may indicate which dental image within each of the plurality of image groups has the highest perceived quality. In some examples, the perceived quality may be based on perceived image darkness, perceived image blurriness, focus, inclusion of shadows, or a combination thereof. Furthermore, in some examples, the ranking may be based on the perceived image quality of teeth within each of the dental images.

Any of the methods described herein may include masking the dental images such that non-tooth objects within each of the dental images are not shown, wherein the ranking may be based, at least in part, on the masked dental images. In some examples, the masking may be based on a neural network trained to identify a region of interest (e.g., teeth, a tooth, gingiva, etc.) within each of the dental images.

Generally, in any of the methods described herein training the neural network may include determining a loss function output based on the ranking of the dental images with each of the plurality of image groups. In some examples, the loss function output may be based on a predicted quality output of a neural network of each of the dental images within the plurality of image groups. Furthermore, in some examples the loss function output may be backpropagated to train the neural network. The loss function output may be based on a predicted image quality of a first dental image and a second dental image within each of the plurality of image groups.

In any of the methods described herein the neural network may be a convolutional neural network. In some examples, the training may modify the convolutional neural network to identify dental images with sufficient image quality for use with dental monitoring, recommendations and/or treatment planning. Generally, in any of the methods described herein, the dental images may be restricted to non-resized images.

Described herein are various apparatuses for training a machine learning model to assess dental image quality. In some examples, an apparatus may include a communication interface, one or more processors, and a memory storing instructions that, when executed by the one or more processors, cause the apparatus to obtain, through the communication interface, a set of dental images, form a plurality of image groups from the set of dental images, rank, by a plurality of people, dental images within each of the plurality of image groups, wherein the ranking is based on a perceived image quality, and train, by a processor, a neural network to determine whether a dental image includes sufficient image quality to be used with a dental treatment plan based on the ranked dental images.

Also described herein are various non-transitory computer-readable storage mediums storing instructions that, when executed by one or more processors of a device, cause the device to obtain a set of dental images, form a plurality of image groups from the set of dental images, rank, by a plurality of people, dental images within each of the plurality of image groups, wherein the ranking is based on a perceived image quality, and train, by a processor, a neural network to determine whether a dental image includes sufficient image quality to be used with a dental treatment plan based on the ranked dental images.

Described herein are various methods of assessing an image quality of a dental image, the method may include receiving, through a communication interface, a first dental image, assessing, by a processor executing a neural network, an image quality of the first dental image, wherein the neural network is trained to indicate whether the image quality is sufficient for use with a dental treatment plan, and providing feedback to a user based on the assessed image quality.

In any of the methods described herein, the first dental image may be captured with camera included within at least one of a tablet computer, a cell phone, and a laptop computer. Furthermore, in any of the methods described herein, the neural network may be executed by at least one of a processor of a tablet computer, a processor of a cell phone, and a processor of a laptop computer.

Generally, for any of the methods described herein, receiving the first dental image may include receiving the dental image from a cloud-based storage device. In some examples, the first dental image may be used for at least one of originating or modifying dental monitoring, recommendations and/or treatment planning. In some examples, providing feedback may include instructing the user to capture a second dental image. In some other examples, providing feedback may alternatively or additionally include sending the user a link to a video showing how to capture quality dental images.

Any of the methods described herein may include displaying, in a browser window, the assessed image quality from the neural network. In some examples, the first dental image may be extracted from a video frame. In some examples, the first dental image may be combined from a plurality of individual images.

Any of the apparatuses described herein may include an apparatus for assessing an image quality of a dental image. In some examples, an apparatus may include a communication interface, one or more processors, and a memory storing instructions that, when executed by the one or more processors, causes the apparatus to receive, through a communication interface, a first dental image, assess, by a processor executing a neural network, an image quality of the first dental image, wherein the neural network is trained to indicate whether the image quality is sufficient for use with a dental treatment plan, and provide feedback to a user based on the assessed image quality.

Also described herein are various non-transitory computer-readable storage mediums storing instructions that, when executed by one or more processors of a device, cause the device to receive, through a communication interface, a first dental image, assess, by a processor executing a neural network, an image quality of the first dental image, wherein the neural network is trained to indicate whether the image quality is sufficient for dental monitoring, recommendations and/or treatment planning, and provide feedback to a user based on the assessed image quality.

All of the methods and apparatuses described herein, in any combination, are herein contemplated and can be used to achieve the benefits as described herein.

INCORPORATION BY REFERENCE

All patents, applications, and publications referred to and identified herein are hereby incorporated by reference in their entirety, and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which:

FIG. 1D shows a block diagram of an example system for intelligent patient guidance, in accordance with some embodiments.

FIG. 1E shows a block diagram of an example system for photo-based refinement, in accordance with some embodiments.

FIG. 1F shows a block diagram of an example system for intelligent patient guidance, in accordance with some embodiments.

FIG. 3 shows a flow diagram of example method for photo guidance, in accordance with some embodiments.

FIG. 4 shows an example user device for photo guidance, in accordance with some embodiments.

FIG. 8 shows a differential error image of teeth of a patient for a stage of treatment, according to embodiments herein.

FIG. 9 an outlined differential error image of teeth of a patient for a stage of treatment, according to embodiments herein.

FIG. 10 an outlined differential error image of teeth of a patient for a stage of treatment, according to embodiments herein.

FIG. 11 shows a side-by-side of a rendered teeth image and actual teeth image of a patient for a stage of treatment.

FIG. 12 shows charts of differential error for teeth of a patient for each stage of treatment, according to embodiments herein.

FIG. 18 shows segmented mesh teeth arches generated from existing scans of a patient's teeth and 2D images for a patent's teeth, according to embodiments herein.

FIG. 24 shows a method of assessing the quality of seating for clear aligners, in accordance with some embodiments.

FIG. 25A shows example image data of a patient's dentition with a clear aligner, in accordance with some embodiments.

FIG. 25B shows example mask data derived from the image data of FIG. 25A, in accordance with some embodiments.

FIG. 25C shows the mask data of FIG. 25B overlaid onto the image data of FIG. 25A, in accordance with some embodiments.

FIG. 26 shows a flow chart of multi mode photo guidance, in accordance with some embodiments.

FIG. 27 shows an illustration of a patient using a retractor, in accordance with some embodiments.

FIG. 29 shows a method of multi mode photo guidance, in accordance with some embodiments.

FIG. 32 is a flowchart showing an example method for training a neural network to assess and/or determine an image quality of a dental image, in accordance with some embodiments.

DETAILED DESCRIPTION

Figure 1A:
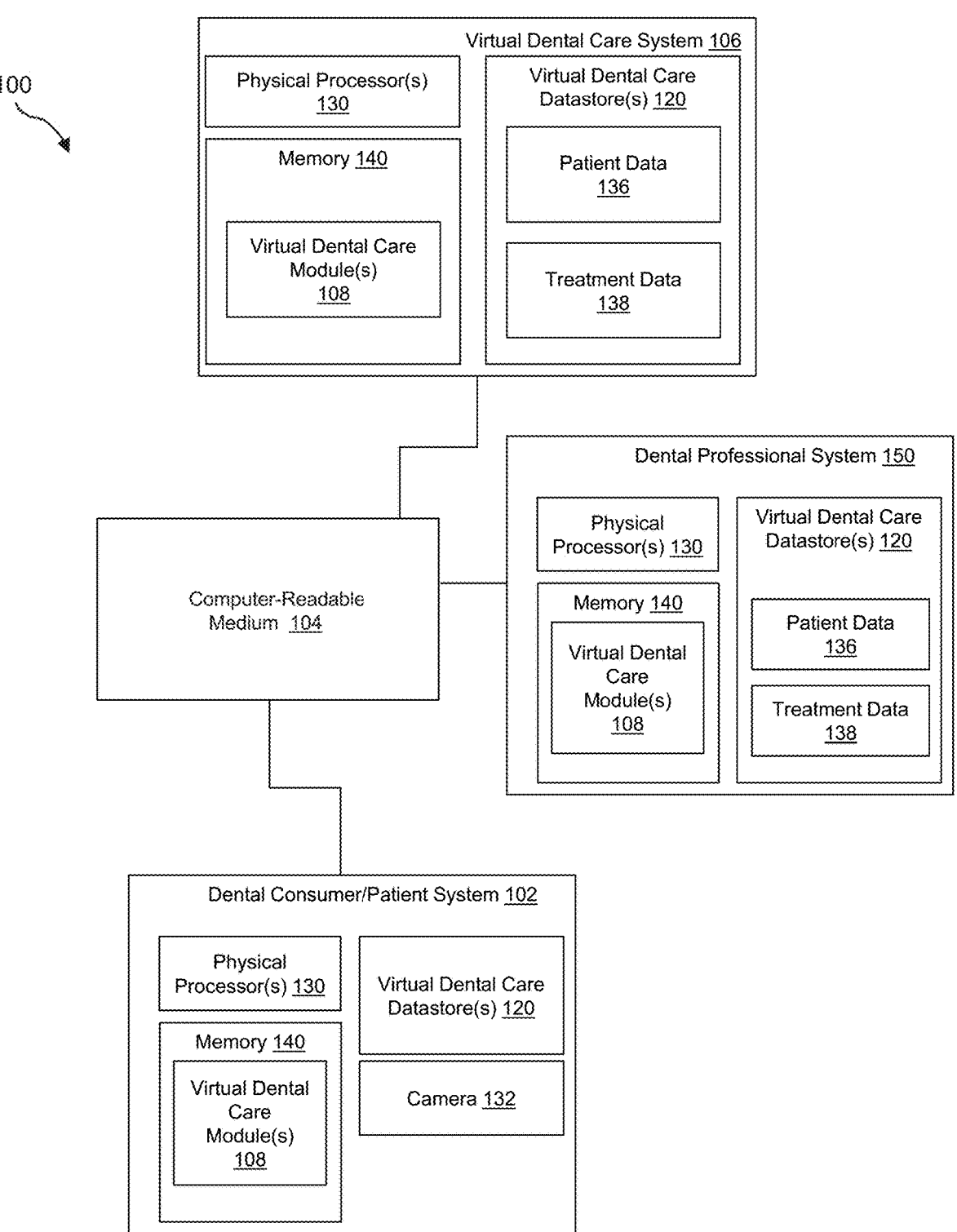
FIG. 1A shows a block diagram of an example system for virtual dental care, in accordance with some embodiments.

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein. For example, although discussion is provided with respect to capturing and assessing dental images, the methods and systems disclosed herein may also be used for other medical imaging and diagnostics related to other areas of the body. As additional examples, while discussion is provided with respect to the capture and use of 2D images with 2D image capture devices, in some embodiments, the teachings herein may be similarly applied to the capture of color images during 3D scanning with an intraoral 3D scanner or other 3D scanning device.

Multi Mode AI Based Image Capture

As described herein, smartphones and other mobile devices, having readily available high-resolution cameras, allow patients to take sufficiently high-resolution photos that may enable the practitioner to inspect patients. As further described herein, the systems and methods provided in this disclosure may utilize artificial intelligence to provide a patient with guidance on taking clinically relevant orthodontic photos. To aid in taking photos, patients may or may not use various assistive devices or accessories, such as a cheek retractor, or an attachment on the smartphone such as a photo tube device. As used herein, the term "photo tube" refers to an assistive device that may include a structure configured to be coupled to a smartphone and further configured to provide a physical channel or tube extending between a camera of the smartphone and a patient's anatomy, such as the dentition, including and a region of interest (e.g., a portion of the oral cavity or a portion of the patient's detention within the oral cavity). For example, a photo tube may confine a view or field of view of a camera to the particular region of interest. The photo tube may have a known tube length so as to position the camera at a known distance or distance range from the anatomy. However, patients may not know how to properly utilize such assistive devices. In addition, when being provided guidance, the guidance may be tailored to what assistive devices are in use as well as who is capturing the photos (e.g., by the patients themselves or via assistance).

As will be described further below, the systems and methods provided in this disclosure may utilize artificial intelligence to provide a patient with customized real-time guidance on taking clinically relevant orthodontic photos either with or without assistive devices. The systems and methods provided in this disclosure may improve the functioning of a computing device by more efficiently acquiring image data, which may further reduce storage requirements and network bandwidth. In addition, the systems and methods provided herein may improve the field of virtual medicine by improving the functional capabilities of remote devices. Moreover, the systems and methods provided herein may improve the field of medical imaging by providing a near-real-time classification of images for various classifiers as well as streamlining a process for acquiring relevant images.

The disclosed methods and systems also enable the provision of real-time feedback to the patient, enabling a faster, more effective photo capture experience. For example, if posterior teeth are not visible, the user would be prompted in real time to pull back on their assistive device, such as their cheek retractor to better reveal their posterior teeth for image capture. Real-time assistance allows for the capture of better photographs, thereby improving patient treatment and monitoring (e.g., enabling improved and earlier detection of issues, thus enabling corrective measures) and resulting outcomes. Real-time assistance also improves efficiency of treatment monitoring. For example, by intelligently evaluating and assisting in photo capture, the need to take multiple photographs or additional photographs (e.g., in the event that an initial set of photographs proves unsatisfactory following evaluation by a dental professional) may be reduced.

Figure 30:
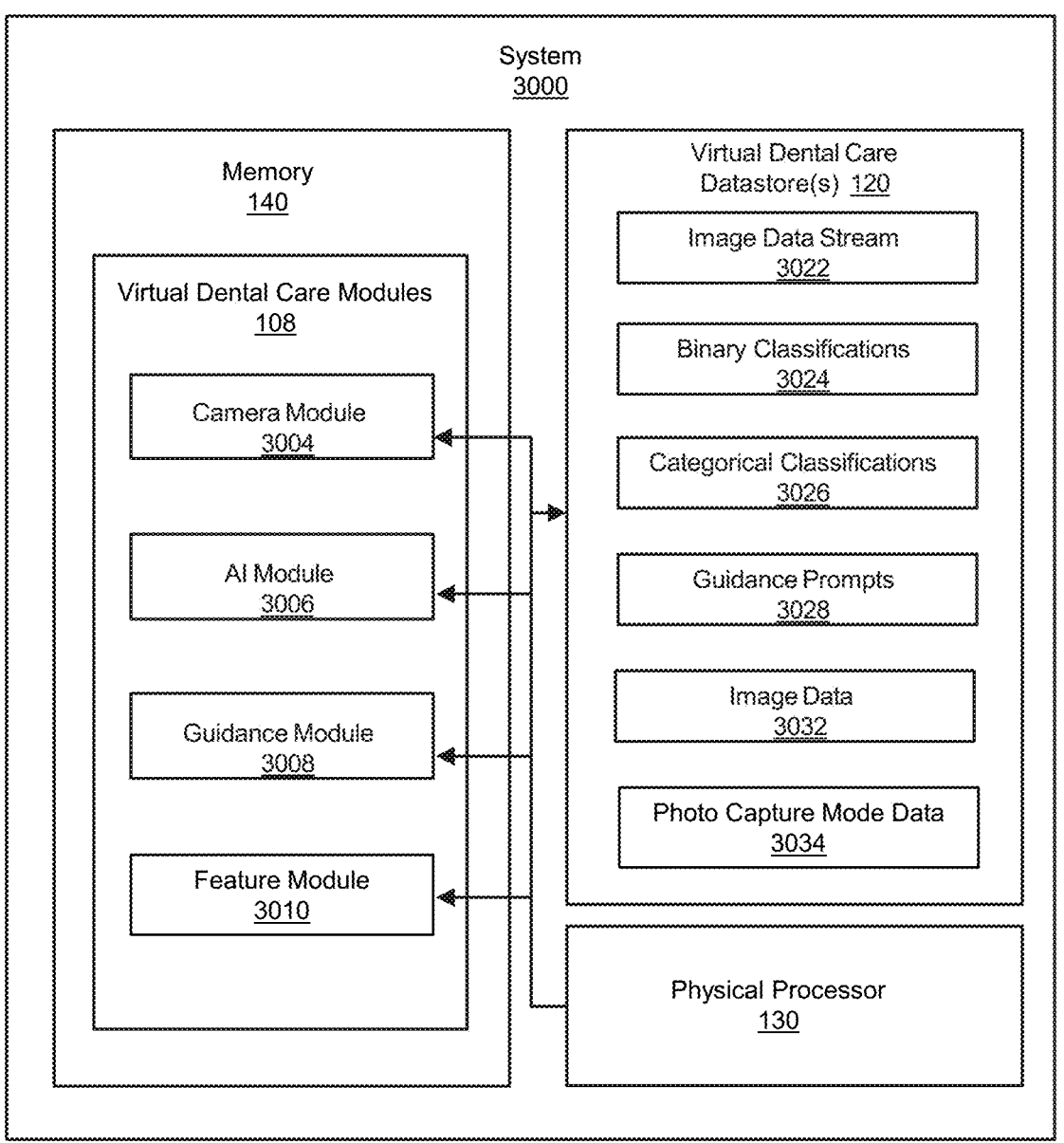
FIG. 30 shows a block diagram of an example system for multi mode AI based photo guidance, in accordance with some embodiments.

With reference to FIG. 30, a block diagram of an example system 3000 for multi mode AI based photo guidance is provided. As illustrated in this figure, example system 3000 may include one or more virtual dental care modules 108 for performing one or more tasks. As will be explained in greater detail below, virtual dental care modules 108 may include a camera module 3004, an AI module 3006, and a guidance module 3008. Although illustrated as separate elements, one or more of virtual dental care modules 108 in FIG. 30 may represent portions of a single module or application.

In certain embodiments, one or more of virtual dental care modules 108 in FIG. 30 may represent one or more software applications or programs that, when executed by a computing device, may cause the computing device to perform one or more tasks. For example, and as will be described in greater detail below, one or more of virtual dental care modules 108 may represent modules stored and configured to run on one or more computing devices, such as the devices illustrated in FIG. 1A (e.g., dental patient system 102 and/or server 106). One or more of virtual dental care modules 108 in FIG. 30 may also represent all or portions of one or more special-purpose computers configured to perform one or more tasks.

As illustrated in FIG. 30, example system 3000 may also include one or more virtual dental care datastore(s) 120, such as an image data stream datastore 3022, binary classifications datastore 3024, categorical classifications datastore 3026, guidance prompts datastore 3028, image data 3032, and photo capture mode data 3034. Virtual dental care datastore(s) 120 may comprise one or more datastores configured to store any type or form of data or information.

FIG. 26 is a flow chart of an exemplary computer-implemented method 2600 of multiple mode AI based photo guidance. As discussed herein, the AI based photo guidance provides guidance based on the use, such as a detected use of one or more of multiple devices. The multiple devices may include assistive device and camera devices. Assistive devices may include cheek retractors, a photo tube, lack or cheek retractors or other assistive device, a mirror, etc. Camera devices may include smartphone or other cameras, such as front facing cameras (e.g., wherein a camera and screen are on the same side of a device) or rear facing The photo capture mode may define, for example, a capture order, a guidance for the capture order, how to present the guidance, as well as various preprocessing parameters. The following table provides example photo capture modes, which may be stored as photo capture mode data 3034. Although the capture modes shown therein include example capture orders for each mode, in some embodiments, the capture order may be modified and/or additional views may be captured. Such additional views and different orders may be determined dynamically, such as by the algorithm during the capture mode. The dynamic order may be determined in real-time. For example, feedback provided based on captured images may direct the user to take additional views, such as when a oral defect, such as gingival recession or tooth damage is detected in the captured photos. The module may direct the patient to take more directed photos of the recession region or the tooth. In some embodiments, tracked tooth movements during orthodontic treatment may indicated that one or more teeth are not moving correctly based on the predicted or planed movement in the treatment plan. In such cases, the user may be directed to take photos of the particular teeth or tooth that is not moving correctly. The system may guide the user to take the additional photos at a particular angle and distance and may guide the use of an assistive device.

TABLE 1

| Photo Capture Mode Device | Front/ Back Camera | Assisted/ Alone | Features Face Detection | Face Landmark | Cropping | Mirror Writing | AI Model Preprocessing | Capture Order |
|---|---|---|---|---|---|---|---|---|
| Photo tube | Back | Assisted | No | No | Photo tube Crop | No | Resize + 2:1 padding | Right → Center → Left |
| Photo tube | Back | Alone | No | No | Photo tube Crop | Yes | Resize + 2:1 padding | Right → Center → Left |
| Retractor | Front | Alone | Yes | Yes | Mouth Crop | No | Resize | Center → Right → Left |
| Retractor | Back | Alone | Yes | Yes | Mouth Crop | Yes | Resize | Center → Right → Left |
| Retractor | Back | Assisted | Yes | Yes | Mouth Crop | No | Resize | Center → Right → Left |
| None | Front | Alone | Yes | Yes | Mouth Crop | No | Resize | Center → Right → Left |
| None | Back | Alone | Yes | Yes | Mouth Crop | Yes | Resize | Center → Right → Left |
| None | Back | Assisted | Yes | Yes | Mouth Crop | No | Resize | Center → Right → Left | cameras (e.g., wherein a camera and lens are on different sides of the device), etc. The steps shown in FIG. 26 may be performed by any suitable computer-executable code and/or computing system, including the system(s) illustrated in FIGS. 1 and 2. In one example, each of the steps shown in FIG. 26 may represent an algorithm whose structure includes and/or is represented by multiple sub-steps, examples of which will be provided in greater detail below.

As illustrated in FIG. 26, at step 2602 one or more of the systems described herein may initiate capture of a next photo in an algorithm (which may be embodied in a script or other computer executable instructions). The algorithm may include an order in which to capture the photos, and a photo capture mode.

For example, based on a type of assistive device that is or is not present (e.g., a photo tube, a retractor, or none) and whether or not the patient is taking photos themselves or is being assisted by someone else, the photo capture mode may be accordingly selected. In some examples, the settings may be manually input. In other examples, the settings may be automatically detected, for example, by polling a front camera and a back camera of a mobile device, such as by reading image data from the image data stream 3022. A photo tube device may be identified by the AI modules 3006 in the back camera as the photo tube device may be attached to a back side of the mobile device, as will be described further below. A retractor may be identified by the AI modules 3006 in the front camera (if the patient is unassisted) or the back camera (if the patient is assisted). The patient may be assisted if a different person is identified in both the front and back cameras.

In some embodiments, a patient may be unassisted if the same person is identified in both the front and back cameras. For example, in some embodiments, the patient may be seen in both front and back cameras when the patient uses the back camera to capture clinically relevant photos while using a mirror to see the screen of an electronic device, such as a smart phone. In such embodiments, the front camera may capture the reflection of the patient in the mirror while the back camera captures an image of the actual patient.

The AI modules 3006 may determine a camera to use based on the assistive devices used. For example, because the photo tube device is attached to the back side of the mobile device, the back camera may be best suited for capturing clinically relevant images. If a retractor or no device is used, either camera may be used (e.g., selected by using the camera detecting a person), which may be further determined by whether the patient wishes to face the display and/or whether the patient is being assisted.

In addition, based on the camera used, the guidance modules 3008 may provide guidance prompts, such as those from guidance prompt data store 3028 that are mirrored. For example, if the patient is using the front camera and facing the display, the guidance prompts 3028 (e.g., text, symbolic, or other visual guidance prompts) may be normally displayed. However, if the patient is using the back camera unassisted, the patient may use a mirror to see the guidance prompts 3028 on the display. In such scenarios, the guidance prompts 3028 may be mirrored. Moreover, if the patent is being assisted (such that the patient is captured with the back camera and allowed the assistant to view the display), the guidance prompts 3028 may be displayed normally for the assistant. In some embodiments, the guidance prompts 3028 may comprise nonvisual prompts (e.g., audio, haptic, etc.).

The photo capture mode may also define a capture order from the photo capture mode data 3034. In certain photo capture modes (e.g., retractor mode or no device mode) it may be easier and more intuitive for the patient to capture a center view of the patient's dentition first, followed by side views of the patient's dentition (e.g., right and then left or alternatively left and then right). Thus, when in retractor mode or no device mode, the system may send guidance prompts guiding the patient to capture a center view, followed by one or more side views. In other photo capture modes (e.g., photo tube mode), the assistive device may be easier to use by starting from one side and moving to the other side (e.g., right, center, then left, or alternatively, left, center, then right). Thus, when in the photo tube mode or other similar photo capture mode, the system may send guidance prompts guiding the patient to start capture from one side (e.g., a left side) and then moving to the other side (e.g., a right side).

FIG. 27 illustrates a usage 2700 of a patient 2702 using an assistive device to take photos of their dentition 2708 with a mobile device 2704. Patient 2702 may be using a retractor 2706. In FIG. 27, patient 2702 may be using a front camera of mobile device 2704 and is able to normally view a display of mobile device 2704. A cheek retractor pushes on the patient's lips and cheeks to retract the patient's cheeks and lips and enlarge the patient's mouth opening to expose the dentition for imaging. Cheek retractors may also move the patient's tissue, such are their lips and cheeks away from the patient's dentition to better expose the patient's detention for imaging. A cheek retractor may also keep the tissue in a retracted position during imaging and with or without the patient's assistance, such as by pulling or applying a force to the cheek retractor. A cheek retractor may include two cheek engaging structures 2712 connected by a frame 2710. A handle 2714 may extend from each of the cheek engaging structures 2712.

Figure 28:
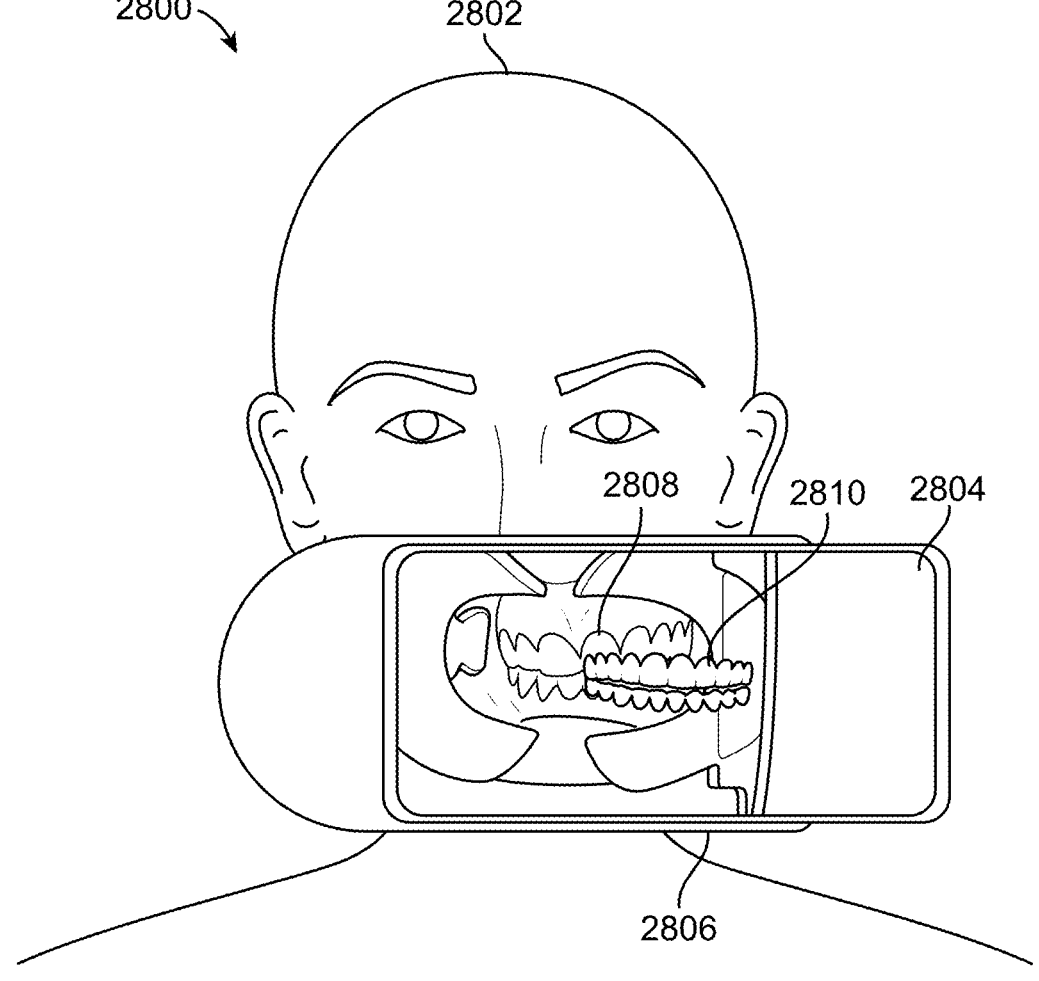
FIG. 28 shows an example illustration of a patient using a photo tube device, in accordance with some embodiments.

FIG. 28 illustrates a usage 2800 of a patient 2802 using an assistive device to take photos of their dentition 2808 with a mobile device 2804. In FIG. 28, patient 2802 may be using a photo tube 2806 attached to a back side of mobile device 2804. Photo tube 2806 may include cheek retractors 2812 aligned with a back camera of mobile device 2804. Because a guidance prompt 2810 may be displayed facing away from patient 2802, patient 2802 may use a mirror to see guidance prompt 2810. Here, the guidance prompts 2810 include an image of teeth. A patient may use the image from the patient's teeth for imaging by aligning the patient's teeth in the image taken by a camera, with the image of the teeth. The guidance prompts 2810 may also include displaying the image of the teeth in a location within the frame to guide the patient to move and rotate the camera to place it in the correct location and orientation for capturing a clinically appropriate image. In some embodiments, the guidance may include an indication to move or adjust an assistive device, such as to move a cheek retractor to retract the teeth further. This may include highlighting the retractor or other assistive device in the display and/or indicating a direction in which to move the retractor or other assistive device. In some embodiments, the mobile device, in addition to a guidance prompt, may a real-time image of the patient's teeth. In some embodiments, alternatively or additionally, a model (e.g., a rendering of a 3D model) corresponding to the patient's teeth is displayed to provide a real-time correspondence with the patient's teeth on the display of the mobile device.

Returning to FIG. 26, at step 2604 one or more of the systems described herein may display instructions, which may be guidance prompts 2810, for example as seen in FIG. 28. In some examples, as described herein, written instructions may optionally be mirrored such that the patient may read the instructions in a mirror. In some examples, the directions for how the patient should move with respect to the mobile device may also be mirrored. For instance, moving the mobile device to the right to capture a right lateral image on a cheek retractor may be equivalent to the patient turning their head to the left but holding the phone steady in a photo tube mode.

At step 2606 one or more of the systems described herein may optionally detect a face in an image of an image data or image data stream 3022 using the AI module 3006. For example, in certain photo capture modes (e.g., when using a retractor or no assistive device), the patient's face may be visible. By detecting the patient's face, the patient's face may be cropped for the final photo by the feature module, which may modify the image based on the features of the photo capture mode. In other photo capture modes (e.g., photo tube mode), the patient's face may not be visible (e.g., blocked by the photo tube) such that the patient's face may not be detected.

At step 2608 one or more of the systems described herein, such as the AI module 3006 may optionally detect a facial landmark, as determined by the feature module 3010 based on the photo capture mode data 3034. For example, in certain photo capture modes (e.g., when using a retractor or no assistive device), a facial landmark such as the patient's mouth may be visible. By detecting the facial landmark, the facial landmark may be cropped for the final photo. In other photo capture modes (e.g., photo tube mode), the facial landmark may not be visible (e.g., blocked by the photo tube) such that the facial landmark may not be detected.

At step 2610 one or more of the systems described herein, such as the feature module 3010 of system 3000 may crop the photo. A cropping process may be determined by the feature module 3010 based on the photo capture mode. For example, in the photo tube mode (in which the patient's face and facial landmarks were not detected), the cropping may be based on the visible portions of the photo tube itself. For example, the photo tube may be cropped out (see, e.g., the right side of the display in FIG. 28). In some embodiments, the photo may be cropped to a 2:1 aspect ratio, or some other suitable predetermined aspect ratio.

In other photo capture modes, as may be determined by the feature module 3010 based on the binary classifications and categorical classifications determined by the AI module 3006 using the photo capture mode data 3034 (e.g., retractor mode or no device mode), the detected face and/or facial landmark may be cropped out of the image. In some embodiments, the cropping may be based on the determined photo capture mode. For example, a first cropping setting may be applied for an image captured in retractor mode, and a second cropping setting may be applied for an image captured in a no device mode. For example, the photo may be cropped based on the location of the patient's mouth. In some embodiments, the cropping may be based on a treatment characteristic. For example, the patient's teeth may be relevant for a particular treatment, while other patient anatomy (e.g., gingiva above a certain cut line) that may be included in the image not be relevant for the particular treatment. The system may crop the photo to retain the relevant anatomy, such as the oral cavity and the dentition, while discarding the irrelevant portion or portions of the image. For a different treatment, the gingiva may be more relevant, in which case, less of the gingiva may be cropped out. In some embodiments, a portion of the anatomy outside the oral cavity may be relevant for treatment, such as the position of the nose (for example, for alignment of the dental midline). In such an embodiment, an image may be cropped to include the oral cavity, including the dentition, and the nose, while removing irrelevant portions of the photo, such as those containing the eyes, ears, chin, etc.

In some embodiments, cropping may include removing columns and/or rows of pixels in an image. For example, some algorithms and methods herein may be trained or expect images having a particular aspect ratio. In some embodiments, cropping may include changing an aspect ratio of the image from a first aspect ratio to a second aspect ratio by removing portions of the image, such as the top and/or bottom of the image (rows of pixels) or the left and/or right side of the image (columns of pixels). In some embodiments, the portions of the top and/or bottom may be removed until an aspect ratio of 2:1 is achieved, wherein the image is twice as wide as it is tall. In some embodiments, portion of the left and/or right sides of the image may be removed until an aspect ratio of 2:1 is achieved. In some embodiments, any suitable aspect ratio may be employed.

At step 2612 one or more of the systems described herein, such as the feature module 3010 of system 3000 may resize the photo. For example, to ensure a uniform photo size for analysis and/or to position the patient's dentition in approximately a similar location within the photos, the cropped photo may be resized. For some photo capture modes (e.g., photo tube mode), the cropped photo may require padding in order to produce the desired size. For example, the cropped photo may be padded based on a 2:1 ratio.

At step 2614 one or more of the systems described herein may perform additional checks. The checks may be checks that detect the quality of the image, the anatomy captured in the image, and/or the state of the anatomy in the image, among other things to test whether the image satisfies any requirements, as described herein and below. For example, the various classifications (e.g., binary classifications 224 and/or categorical classifications 226) and/or requirements (e.g., requirements 234) described herein (e.g., with respect to FIG. 3) may be checked to ensure clinically relevant photos. In some embodiments, the checks may be image analysis based checks without without the assistance of AI/ML based checks.

At step 2616 one or more of the systems described herein may determine whether the photo passed the checks. For example, as described herein, AI module 208 and/or requirements module 210 may determine whether the various classifications and/or requirements have been satisfied. In one example, requirements module 210 may determine requirements 234 that may be customized for a particular patient at a particular state of treatment. For example, requirements module 210 may analyze patient data 136 and/or treatment data 138 to determine requirements 234. Patient data 136 may indicate patient-specific circumstances which may affect requirements 234. For example, patient data 136 may indicate that the patient is missing certain teeth such that requirements 234 may not require visibility of teeth that are known to be missing and therefore not visible.

Requirements 234 may include, for instance, visibility of a particular body part, visibility of a particular appliance, type of view captured, etc. The particular body part may correspond to a tooth of interest identified from the current state of treatment plan. For example, patient data 136 and/or treatment data 138 may indicate significant movement for a certain tooth. The particular body part may further correspond to one or more teeth near the tooth of interest. For example, if significant movement is expected for a certain tooth, the neighboring teeth may be of interest.

In some examples, the diagnosis may require the patient to wear an appliance. For example, the patient may be required to wear a cheek retractor to properly expose the patient's teeth for viewing. In another example, the patient may be required to wear an orthodontic aligner so that the practitioner may inspect the aligner's interaction with the patient's teeth.

In some embodiments, the classification may refer to characteristics that may be defined as having one of two states (e.g., yes or no). With respect capturing images of the patient's detention, examples of binary classifications may include, without limitation, whether a particular tooth is visible, whether an upper jaw is visible, whether a lower jaw is visible, whether an appliance or assistive device (e.g., an aligner, a cheek retractor, etc.) is visible, whether a focal distance threshold—corresponding to whether an entirety of the body part is visible—is satisfied, whether upper and lower teeth contact, whether a lighting threshold is satisfied, whether a localized calculus (e.g., plaque buildup) is present, and whether a gingival recession is present.

In some embodiments, the AI model may return a metric that estimates how much the mouth is open, instead of a binary yes or no for openness. In some embodiments, the model may return the amount of tooth or jaw that is visible, the extent to which an assistive device is used (e.g., how far a cheek is retracted or how much additional retraction is desired to capture the dentition), how close the focus is to a focal distance threshold, how much above or below the lightning is to a lighting threshold, the amount of localized calculus is present or how much a gingiva is recessed. In some embodiments, each doctor can individually preset their own particular thresholds for one or more requirements, such as how open the mouth should be, to satisfy their unique requirements for their practice.

At step 2618 one or more of the systems described herein may capture the photo. For example, if the AI/ML based checks have all passed, the cropped and optionally padded photo may be captured. Based on the capture order, method 2600 may return to step 2602 to capture the next photo.

FIG. 29 is a flow diagram of an exemplary computer-implemented method 2900 for multi mode AI based photo guidance, which in some embodiments may be an alternative to the methods described herein (e.g., method 500). The steps shown in FIG. 29 may be performed by any suitable computer-executable code and/or computing system, including the system(s) illustrated in FIGS. 1 and 2. In one example, each of the steps shown in FIG. 29 may represent an algorithm whose structure includes and/or is represented by multiple sub-steps, examples of which will be provided in greater detail below.

As illustrated in FIG. 29, at step 2902 one or more of the systems described herein may determine a photo capture mode for capturing a plurality of clinically relevant photos of a person's dentition satisfying clinically acceptable positions and a plurality of clinically acceptable orientation of teeth relative to a camera. For example, guidance module 3008 may display guidance prompts 3028 based on a determined by the feature module 3010 from facial detention or absence thereof of an assistant, detection of absence of an assistive device detection, and/or usage of the front or back camera to image the patient's detention as, for example, determined by the AI module, which may be based on binary or categorical classifications.

In some examples, determining the photo capture mode may include detecting, by the AI module 3006, a presence of a photo tube device in the image data 3032 of the image data stream 3022. For example, detecting the presence of the photo tube device may include capturing an initial photo (e.g., image data stream 222 or image data stream 3022, which may be the same) and identifying the photo tube device in the initial photo. In some examples, detecting the presence of the photo tube device comprises receiving a user indication of the photo tube device. In some examples, detecting the presence of the photo tube device may include detection using trained artificial intelligence, such as machine learning or a neural network (e.g., a convolutional neural network, a generative adversarial network). As described above, a patient may have a device, such as a smartphone, that is capable of taking photos. The smartphone may be provided a previously trained neural network that may assist the patient in taking clinically relevant photos.

A neural network may be used to detect the existence of a photo tube. The neural network may undergo training using training data in order to recognize the presence or absence of the photo tube and classify the image. A neural network may determine categorical classifications, which may correspond to categorical classifications 226. The training may include training with labeled images including a photo tube. The labels may include a bounding box labeled as containing a photo tube.

In some examples, semantic segmentation may be performed using machine learning. For example, a neural network or other machine learning scheme may be used to perform semantic segmentation to separately identify the photo tube. In some examples, a neural network may be trained to perform semantic segmentation by inputting an image data set, such as a training data set, for semantic segmentation by the neural network. This training data set may have a corresponding mask data set of the desired semantic segmentation. The training may further include computing an error between an output of the neural network (e.g., by performing the semantic segmentation) and the mask data set corresponding to the image data set and adjusting the parameters of neural network to reduce the error.

In some examples, determining the photo capture mode may include detecting, by the AI module 3006, a presence of a cheek retractor in the image data 3032 of the image data stream 3022. For example, detecting the presence of the cheek retractor may include capturing an initial photo (e.g., image data stream 222 or image stream 3022, which may be the same) and identifying the cheek retractor in the initial photo. In some examples, detecting the presence of the cheek retractor may include receiving a user indication of the cheek retractor. In some examples, detecting the presence of the cheek retractor may include detection using trained artificial intelligence, such as machine learning or a neural network. As described above, a patient may have a device, such as a smartphone, that is capable of taking photos. The smartphone may access a previously trained neural network (e.g., by connecting to a remote server, by accessing its own local storage) that may assist the patient in taking clinically relevant photos.

A neural network may be used to detect the existence of a cheek retractor. The neural network may undergo training using training data in order to recognize the presence or absence of the cheek retractor and classify the image. A neural network may determine categorical classifications, which may correspond to categorical classifications 226. The training may include training with labeled images including a cheek retractor. The labels may include a bounding box labeled as containing a cheek retractor.

In some examples, semantic segmentation may be performed using machine learning. In semantic segmentation, pixels in an image, usually all pixels in an image, are labeled with a class label, such as gingiva, cheek, tooth, assistive device, etc. For example, a neural network or other machine learning scheme may be used to perform semantic segmentation to separately identify the cheek retractor. In some examples, a neural network may be trained to perform the semantic segmentation by inputting an image data set, such as a training data set, for semantic segmentation by the neural network. This training data set may have a corresponding mask data set of the desired semantic segmentation. The training may further include computing an error between an output of the neural network (e.g., by performing the semantic segmentation) and the mask data set corresponding to the image data set and adjusting the parameters of neural network to reduce the error. While reference herein is made to semantic segmentation, in some examples, in addition to or alternatively to the semantic segmentation described herein, other types of image segmentation may be performed to identify and/or classify different objects in an image. For example, the system may use panoptic segmentation, instance segmentation, and/or any other suitable image segmentation methods.

In instance segmentation, in addition to classifying each pixel in the image, each instance of the same class of object may be distinguished from each other instance of an object in the same class. For example, each tooth, jaw and/or assistive device may be separately identified.

Panoptic segmentation may include assigning each pixel in an image with a class and an instance, allowing for each tooth to be separately classified and distinguished from each other tooth and/or for each jaw or assistive device to be similarly separately classified and distinguished.

In some examples, determining the photo capture mode may include detecting no presence, such as the absence, of an assistive device. For example, detecting no presence of the assistive device may include capturing an initial photo (e.g., image data stream 222) and identifying no assistive device in the initial photo for failing to identify an assistive device in the initial photo. In some examples, detecting no presence of the assistive device may include receiving a user indication of no assistive device.

In some examples, determining the photo capture mode may include detecting a presence or absence of an assistive device based on a presence or absence of a color within the image. For example, in some embodiments, an assistive device may be of a particular color. The system may detect an amount of the particular color within the image data 3032 of the image data stream 3022. If the amount of the particular color is above a particular threshold, then the assistive device may be determined to be present and if below a threshold then the assistive device may be determined to not be present. Alternatively, in some examples, the assistive device may be determined to be present if the amount of the particular color is above a threshold. The threshold may be a number of pixels in the image that are the particular color. In some embodiments, the threshold may be a percentage of pixels in the image that are of the particular color.

In some examples, determining the photo capture mode may include detecting a presence or absence of a bar code, such as a one-dimensional or two-dimensional bar code that is part of the assistive device. For example, in some embodiments, the system may detect a barcode within the image data 3032 of the image data stream 3022. If the barcode matches a predetermined barcode, such as a barcode stored within a datastore 120, then the assistive device may be determined to be present. If no barcode is detected or a barcode that does not match a predetermined barcode, then the assistive device may be determined to not be present. In some examples, the determination may include detecting a presence of a feature of the assistive device (e.g., a shape of a structure) or an absence of a feature (e.g., the lack of a lip region in the image in the case where the assistive device is configured to retract the lip region).

In some examples, determining the photo capture mode may include detecting an assisted mode. For example, detecting the assisted mode may include capturing a front initial photo with a front camera and a back initial photo with a back camera (e.g., image data stream 222) and detecting, for example using the AI module with a trained face detection neural network, a first person in the front initial photo and a second person in the back initial photo, based on, e.g., differences in facial features or other features (e.g., clothing, accessories, lighting). For example, the first person may be a person assisting the patient (the second person) by capturing images using the back camera. In this example, the person assisting the patient may be facing the front camera while capturing the images with the back camera. In some examples, detecting the assisted mode may include receiving a user indication of the assisted mode. In some examples, detecting the presence of one or more people, faces, or dentition may include detection using trained artificial intelligence, such as machine learning or a neural network. As described above, a patient may have a patient system, such as a smartphone or tablet, that is capable of taking photos. The patient system (e.g., smart-phone, tablet) may access a previously trained neural network that may assist the patient in taking clinically relevant photos.

A neural network may be used to detect the existence of one or more people, faces, or dentition. The neural network may undergo training using training data in order to recognize the presence or absence of the one or more people, faces, or dentition and classify the image. A neural network may determine categorical classifications, which may correspond to categorical classifications 226. The training may include training with labeled images including a one or more people, faces, or dentition. The labels may include a bounding box labeled as containing one or more people, faces, or dentition.

In some examples, semantic segmentation may be performed using machine learning. For example, a neural network or other machine learning scheme may be used to perform the semantic segmentation to separately identify the one or more people, faces, or dentition. In some examples, a neural network may be trained to perform the semantic segmentation by inputting an image data set, such as a training data set, for semantic segmentation by the neural network. This training data set may have a corresponding mask data set of the desired semantic segmentation. The training may further include computing an error between an output of the neural network (e.g., by performing the semantic segmentation) and the mask data set corresponding to the image data set and adjusting the parameters of neural network to reduce the error.

In some examples, the photo capture mode may designate a front camera as a default camera for capturing the plurality of clinically relevant photos. For example, a retractor mode or a no device mode (when unassisted) may designate the front camera as described herein. In some examples, the default setting may be overridden, e.g., if the patient is using a reflective surface such as a mirror.

In some examples, the photo capture mode may designate a back camera as a default camera for capturing the plurality of clinically relevant photos. For example, a photo tube mode, a retractor mode (when assisted) and/or a no device mode (when assisted) may designate the back camera as described herein. In some examples, the default setting may be overridden, e.g., if the back camera is having issues, or if the front camera is somehow better than the back camera.

In some examples, the photo capture mode may designate a capture order, specifying an order in which different views are to be captured. For example, the capture order may specify capturing in order a right view, a center view, and a left view. In other examples, the capture order may specify capturing in order a center view, a right view, and a left view. Other examples of capture order may include any other combination and/or order of views.

At step 2904 one or more of the systems described herein may determine, based on the photo capture mode, one or more photo parameters to define the clinically acceptable criteria. For example, requirements module 210 may determine requirements 234.

At step 2906 one or more of the systems described herein may provide, in response to the one or more photo parameters, automated instructions for capturing the plurality of clinically relevant photos. For example, guidance module 208 may provide and/or update in real-time guidance prompts 228 as described herein.

In some examples, the automated instructions may include instructions for the capture order. For example, the automated instructions may include instructions for the current view of the capture order and may further provide instructions following the capture order.

In some examples, providing the automated instructions may include mirroring the automated instructions for display. For example, as described herein, when an unassisted patient is facing away from the display (e.g., using the back camera) the instructions may be mirrored.

At step 2908 one or more of the systems described herein may preprocess preliminary photos from the camera in response to the automated instructions. For example, one or more of AI module 206, guidance module 208, and/or requirements module 210 may preprocess image data stream 222 from camera 132 of system 102 and/or another camera in communication with system 200.

In some examples, preprocessing the preliminary photos may include detecting whether the preliminary photos satisfy the one or more photo parameters, as described herein. In some examples, preprocessing the preliminary photos may include cropping the photo tube device from the preliminary photos. Cropping may include removing, by cropping, portions of the image that are not clinically relevant. In some embodiments, cropping may include removing columns and/or rows of pixels in an image. In some embodiments, cropping may include changing an aspect ratio of the image from a first aspect ratio to a second aspect ratio by removing portions of the image, such as the top and/or bottom of the image (rows of pixels) or the left and/or right side of the image (columns of pixels). In some embodiments, the portions of the top and/or bottom may be removed until an aspect ratio of 2:1 is achieved, wherein the image is twice as wide as it is tall. In some embodiments, portion of the left and/or right sides of the image may be removed until an aspect ratio of 2:1 is achieved. In some embodiments, any suitable aspect ratio may be employed.

In some examples, preprocessing the preliminary photos may include detecting a face in the preliminary photos. In some examples, preprocessing the preliminary photos may include detecting a facial landmark in the preliminary photos. For instance, the facial landmark may correspond to a mouth and preprocessing the preliminary photos may further include cropping around the detected mouth in the preliminary photos.

In some examples, preprocessing the preliminary photos may include resizing the preliminary photos. In some examples, preprocessing the preliminary photos may include padding the preliminary photos. For example, the padding may include adding rows or columns of pixels to the increase or decrease the height or width of the image so that is corresponds to a 2:1 aspect ratio.

At step 2910 one or more of the systems described herein may capture, using the camera based on the preprocessed preliminary photos, the plurality of clinically relevant photos. For example, camera module 204 may save image data stream 222 as image data 232.

In some examples, capturing the plurality of clinically relevant photos may further include capturing, using the preprocessed preliminary photos in response to satisfying the clinically acceptable criteria, the plurality of clinically relevant photos.

Although method 2900 is presented as a sequence of steps, in some examples, the steps of method 2900 may be repeated as needed to provide continuous feedback until the desired images are captured. Thus, certain steps may be repeated, and requirements 234 and/or guidance prompts 228 may be continuously updated until image data 232 is sufficiently captured.

With reference to FIG. 1, in some embodiments, the elements of the system 100 (e.g., the virtual dental care modules 108 and/or the virtual dental care datastore(s) 120) may be operative to provide multi mode AI based image capture aid in taking images relevant to virtual dental care using the camera 132 on the dental patient system 102. An example of how the elements of the system 100 may operate to provide intelligent photo guidance is shown in FIG. 1F.

At an operation 195a, the virtual dental care system 106 may provide photo capture mode data to capture clinically relevant photos of a user. "Clinically relevant photos," as used herein, may include images that represent the state of dental conditions in a patient's dentition. Clinically relevant photos may include photos that are sufficient to provide current position(s) and/or orientation(s) of the teeth in a patient's mouth. Examples of clinically relevant photos include photos that show all the teeth in a patient's arch; photos that show the shape of a patient's arch; photos that show locations of teeth that are missing, supernumerary, ectopic, etc.; photos that show malocclusions in a patient's arch (e.g., from front, left buccal, right buccal, and/or other various perspectives); etc. "Photo capture parameters," as used this context, may include parameters to define the assistive device used to take the photos (or lack of such assistive device), the camera location used to take the photos, such as a camera on a front side of a device or a back side of a device. In some embodiments, a front side of a device may be a side of a device with a screen and a back side of a device may be a side of a device opposite the side with a screen or a side without a screen. Photo capture parameters may also include whether or not the user is assisted by another or a second person. Photo parameters may also include features of a photo capture mode, such as face detection of the patient and/or a person assisting the patient. Features may also include whether a written instruction, or other visual guidance is mirrored on a display or not. Features may also include image preprocessing, such as resizing and padding or the image. Features may also include the capture order of the dentition images, such as the order in which the center, right, and left photos are taken.

At an operation 195b, the virtual care dental system 106 may send the photo capture mode data to the dental patient system 102. This operation can occur as a file and/or data transfer over the computer-readable medium 104.

At an operation 195i, the dental patient system 102 may use the photo capture mode data and, for example, the image data stream, to determine the photo capture mode.

At an operation 195c, the dental patient system 102 may use the one or more photo parameters to intelligently guide the user, such as the patient and/or a person assisting the patient to capture clinically relevant photos of their dentition based on the AI module 3006, as discussed herein. For example, the AI module may detect the presence or absence of an assistive device and/or the presence or absence of one or more faces in the front and/or rear camera. The dental patient system 102 may determine the photo preprocessing parameters, such as padding and cropping of the captured image. As noted herein, the operation 195c may be performed by automated agents and without human intervention.

At an operation 195d, the dental patient system 102 may operate to capture clinically relevant photos using the guidance. In some implementations, a patient may follow instructions to capture photos of their dentition using the intelligent guidance provided on the dental patient system 102. In various implementations, at least a part of operation 195d is performed by automated agents that configure a camera to take photos without human intervention. At an operation 195e, the dental patient system 102 may send captured clinically relevant images to the virtual dental care system 106. This operation may occur as a file and/or data transfer over the computer-readable medium 104.

At an operation 195f, the virtual dental care system 106 may store the captured clinically relevant photos. In various implementations, the virtual dental care system 106 may store the captured clinically relevant photos in a treatment database associated with a patient, a clinical data file associated with a patient, and/or in any relevant datastore. At an operation 195g, the virtual dental care system 106 may send captured clinically relevant photos to the dental patient system 102 and/or the dental professional system 150. This operation may occur over a file and/or data transfer over the computer-readable medium 104.

At an operation 195h, the dental patient system 102, the virtual dental care system 106 and/or the dental professional system 150 may use clinically relevant photos for virtual dental care. As an example, the dental professional system 150 may display to the patient instructions in the form of an overlay over an image of the patient's teeth. As another example, the dental professional system 150 may display to the patient verbal and/or interactive instructions on how to modify and/or improve capture of a clinically relevant photo. In some implementations, the dental patient system 102, the virtual dental care system 106 and/or the dental professional system 150 may, e.g., use clinically relevant photos for image-based assessments, intelligent patient guidance, and/or photo-based refinements. In some embodiments, the steps performed by the virtual dental care system 106 may be performed by the dental professional system 150, such that the virtual dental care specified in step 195h may be enabled by the dental professional system 150 and the patient system 102 without requiring a separate virtual dental care system 106.

As described above, the dental patient system 102 may be a device such as a smartphone that is capable of taking photos. The smartphone may access a previously trained neural network that may assist the patient in taking clinically relevant photos. The patient may also use an assistive device and/or have assistance in taking the photos. The patient may be provided customized guidance to ensure the photos satisfy clinical requirements. The requirements may be customized to the patient at that particular stage of the patient's treatment. Thus, the patient's doctor may be able to remotely view the patient to track the patient's progress, update the treatment, or diagnose any issues.

Dental Image Quality Assessment

Images, such as dental images, are widely used in the formation and monitoring of a dental treatment plan. For example, some dental images may be used to determine a starting point of a dental treatment plan, or in some cases determine whether a patient is a viable candidate for any of a number of different dental treatment plans. In some examples, various quality aspects of the dental images may affect their ability to be used for dental monitoring, recommendations and/or treatment planning. Some quality aspects may seem subjective and conventionally require manual (e.g., human) inspection and approval of a dental image prior to use for dental treatment planning.

Described herein are apparatus (e.g., systems and devices, including software) and methods for training and applying a machine learning agent (e.g., a neural network, such as neural network 406 and those described elsewhere herein) to generate a score of image quality of an image. This image quality score may be used to determine whether the image has sufficient quality for use with dental monitoring, recommendations and/or dental/orthodontic treatment planning (generically and collectively referred to herein as "treatment planning").

The disclosed methods and systems also enable the provision of real-time image quality assessment, enabling a faster, more effective photo capture experience. For example, the quality of the photo may be assessed in real time based on clinically relevant factors, if the quality is low, the user would be prompted in real time to take an adjusted photo. Real-time assistance allows for the capture of better photographs, thereby improving patient treatment and monitoring (e.g., enabling improved and earlier detection of issues, thus enabling corrective measures) and resulting outcomes. Real-time assistance also improves efficiency of treatment monitoring. For example, by intelligently evaluating and assisting in photo capture, the need to take multiple photographs or additional photographs (e.g., in the event that an initial set of photographs proves unsatisfactory following evaluation by a dental professional) may be reduced.

In some examples, as may be made clear by the context, treatment planning may comprise generating a series of incremental stages for moving the patient's teeth to correct malocclusions or for other therapeutic and/or cosmetic reasons. The training of the machine learning agent may include obtaining or accessing training images that have been arranged into sub-groups. The images with the sub-groups may be ranked and/or labeled based on their image quality. The ranking and/or labeling may be performed by one or more scorers (e.g., human scorers) that apply their potentially subjective determination of the relative quality of the images in the sub-group. These relative determinations may account for aspects of an image that are specific to the intended task, e.g., the use of the image for treatment planning, or may be more general. The training images may be masked so that the scorers are comparing a particular region or aspect of the training images (e.g., teeth, teeth and gingiva, sub-sets of the teeth, subsets of teeth and gingiva, lips, etc.). The same masking may be applied to the image(s) to be assessed.

Application of the trained neural network, e.g., to assess image quality of a dental image for example, may be performed on a portable or mobile device such as a smartphone, tablet computer, laptop computer or the like. For example, the trained neural network may be stored and executed from within a memory of the portable or mobile device such as patient system 102 or computing system 1910. In some examples, the trained neural network may be stored remotely and accessed and executed through any feasible network, including the Internet, such as described with respect to FIGS. 19 and 20.

Figure 31:
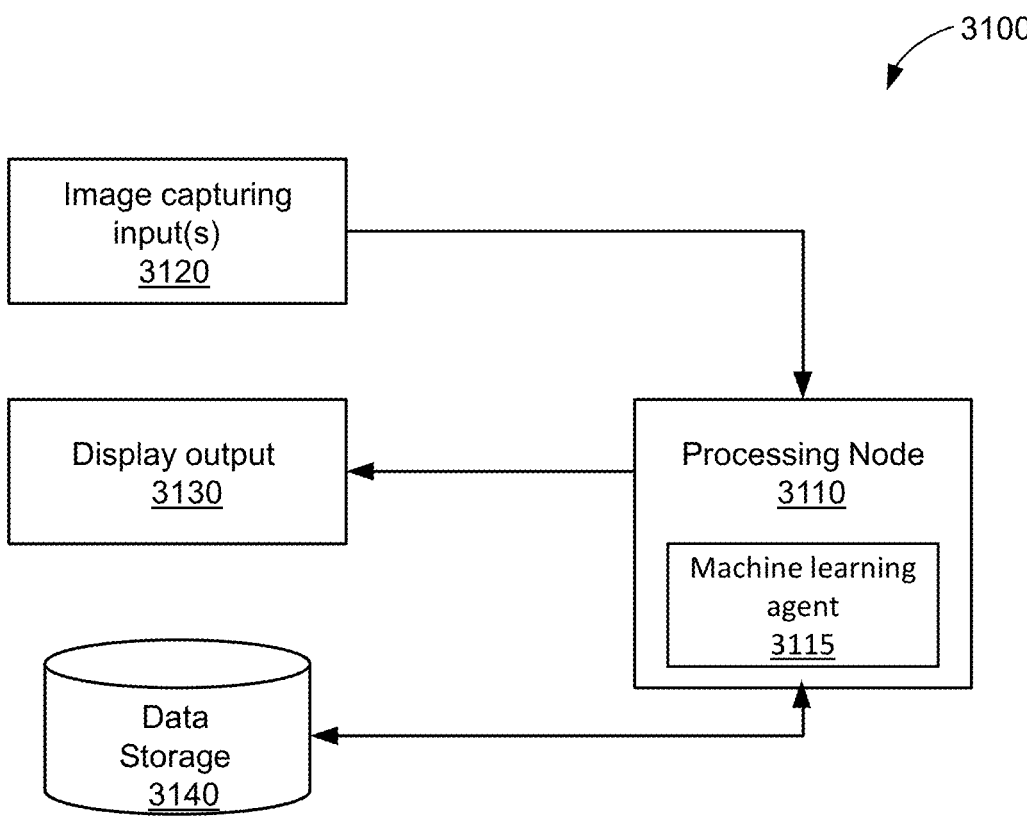
FIG. 31 shows a block diagram of an example machine-learning image quality assessment apparatus, in accordance with some embodiments.

FIG. 31 schematically illustrates one example of a machine-learning image quality assessment apparatus 3100. Although described herein as a system, the machine-learning image quality assessment apparatus 3100 may be realized with any feasible apparatus, e.g., device, system, etc., including hardware, software, and/or firmware, such as the patient system 102, dental professional system 150, virtual dental care system 106, system 200, system 3000, device 3600, or as shown and described with respect to FIGS. 19, 20. In some examples the machine-learning image quality assessment apparatus 3100 may include a processing node 3110, an image capturing input and/or device 3120, a display output and/or device 3130, and a data storage 3140. As shown, the image capturing input 3120, the display output 3130, and the data storage 3140 may each be coupled to the processing node 3110. In some examples, all components of the machine-learning image quality assessment apparatus 3100 may be realized as a single device (e.g., within a single housing). In some other examples, components of the machine-learning image quality assessment apparatus 3100 may be distributed within separate devices. For example, the coupling between any two or more devices, nodes, and or data storage (which may be referred to herein as modules) may be through a network, including the Internet such as shown and described with respect to FIGS. 19 and 20. In some examples, the machine-learning image quality assessment apparatus 3100 may be a cloud-based apparatus. In some examples one or more components of the machine-learning image quality assessment apparatus 3100 may be cloud-based modules coupled together through any feasible wired or wireless network, including the internet.

The image capturing input 3120 may include one or more image capturing devices that capture optical images of a patient's teeth (sometimes referred to herein as a subject's dentition). In some examples, the image capturing input 3120 may include a white light, near infrared light, ultra-violet light, and/or fluorescence light sources and sensors. In some other examples, the image capturing input 3120 may capture x-ray images, video images, panoramic dental scan image, stitched together images, or the like. The image capturing input may be configured to receive an image (or multiple images) from an image capture device (e.g., camera, scanner, etc.). In some examples, the image(s) may be from a patient system 102 (e.g., a smartphone, a tablet, a portable scanner). In other examples, the images may be from a device associated with a dental professional system 150 (e.g., an intraoral scanner).

The display output 3130 may be any feasible image display output, such as display device 1924. In some examples, the display output 3130 may be an integral part of the machine-learning image quality assessment apparatus 3100 and be integrated into a common housing or case. In other examples, the display output 3130 may be communicatively coupled to the machine-learning image quality assessment apparatus 3100 through, for example, wired or wireless connections. In some cases, the display output 3130 may include or may be configured to communicate with a computer monitor, tablet device, mobile phone, or the like. The display output 3130 may be used to display image data, such as image data collected by the image capturing input 3120. Alternatively, or in addition, the display output 3130 may provide image quality assessment information regarding a captured image. For example, the display output 3130 may indicate whether the captured image is clear and/or of sufficient quality or is of insufficient quality with respect to using the captured image with or for a dental treatment plan.

The data storage 3140 may be any feasible data storage including random access memory, solid state memory, disk-based memory, non-volatile memory, and the like. The data storage 3140 may store image data, including image data captured through one or more image capturing inputs 3120.

Figure 19:
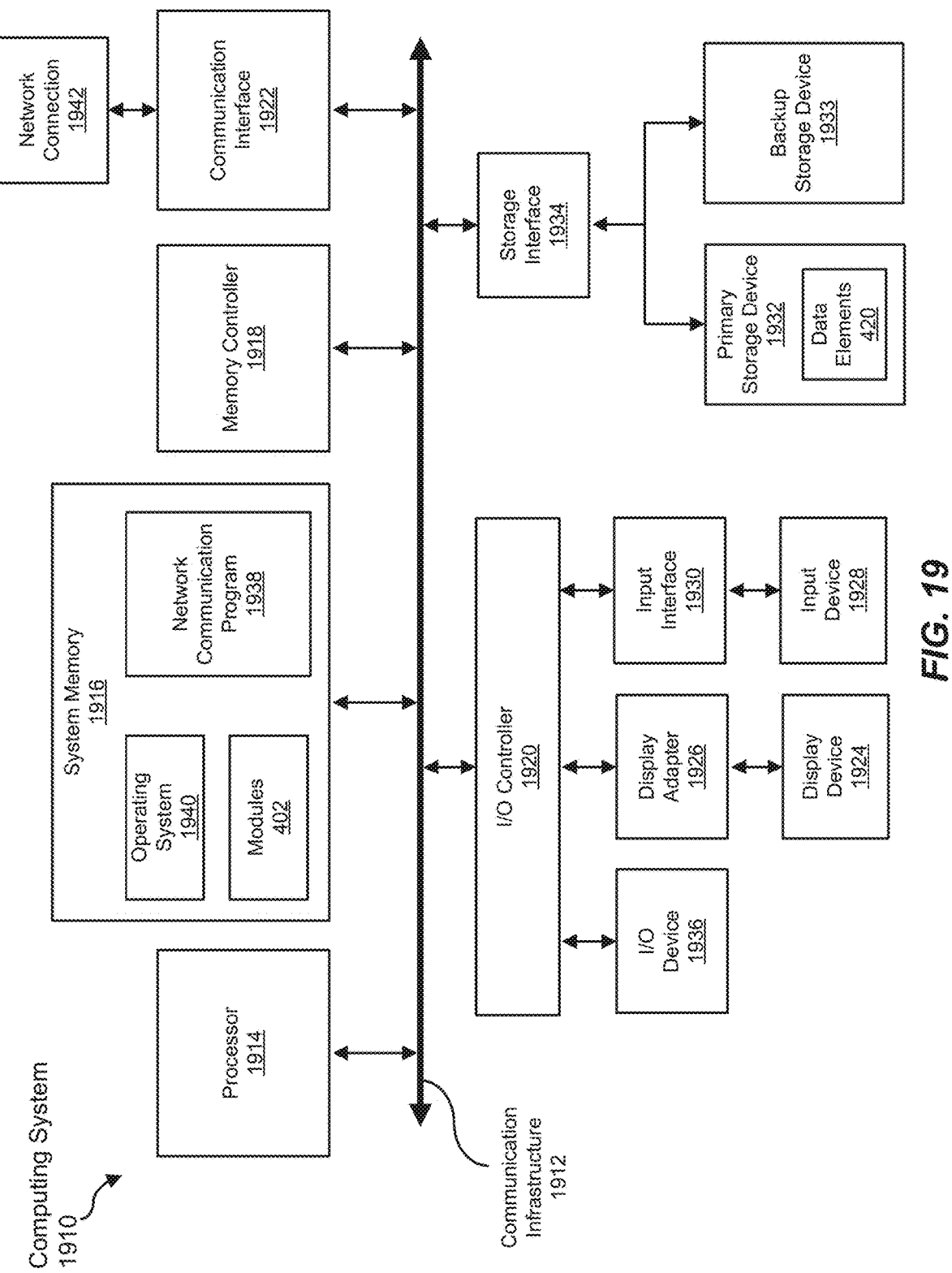
FIG. 19 shows a block diagram of an example computing system capable of implementing one or more embodiments described and/or illustrated herein, in accordance with some embodiments.
Figure 20:
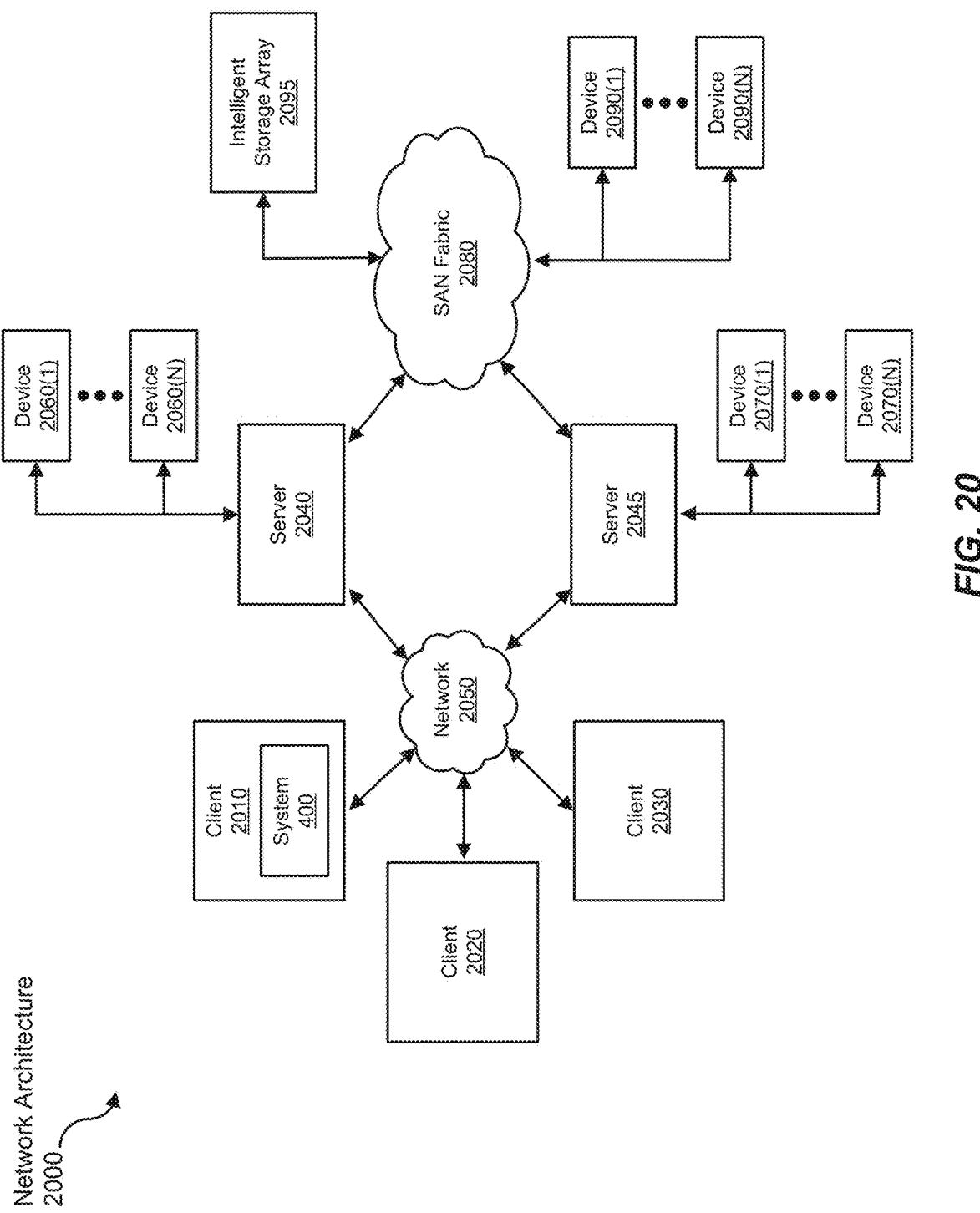
FIG. 20 shows a block diagram of an example computing network capable of implementing one or more of the embodiments described and/or illustrated herein, in accordance with some embodiments.

The data storage 3140 and/or the processing node may also include a non-transitory computer-readable storage medium that may store instructions that may be executed by the processing node 3110, such as shown and described with respect to FIGS. 19 and 20. For example, the processing node 3110 may include one or more processors, such as processors 130 and 1914 that may execute instructions stored in the data storage device 3140 to perform any number of operations including processing image data from the image capturing input 3120 and generating a quality assessment of any captured image. For example, the data storage 3140 may store one or more neural networks that may be trained and/or executed by the processing node 3110. Alternatively, the processing node may include one or more machine-learning agents (e.g., trained neural networks, as descried herein) 3115, as shown in FIG. 31.

In some examples, the data storage 3140 may include instructions to train one or more neural networks to assess image quality of dental images. The assessed image quality may simultaneously reflect a plurality of image quality aspects including, but not limited to, blurriness, darkness, fogginess, and visibility of teeth. More detail regarding training of the neural network is described below in conjunction with FIGS. 32-34. Additionally, or alternatively, the data storage device 3140 may include instructions to execute one or more neural networks to assess the image quality of dental images. More detail regarding the execution of a neural network is described below in conjunction with FIG. 35.

FIG. 32 is a flowchart showing an example method 3200 for training a neural network to assess and/or determine an image quality of a dental image. Some examples may perform the operations described herein with additional operations, fewer operations, operations in a different order, operations in parallel, and some operations differently. The method 3200 is described below with respect to machine-learning image quality assessment apparatus 3100 of FIG. 31, however, the method 3200 may be performed by any other suitable system or device. In some examples, the neural network may be trained to determine whether an image includes sufficient image quality to be used with a dental treatment plan.

The method 3200 begins in block 3202 as the processing node 3110 collects image data, such as described herein. The image data may include dental image data (dental images), that is, images that include one or more aspects or objects of a patient's dentition. For example, the image data may include all or some of a person's teeth, face, lips, gingiva, etc. Furthermore, the teeth may include or lack one or more appliances (e.g., aligners, attachments, braces, or the like).

In some examples, the images included within the image data may be related. For example, the images may be from the same doctor, same clinic, same health organization, same geographic region, or the like. In other examples, the images included within the image data may be non-related.

Generally, the images within the image data may have a common image capture modality. For example, the image data may be all or substantially all optical images obtained from a conventional optically based camera, such as camera 132. The optical images may be captured with a digital camera, such as a cell phone camera, a laptop camera, a tablet computer camera, or the like. In another example, the images within the image data may all be panoramic or conventional x-ray images. In another example, the image data may be from a cone-bean computed tomography (CBCT) scan. In some other examples, the image data may include frames from a video, multiple frames from a video, or a composite image assembled (stitched) from a plurality of dental images or video frames. Furthermore, any and all of the image data described herein may be stored on a data storage device, such as the data storage device 3140. In some examples, the image data may include a combination of any suitable types of image data (e.g., one or more of camera, x-ray, and CBCT images and/or videos).

In some examples, the images within the image data are not normalized (e.g., resized, filtered, etc.). For example, resizing an image may artificially and/or incorrectly increase a perceived sharpness associated with the image. Thus, in such an example, non-resized images may be preferred over resized images.

In some examples, the images within the image data may be masked to highlight one or more specific dental aspects of the image. For example, the images may be masked to occlude all portions of the image except for the teeth (the dentition). In some cases, the image masking may include identifying teeth and occluding portions of the image that are not identified as teeth. In other examples, the images may be masked to show teeth and gingiva, teeth and lips, or any other feasible aspects of a dental image. Image masking may be performed by the processing node 3110 performing a segmentation algorithm or executing a neural network trained to identify and mask selectable portions of the image. One example of segmentation is described in U.S. patent application Ser. No. 17/534,420 filed Nov. 23, 2021, published as US Pat. App. Pub. 2022/0165388, which is commonly assigned, the disclosure being incorporated by reference herein in its entirety.

Next, in block 3204, the processing node 3110 forms image groups. Each image group may include two or more different images taken from the image data collected in block 3202. For example, the processing node 3110 can form any feasible number of different and distinct image groups that each include two different dental images. In other examples, the processing node 3110 can form image groups having three different dental images, four different dental images or any other number of different dental images.

Next, in block 3206, training data is generated. In some examples, the training data may be generated by a plurality of people inspecting and ranking the images based on a perceived image quality within the image groups formed in block 3204. In this manner, any number of people may be used to rank any number of images within any number of image groups.

Ranking of the images may include indicating which image, if any, has the relatively highest quality, e.g., compared to other images within the image group. In the case of an image group size of two (K=2), the ranking of the images may simplify into selecting the "best" image (image with the most perceived image quality) from the two images within the image group. In some cases, the images within the image group may be ranked based on whether the images may include sufficient image quality to be used with a dental treatment plan. The size of the sub-group (K) may be larger than 2; for example, three or more images may be co-ranked.

"Quality" may be a subjective characteristic for an image based on the scorers. A higher quality image may have more detail, better lighting, more clarity (less fuzziness and blurriness, better focus), less shadow content, etc., than a lesser quality image. However, in some examples, the training data may be ranked based on an overall perception of quality. For example, a person may use or combine any number of "quality" metrics or attributes when ranking or comparing any two (or more) pictures. Thus, as the training data is generated, the training data may encompass or include one or more quality attributes.

For example, if an image sub-group includes a first image and a second image, a person ("scorer") may review or inspect these images and determine that the first image has more perceived image quality than the second image. The person may associate ("label" or score) the first image with a first value (representing a highest perceived quality) and the second image with a second value (representing a lowest perceived quality). In some cases, the first value may be 1 and the second value may be 0. These values are exemplary, however, and any other feasible values may be used (e.g., on a scale of 1-10, 1-100, etc.). In practice, the scorer may simply indicate, relative to the other image, which of the two images is "better" than the other, or if the two images are equivalent in overall quality (e.g., within a masked region in some examples; masked-out region may be occluded from display and therefore ranking).

As mentioned, the ranking of the images may be generalized for any other feasible image group size (K>=2). For example, if the image group size includes three images (K=3), then the person ranking the images may select one of the three images has having the most perceived quality. The selected image may be labeled with a first value while the other images in the image group are labelled with a second value.

In some cases, a person may determine that the images within the image group may all have the same amount of perceived image quality. In those cases, the person may rank all the images identically. For example, the person may rank or label all images with a 1 or 0.

The processing node 3110 may train a neural network based on the training data 3208. A loss function configured to preserve a relative ranking order of the ranked sub-sets of dental images, described in greater detail below, may also be used as part of the training of the machine learning agent. In some examples, the neural network may be a fully convolutional network that examines image data by convolving image pixels with one or more predetermined convolutional filters or kernels. The neural network may be trained to indicate whether the image data is a "quality" image. In some examples, the neural network may be trained to indicated whether the image data includes sufficient image quality to be used with a dental treatment plan. The output of the neural network may be related to the training data used to train the neural network. For example, if the training data indicates or shows images with sufficient quality to be used with a dental treatment plan, then the neural network may be trained to identify images with sufficient quality to be used with a dental treatment plan. In some examples, the training data may be used to change or modify one or more of the predetermined convolutional filters or kernels through backpropagation based on an output of the loss function.

For example, an initial neural network f(x) may be expressed as equation 1 shown below:

$$f(x)=y \tag{eq. 1}$$

Where x is an array of pixels for an input image; and
y is the neural network output.

In some examples, the input to the neural network x may be a two-dimensional array of pixels. The neural network f(x) may include one or more two dimensional convolutional filters or kernels that may be used to determine y. In some cases, y may be a scalar value. In block 3206, the training data may be labelled or associated with a value based on whether or not an image is perceived to be a "quality" image. Thus, the neural network f(x) may predict or indicate a perceived image quality associated with any feasible image, including any feasible dental image. In some examples, the training image is labelled with a 1 when the training image is perceived to be a quality image and the training image is labelled a 0 when the training image perceived to not be a quality image. In a similar manner, the output of the neural network may be trained to output a value closer to 1 when the input image is a quality image and a value closer to 0 when the input image is not a quality image. Note that in some examples, the input to the neural network x may be a single two-dimensional array of pixels, when the input image is in gray scale, a stack of three two-dimensional array of pixels, when the input image is in RGB (red, green, blue) format and/or a stack of four two-dimensional array of pixels, when the input image is in RGBA (red, green, blue, alpha) format.

The loss function may be used to train the neural network. One example of an application of a loss function is described herein, however other approaches and loss functions are possible. For example, the training data may be based on an image group of size K (where K is an integer>=2). For the case of K=2, the neural network may be executed to determine an output value to indicate whether each input image is a quality image.

$$f(x_1)=y_1 \qquad \text{(eq. 2)}$$

$$f(x_2)=y_2 \qquad \text{(eq. 3)}$$

where f(x) is the function describing a neural network (equation 1);

x₁ is a first image from an image group;

$x_1$ is a first image from an image group;
$x_2$ is a second image from the image group;
$y_1$ is a first output of the neural network; and
$y_2$ is a second output of the neural network;

In one example, the loss function may be determined (computed) using one of three equations. The equation may be selected based on the ranked (labelled) image quality associated with the image group. If the image quality of the first image $x_1$ is greater than the image quality of the second image $x_2$, then the loss function may be expressed with equation 4, as shown below:

$$\text{Loss}=\max(0,\text{margin}-(y_1-y_2))^2 \qquad \text{(eq. 4)}$$

If the image quality of the second image x2 is greater than the image quality of the first image x1, then then loss function may be expressed with equation 5, as shown below:

$$\text{Loss}=\max(0,\text{margin}-(y_2-y_1))^2 \qquad \text{(eq. 5)}$$

If the image quality of the first image x1 is similar to the image quality of the second image x2, then the loss function may be expressed with equation 6, as shown below:

$$\text{Loss}=\max(0,\text{abs}(y_1-y_2)-\text{margin})^2 \qquad \text{(eq. 6)}$$

In the equations 4-6, "max" is a maximum value function and "margin" is a predefined constant. The margin constant is used within the loss function to describe a difference value within which two images have the same quality (e.g., level of quality). For example, if margin=0.1, then a difference in neural network predictions between $y_1$ and $y_2$ that is <=0.1 would indicate that the quality, as determined by the neural network, of the two images is approximately the same. The output of the loss function may be used (backpropagated) to train the neural network. For example, the output of the loss function may be used to modify one or more of the convolutional filters or kernels so that the neural network may more accurately predict or identify a "quality" image. These predicted or identified images may have sufficient quality to be used for determining or modifying dental monitoring, recommendations and/or treatment planning.

Figure 33A:
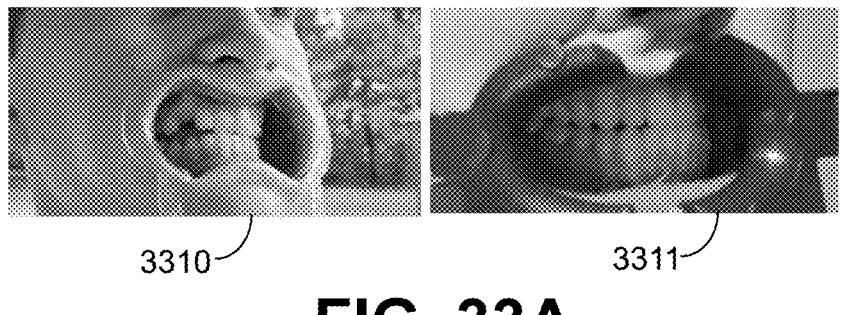
FIGS. 33A, 33B, and 33C shows example images that may be used for training data, in accordance with some embodiments.
Figure 33B:
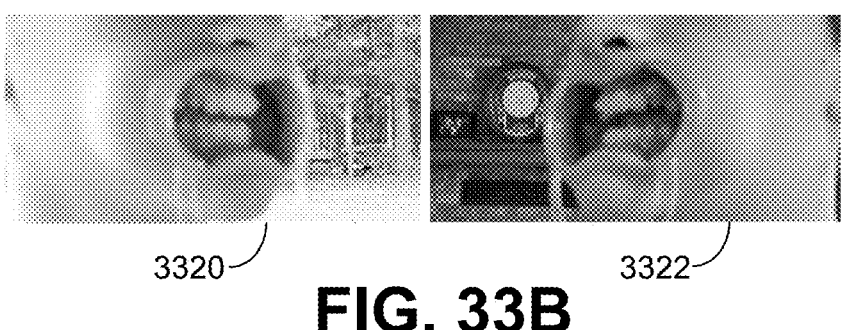
Figure 33C:
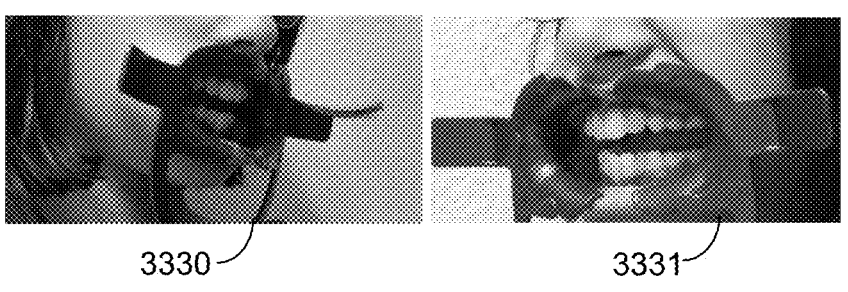

FIGS. 33A-33C shows example sub-sets (e.g. pairs) of images that may be used for training data. FIG. 33A shows a first example image sub-set (K=2) with a first image 3310 and a second image 3311. The first image 3310 may have the highest perceived image quality of the images within the first example image group. For example, the second image 3311 may include too many shadows, or may have poor lighting. Thus, when ranked, a person may rank the first image 3310 over the second image 3311. Accordingly, in some examples the first image 3310 may be labelled with a 1 and the second image 3311 may be labelled with a 0.

FIG. 33B shows a second example image group with a first image 3320 and a second image 3321. In this example, both the first image 3320 and the second image 3321 may be perceived to have a similar image quality. Thus, when ranked, a person may rank the first image 3320 as similar to the second image 3321. Accordingly, in some examples the first image 3320 and the second image 3321 may both be labelled with a 0. In some other examples, the first image 3320 and the second image 3321 may both be labelled with a 1.

FIG. 33C shows a third example image group with a first image 3330 and a second image 331. In this example, the second image 331 may be perceived to have the highest perceived image quality of the images within the third image group. For example, the first image 3330 may be too dark or may not show enough dentition detail. Thus, when ranked, a person may rank the second image 3331 over the first image 3330. Accordingly, in some examples the first image 3330 may be labelled with a 0 and the second image 3331 may be labelled with a 1.

Figure 34A:
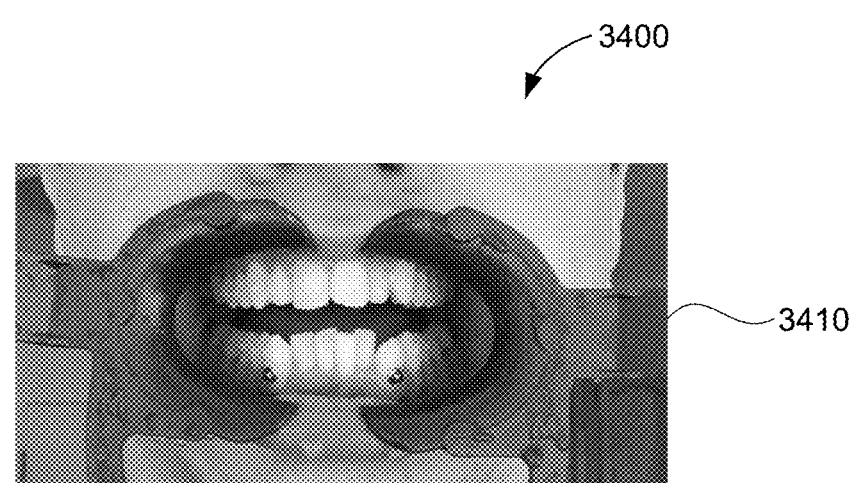
FIGS. 34A and 34B shows an example of a dental image without (FIG. 34A) and with (FIG. 34B) a mask selective for the teeth, in accordance with some embodiments.
Figure 34B:
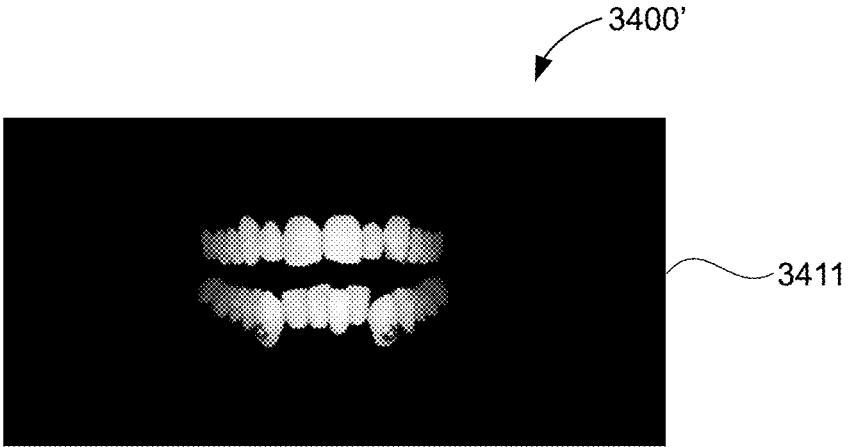

FIGS. 34A-34B shows example of a dental image 3400, 3400'. The image 3410 in FIG. 34A shows an example of an optical image capture of a subject's dentition. The image also includes facial structures and a mouth prop (cheek retractor) 3410. In some cases, it may be desirable to focus only on all or portion of the dentition in an image, such as the patient's teeth. The first image may be masked 3411 to generate a masked image 3400'. The mask may occlude or hide non-dental (non-teeth) features within the image. Thus, the mask may identify any feasible region of interest. In some examples, the mask may be determined or generated by a processor executing a segmentation algorithm or a neural network trained to identify dental features within an image.

Figure 35:
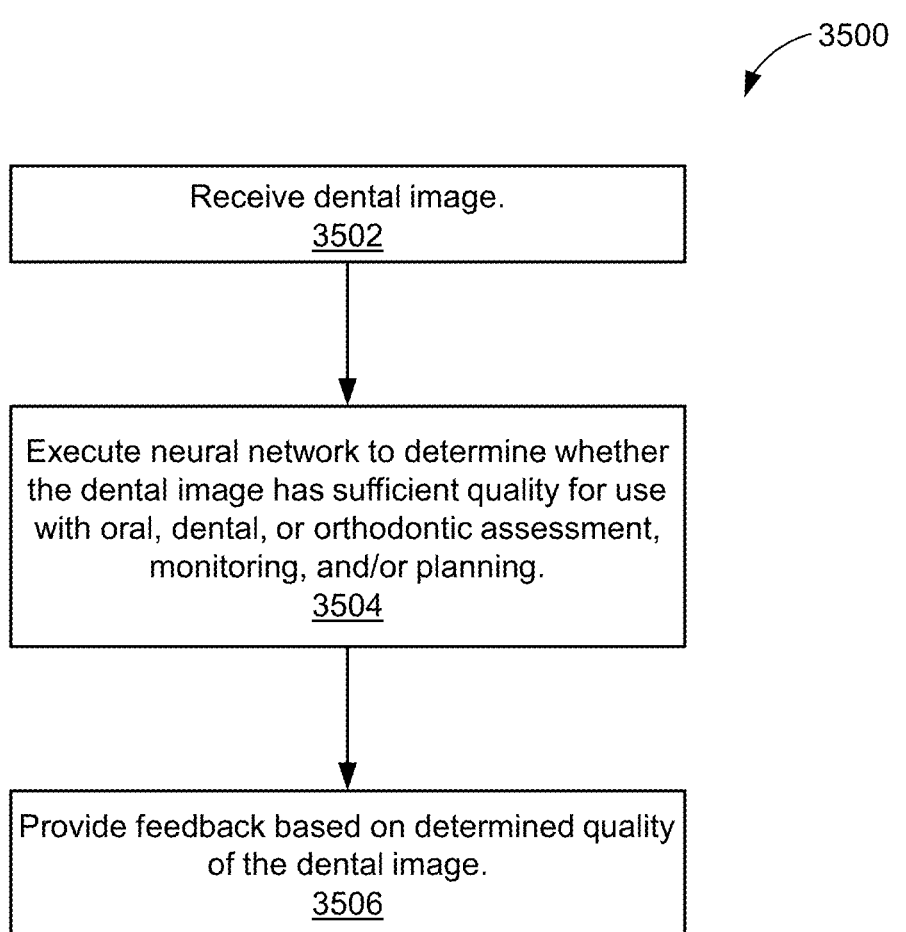
FIG. 35 is a flowchart showing an example method for assessing the image quality of a dental image, in accordance with some embodiments.

FIG. 35 is a flowchart showing one example of a method 3500 for assessing the image quality of a dental image. The method 3500 is described below with respect to machine-learning image quality assessment apparatus 3100 of FIG. 31, however, the method 3500 may be performed by any other suitable system or device.

The method 3500 may begin with the processing node 3110 receiving a dental image 3502. The dental image may be an optical image captured with any feasible camera, such as camera 132. Example cameras may be included with a tablet computer, cell phone, laptop computer, or any other feasible imaging device. In some examples, the dental image may be an x-ray image, a panoramic dental scan, or any other feasible image. In some other examples, the dental image may include frames from a video, multiple frames from a video, or a composite image assembled (stitched) from a plurality of dental images or video frames.

In some examples, the processing node 3110 and the camera may be co-located within a common housing. Thus, the processing node 3110 may be coupled to the camera within a housing. In some other examples, the processing node 3110 may access the dental image through a wired or wireless network, including the internet. Thus, the method 3500 may enable the processing node 3110 to access the dental image from a cloud-based storage device.

The processing node 3110 may execute a neural network to determine whether the dental image has sufficient quality for use with a dental treatment plan 3504. In some examples, execution of the neural network may include executing the neural network described with respect to FIG. 32. Execution of the neural network may enable the processing node 3110 to infer whether the dental image received in block 3502 includes sufficient quality as determined by the training data used to train the neural network.

Execution of the neural network may be performed by a processing node 3110 that is at least a portion of a tablet computer, a cell phone, or a laptop computer. In some examples, execution of the neural network, may be performed by a processing node 3110 separate and distinct from a tablet computer, a cell phone, or a laptop computer. Thus, execution of the neural network may be performed by a cloud-based processing node.

The processing node 3110 may provide feedback based on the determined quality of the dental image 3506. For example, if the processing node 3110 determined that the dental image is of sufficient quality, then processing node 3110 may show (display) an indication that the dental image may be used with a dental treatment plan. For example, the dental image may be used to initiate, implement, or modify a dental treatment plan. In another example, the processing node 3110 may show an indication that the dental image may not be used with a dental treatment plan. In some aspects, the processing node 3110 may inform the user to capture or take another picture to replace a previous poor quality picture.

In some examples, the processing node 3110 may track dental images captured by a particular user. If the processing node 3110 determines a user has captured several (more than a predetermined number) poor quality pictures, then the processing node 3110 may send a video or a link to a video to the user instructing or demonstrating techniques for capturing quality images.

The method 3500 may be performed entirely within a portable device, such as a cell phone, tablet computer, laptop computer, or the like. Thus, a camera of the portable device may capture a dental image, a processor of the portable device may execute a neural network to determine whether the dental image has sufficient quality for use with a dental treatment plan, and display feedback on a display of the portable device. In some instances, the processor of the portable device can display feedback within a browser window displayed on the portable device.

Figure 36:
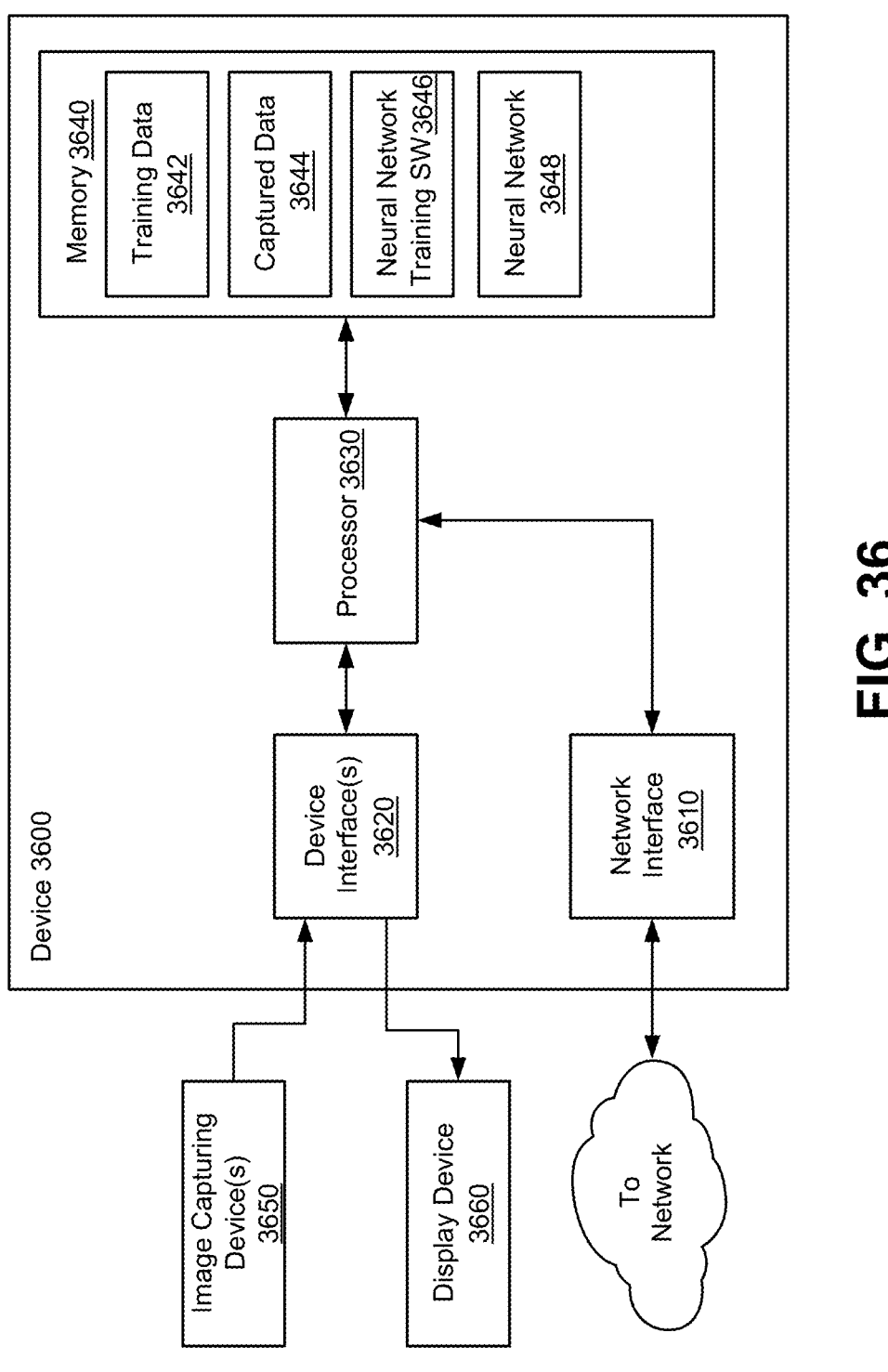
FIG. 36 shows a block diagram of a device that may be one example of the machine-learning image quality assessment apparatus of FIG. 31, in accordance with some embodiments.

FIG. 36 shows a block diagram of a device 3600 that may be one example of the machine-learning image quality assessment apparatus 3100 of FIG. 31. Although described herein as a device, the functionality of the device 3600 may be performed by any feasible apparatus, system, or method. The device 3600 may include a communication interface 3610, a device interface 3620, a processor 3630, and a memory 3640.

The communication interface 3610, which may be coupled to a network (not shown) and to the processor 3630, may transmit signals to and receive signals from other wired or wireless devices, including remote (e.g., cloud-based) storage devices, cameras, and/or displays. For example, the communication interface 3610 may include wired (e.g., serial, ethernet, or the like) and/or wireless (Bluetooth, Wi-Fi, cellular, or the like) transceivers that may communicate with any other feasible device through any feasible network.

The device interface 3620, which is coupled to the processor 3630, may be used to interface with any feasible input and/or output device. For example, the device interface 3620 may be coupled to and interface with one or more image capturing devices 3650. Example image capturing devices may include optical cameras, x-ray devices, panoramic x-ray devices, or the like. In another example, the device interface 3620 may be coupled to and interface with a display device 3660. Through the display device 3660, the processor 3630 may display images, feedback information, instructions, or the like.

In some examples, the image capturing devices 3650 and the display device 3660 may be an integral part of the device 3600. In other words, the image capturing device 3650 and the display device 3660 may share a common housing or enclosure. For example, the device 3600 may be a cell phone, a tablet computer, or a laptop computer that includes at least these elements.

The processor 3630, which is also coupled to the memory 3640, may be any one or more suitable processors capable of executing scripts or instructions of one or more software programs stored in the device 3600 (such as within memory 3640).

The memory 3640 may include training images 3642. The training images 3642 may include a plurality of images arranged into a plurality of image groups. The training images 3642 may be obtained through the communication interface 3610 and stored within the memory 3640. The training images 3642 may include images, dental images, optical images, x-ray images, panoramic images, video images, video frames, composite images formed from two or more source images, and the like. The training images 3642 may include rankings associated with images as described above with respect to FIG. 32.

The memory may include captured data 3644. The captured data 3644 may include any feasible image data, including dental image data. In some examples, the captured data 3644 may include image data captured from the image capturing devices 3650. In some other examples, the captured data 3644 may be received through the communication interface 3610 from any feasible network.

The memory 3640 may also include a non-transitory computer-readable storage medium (e.g., one or more non-volatile memory elements, such as EPROM, EEPROM, Flash memory, a hard drive, etc.) that may store a neural network training software (SW) module 3646 and a neural network 3648.

The processor 3630 may execute the neural network training SW module 3646 to train one or more neural networks to perform one or more of the operations discussed with respect to FIG. 32. In some examples, execution of the neural network training SW module 3646 may cause the processor 3630 to collect or obtain training images (such as images within the training images 3642), form image groups from the training images, generate training data from the training images, and train a neural network using the training data. In some examples, the training images 3642 may include rankings and/or labels associated with image groups. The trained neural network may be stored as the neural network 3648.

The processor 3630 may execute the neural network 3648 to determine whether an image has sufficient quality for use with a dental treatment plan. In some examples, execution of the neural network 3648 may cause the processor 3630 to perform one or more of the operations discussed with respect to FIG. 35.

Virtual Care System

FIG. 1A shows a block diagram of an example system for virtual dental care, in accordance with some embodiments. As shown in FIG. 1A, system 100 may include a dental patient system 102, a dental professional system 150, a virtual dental care system 106, and a computer-readable medium 104. The dental patient system 102, dental professional system 150, and virtual dental care system 106 may communicate to one another over the computer-readable medium 104.

Dental patient system 102 generally represents any type or form of computing device capable of reading computer-executable instructions. Dental patient system 102 may be, for example, a desktop computer, a tablet computing device, a laptop, a cellular phone such as a smartphone, an augmented reality device, or other consumer device. Additional examples of dental patient system 102 include, without limitation, servers, Personal Digital Assistants (PDAs), multimedia players, embedded systems, wearable devices (e.g., smart watches, smart glasses, etc.), smart vehicles, smart packaging (e.g., active or intelligent packaging), gaming consoles, Internet-of-Things devices (e.g., smart appliances, etc.), variations or combinations of one or more of the same, and/or any other suitable computing device. The dental patient system 102 need not be a clinical scanner (e.g., an intraoral scanner), though it is contemplated that in some implementations, the functionalities described herein in relation to the dental patient system 102 may be incorporated into a clinical scanner. As an example of various implementations, the camera 132 of the dental patient system 102 may comprise an ordinary camera that captures 2D images of the patient's dentition and does not capture height-map and/or other data that is used to stitch a mesh of a 3D surface. In some implementations, the dental patient system 102 may include an intraoral scanner (clinical or otherwise) that is capable of scanning the patient's intraoral cavity.

In some implementations, the dental patient system 102 is configured to interface with a dental consumer and/or dental patient. The terms "dental consumer," "dental patient," and "patient" may be used interchangeably herein and may include a person, such as a person seeking assessment, diagnosis, and/or treatment for a dental condition (general dental condition, orthodontic condition, endodontic condition, condition requiring restorative dentistry, etc.) and/or a person who has agreed to diagnosis and/or treatment for a dental condition. A dental consumer, a dental patient, and/or a patient, may, for instance, be interested in and/or have started orthodontic treatment, such as treatment using one or more (e.g., a sequence of) aligners (e.g., polymeric appliances having a plurality of tooth-receiving cavities shaped to successively reposition a person's teeth from an initial arrangement toward a target arrangement). In various implementations, the dental patient system 102 provides a dental consumer/dental patient with software (e.g., one or more webpages, standalone applications, mobile applications, etc.) that allows the dental patient to capture images of their dentition, interact with dental professionals (e.g., users of the dental professional system 150), manage treatment plans (e.g., those from the virtual dental care system 106 and/or the dental professional system 150), and/or communicate with dental professionals (e.g., users of the dental professional system 150).

Dental professional system 150 generally represents any type or form of computing device capable of reading computer-executable instructions. Dental professional system 150 may be, for example, a desktop computer, a tablet computing device, a laptop, a smartphone, an augmented reality device, or other consumer device. Additional examples of dental professional system 150 include, without limitation, laptops, tablets, desktops, servers, cellular phones, Personal Digital Assistants (PDAs), multimedia players, embedded systems, wearable devices (e.g., smart watches, smart glasses, etc.), smart vehicles, smart packaging (e.g., active or intelligent packaging), gaming consoles, Internet-of-Things devices (e.g., smart appliances, etc.), variations or combinations of one or more of the same, and/or any other suitable computing device.

In various implementations, the dental professional system 150 is configured to interface with a dental professional. A "dental professional" (used interchangeably with dentist, orthodontist, and doctor herein) as used herein, may include any person with specialized training in the field of dentistry, and may include, without limitation, general practice dentists, orthodontists, dental technicians, dental hygienists, etc. A dental professional may include a person who can assess, diagnose, and/or treat a dental condition. "Assessment" of a dental condition, as used herein, may include an estimation of the existence of a dental condition. An assessment of a dental condition need not be a clinical diagnosis of the dental condition. In some embodiments, an "assessment" of a dental condition may include an "image based assessment," that is an assessment of a dental condition based in part or on whole on photos and/or images (e.g., images that are not used to stitch a mesh or form the basis of a clinical scan) taken of the dental condition. A "diagnosis" of a dental condition, as used herein, may include a clinical identification of the nature of an illness or other problem by examination of the symptoms. "Treatment" of a dental condition, as used herein, may include prescription and/or administration of care to address the dental conditions. Examples of treatments to dental conditions include prescription and/or administration of brackets/wires, clear aligners, and/or other appliances to address orthodontic conditions, prescription and/or administration of restorative elements to address bring dentition to functional and/or aesthetic requirements, etc. The dental professional system 150 may provide to a user software (e.g., one or more webpages, standalone applications (e.g., dedicated treatment planning and/or treatment visualization applications), mobile applications, etc.) that allows the user to interact with users (e.g., users of the dental patient system 102, other dental professionals, etc.), create/modify/manage treatment plans (e.g., those from the virtual dental care system 106 and/or those generated at the dental professional system 150), etc.

Virtual dental care system 106 generally represents any type or form of computing device that is capable of storing and analyzing data. Virtual dental care system 106 may include a backend database server for storing patient data and treatment data. Additional examples of virtual dental care system 106 include, without limitation, security servers, application servers, web servers, storage servers, and/or database servers configured to run certain software applications and/or provide various security, web, storage, and/or database services. Although illustrated as a single entity in FIG. 1A, virtual dental care system 106 may include and/or represent a plurality of servers that work and/or operate in conjunction with one another.

As illustrated in FIG. 1A, dental patient system 102, virtual dental care system, 106, and/or dental professional system 150 may include one or more memory devices, such as memory 140. Memory 140 generally represents any type or form of volatile or non-volatile storage device or medium capable of storing data and/or computer-readable instructions. In one example, memory 140 may store, load, execute in conjunction with physical processor(s) 130, and/or maintain one or more of virtual dental care modules 108. Examples of memory 140 include, without limitation, Random Access Memory (RAM), Read Only Memory (ROM), flash memory, Hard Disk Drives (HDDs), Solid-State Drives (SSDs), optical disk drives, caches, variations, or combinations of one or more of the same, and/or any other suitable storage memory.

As illustrated in FIG. 1A, dental patient system 102, dental professional system 150, and/or server 106 may also include one or more physical processors, such as physical processor(s) 130. Physical processor(s) 130 generally represents any type or form of hardware-implemented processing unit capable of interpreting and/or executing computer-readable instructions. In one example, physical processor(s) 130 may access and/or modify one or more of virtual dental care modules 108 stored in memory 140. Additionally or alternatively, physical processor 130 may execute one or more of virtual dental care modules 108 to facilitate dental care. Examples of physical processor(s) 130 include, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, and/or any other suitable physical processor.

In some embodiments, dental patient system 102 may include a camera 132. Camera 132 may comprise a camera, scanner, or other optical sensor. Camera 132 may include one or more lenses or may, one or more camera devices, and/or one or more other optical sensors. In some examples, camera 132 may include other sensors and/or devices which may aid in capturing optical data, such as one or more lights, depth sensors, etc. In various implementations, the camera 132 is not a clinical scanner. Although depicted as part of the dental patient system 102, in some embodiments, the camera 132 may be part of the dental professional system 150. In some embodiments, the camera 132 may received inputs from and provide information to the dental patient system 102 and/or the dental professional system 150.

Computer-readable medium 104 generally represents any transitory or non-transitory computer-readable medium or architecture capable of facilitating communication or data transfer. In one example, computer-readable medium 104 may facilitate communication between dental patient system 102, dental professional system 150, and/or virtual dental care system 106. In some implementations, computer-readable medium 104 comprises a computer network that facilitates communication or data transfer using wireless and/or wired connections. In some embodiments, the computer-readable medium 104 may be part of a remote server that is configured to communicate with the dental patient system 102, dental professional system 150, and virtual dental care system 106. Examples of computer-readable medium 104 include, without limitation, an intranet, a Wide Area Network (WAN), a Local Area Network (LAN), a Personal Area Network (PAN), the Internet, Power Line Communications (PLC), a cellular network (e.g., a Global System for Mobile Communications (GSM) network), portions of one or more of the same, variations or combinations of one or more of the same, and/or any other suitable network. Computer-readable medium 104 may also comprise a connection between elements inside a single device (e.g., a bus, any communications infrastructure (e.g., communications infrastructure 1912 shown in FIG. 19, etc.).

Virtual dental care datastore(s) 120 include one or more datastore configured to store any type or form of data that may be used for virtual dental care. In some embodiments, the virtual dental care datastore(s) 120 include, without limitation, patient data 136 and treatment data 138. Patient data 136 may include data collected from patients, such as patient dentition information, patient historical data, patient scans, patient information, etc. Treatment data 138 may include data used for treating patients, such as treatment plans, state of treatment, success of treatment, changes to treatment, notes regarding treatment, etc.

Example system 100 in FIG. 1A may be implemented in a variety of ways. For example, all or a portion of example system 100 may represent portions of example system 200 in FIG. 2, system 600 in FIG. 6, system 1300 in FIG. 13, or system 1600 in FIG. 16.

As will be described in greater detail below, one or more of virtual dental care modules 108 and/or the virtual dental care datastore(s) 120 in FIG. 1A may, (when executed by at least one processor of dental patient system 102, virtual dental care system 106, and/or dental professional system 150) enable dental patient system 102, virtual dental care system 106, and/or dental professional system 150 to facilitate providing virtual dental care between a doctor and a patient. "Virtual dental care," as used herein, may include computer-program instructions and/or software operative to provide remote dental services by a health professional (dentist, orthodontist, dental technician, etc.) to a patient, a potential consumer of dental services, and/or other individual. Virtual dental care may comprise computer-program instructions and/or software operative to provide dental services without a physical meeting and/or with only a limited physical meeting. As an example, virtual dental care may include software operative to providing dental care from the dental professional system 150 and/or the virtual dental care system 106 to the dental patient system 102 (e.g., a smartphone, tablet, or other computing device) over the network 104 through e.g., written instructions, interactive applications that allow the health professional and patient to interact with one another, telephone, chat etc. "Remote dental care," as used herein, may comprise computer-program instructions and/or software operative to provide a remote service in which a health professional provides a patient with dental health care solutions and/or services. In some embodiments, the virtual dental care facilitated by the elements of the system 100 may include non-clinical dental services, such as dental administration services, dental training services, dental education services, etc.

Figure 1B:
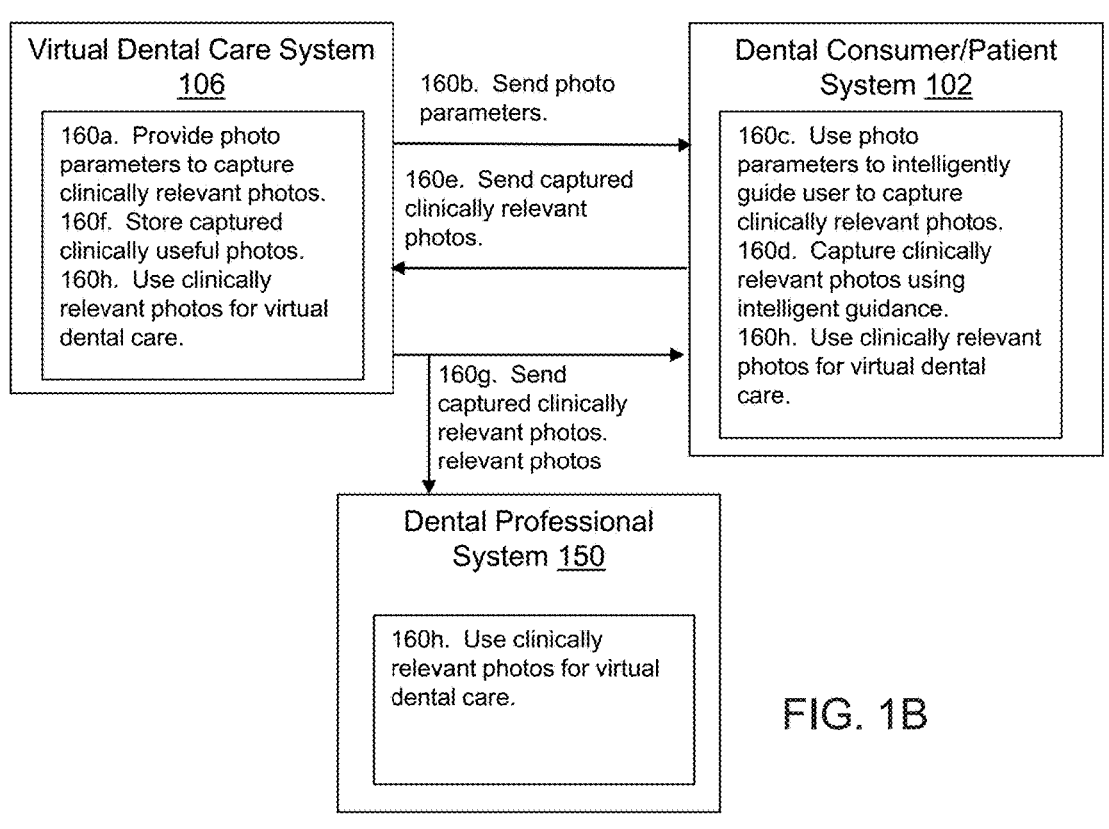
FIG. 1B shows a block diagram of an example system for intelligent photo guidance, in accordance with some embodiments.

In some embodiments, the elements of the system 100 (e.g., the virtual dental care modules 108 and/or the virtual dental care datastore(s) 120) may be operative to provide intelligent photo guidance to a patient to take images relevant to virtual dental care using the camera 132 on the dental patient system 102 (e.g., a smartphone, tablet, or other computing device). An example of how the elements of the system 100 may operate to provide intelligent photo guidance is shown in FIG. 1B.

At an operation 160a, the virtual dental care system 106 may provide one or more photo parameters to capture clinically relevant photos of a user. "Clinically relevant" photos, as used herein, may include images that represent the state of dental conditions in a patient's dentition. Clinically relevant photos may include photos that are sufficient to provide current position(s) and/or orientation(s) of the teeth in a patient's mouth. Examples of clinically relevant photos include photos that show all the teeth in a patient's arch; photos that show the shape of a patient's arch; photos that show locations of teeth that are missing, supernumerary, ectopic, etc.; photos that show malocclusions in a patient's arch (e.g., from front, left buccal, right buccal, and/or other various perspectives); etc. "Photo parameters," as used this context, may include parameters to define clinically acceptable criteria (e.g., clinically acceptable position(s) and/or clinically acceptable orientation(s) of teeth) in one or more photos. Photo parameters can include a distance parameters, e.g., one that parametrizes a distance that a camera is relative to a patient's dentition; orientation parameters (e.g., those that parametrize orientations of photos taken of teeth); openness parameters of a photo of a patient's bite (e.g., whether a bite is open, closed, and/or a degree of openness of a bite); a dental appliance wear parameter of a photo of a patient's bite (e.g., whether a photo shows dental appliances, such as cheek retractors, aligners, etc. in a patient's mouth); camera parameters (brightness parameters of photos; contrast parameters of photos; exposure parameters of photos; etc.); tooth identifier parameters, e.g., those that parametrize the specific teeth in a photo, those taken from a treatment plan; etc. At an operation 160*b*, the virtual care dental system 106 may send the one or more photo parameters to the dental patient system 102. This operation can occur as a file and/or data transfer over the computer-readable medium 104.

At an operation 160*c*, the dental patient system 102 may use the one or more photo parameters to intelligently guide the patient to capture clinically relevant photos of their dentition. The dental patient system 102 may gather image-capture rules that guide capturing the clinically relevant photos based on the photo parameters. The dental patient system 102 may provide a patient with software (e.g., one or more webpages, standalone applications, mobile applications, etc.) that uses the one or more photo parameters to help the patient capture clinically relevant photos of their teeth. As an example, distance parameters may be used to guide a patient to position and/or orient the dental patient system 102 a specific distance away from their teeth to capture a photo with appropriate details of their teeth. The distance parameters may guide whether the position of a camera is too close or too far or the correct distance or within a correct distance range. Orientation parameters may be used to guide a photo to clinically relevant orientations. As an example, orientation parameters may be used to guide a patient to take photos of anterior views, left buccal views, right buccal views, etc. As additional examples, openness parameters may be used to guide a patient to take photos of various bite states, e.g., an open bite, closed bite, and/or a bite that is partially open in order to be clinically relevant; dental appliance wear parameters may be used to detect cheek retractors and/or guide a patient to position cheek retractors appropriately and/or locate/orient photos to be clinically relevant; dental appliance wear parameters may be used to detect various dental appliances (aligners, retainers, etc.) and guide a patient to remove, move, etc. the dental appliances for photos that are clinically relevant; etc. Additionally, tooth identifier parameters (e.g., those gathered from a treatment plan) can be used to guide a patient to take photos of a sufficient number of teeth so that the photos are clinically relevant. Camera parameters, e.g., contrast, brightness, exposure, etc. parameters may be used to guide patients to take photos that have properties such that the photos are clinically relevant. In some implementations, the dental patient system 102 uses camera parameters to modify one or more photo settings (add/disable flash, adjust zoom, adjust brightness, adjust contrast, adjust shadows, adjust silhouettes, etc. so that clinically relevant photos are captured under various conditions. As noted herein, the operation 160*c* may be performed by automated agents and without human intervention.

At an operation 160*d*, the dental patient system 102 may operate to capture clinically relevant photos using the intelligent guidance. In some implementations, a patient may follow instructions to capture photos of their dentition using the intelligent guidance provided on the dental patient system 102. In various implementations, at least a part of operation 160*d* is performed by automated agents that configure a camera to take photos without human intervention. At an operation 160*e*, the dental patient system 102 may send captured clinically relevant images to the virtual dental care system 106. This operation may occur as a file and/or data transfer over the computer-readable medium 104.

At an operation 160*f*, the virtual dental care system 106 may store the captured clinically relevant photos. In various implementations, the virtual dental care system 106 may store the captured clinically relevant photos in a treatment database associated with a patient, a clinical data file associated with a patient, and/or in any relevant datastore. At an operation 160*g*, the virtual dental care system 106 may send captured clinically relevant photos to the dental patient system 102 and/or the dental professional system 150. This operation may occur over a file and/or data transfer over the computer-readable medium 104.

At an operation 160*h*, the dental patient system 102, the virtual dental care system 106 and/or the dental professional system 150 may use clinically relevant photos for virtual dental care. As an example, the dental professional system 150 may display to the patient instructions in the form of an overlay over an image of the patient's teeth. As another example, the dental professional system 150 may display to the patient verbal and/or interactive instructions on how to modify and/or improve capture of a clinically relevant photo. In some implementations, the dental patient system 102, the virtual dental care system 106 and/or the dental professional system 150 may, e.g., use clinically relevant photos for image-based assessments, intelligent patient guidance, and/or photo-based refinements.

Figure 1C:
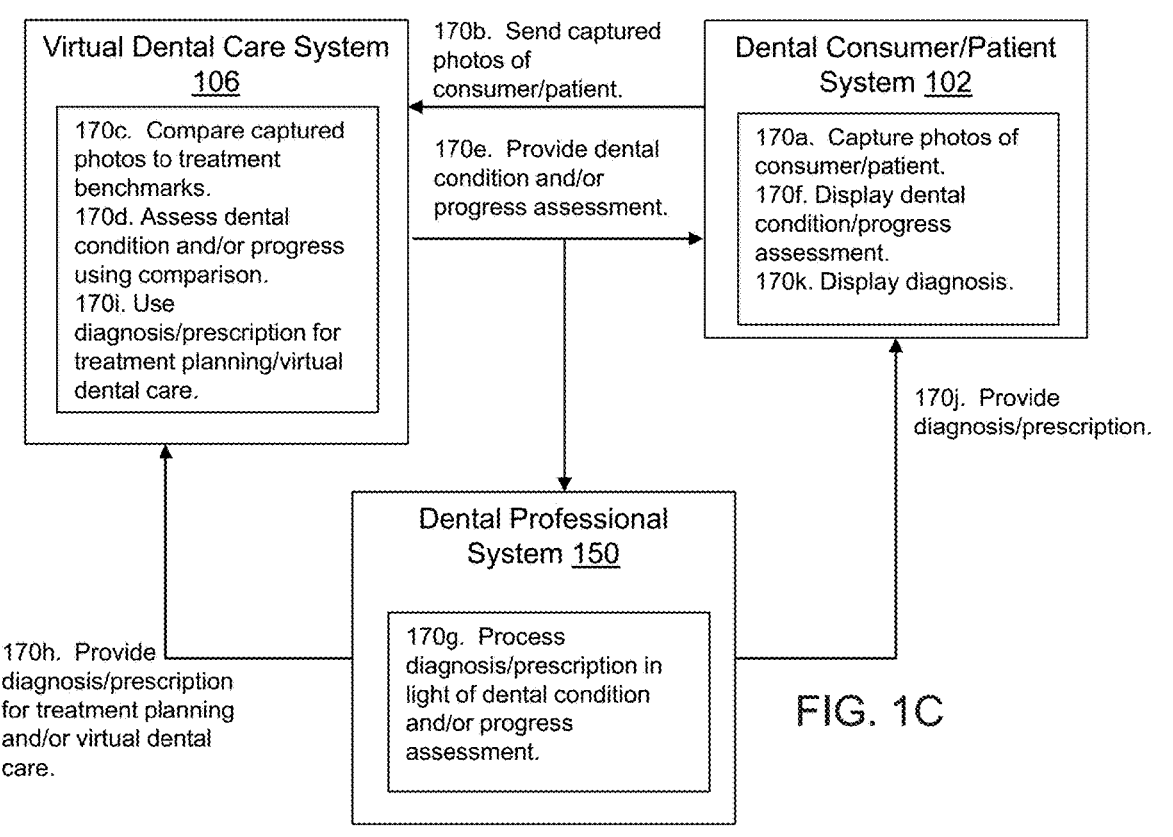
FIG. 1C shows a block diagram of an example system for image-based assessment, in accordance with some embodiments.

In some embodiments, the elements of the system 100 (e.g., the virtual dental care modules 108 and/or the virtual dental care datastore(s) 120) may be operative to provide one or more image-based assessment tools to the users of the dental professional system 150. "Image based assessment tools," as used herein, may include digital tools that operate to provide image-based assessments of a dental condition. In some embodiments, image-based assessments may comprise visualizations that allow a user of the dental professional system 150 to make a decision about a clinical condition. For instance, the elements of the system 100 may provide visualizations that assist a user of the dental professional system 150 with one or more diagnoses of a dental condition. As noted herein, visualizations may include, e.g., visualizations of assessments of a current stage of a treatment plan; visualizations of assessments may, but need not, be based on images and knowledge of a treatment plan that is underway. As another example, the elements of the system 100 may provide visualizations to a user of the dental professional system 150 that provide a view of a patient's assessment over time. An example of how the elements of the system 100 may operate to provide image-based assessment tools is shown in FIG. 1C.

At an operation 170*a*, the dental patient system 102 may capture one or more images of a patient. The one or more images may comprise photos taken by the camera of the dental patient system 102. The one or more photos may be captured by intelligent photo guidance techniques described further herein. The one or more images may include various perspectives and/or views of the dentition of the patient. The one or more photos captured at operation 170*a* need not include scan data, height map information, and/or data a clinical scanner uses to stitch together a mesh representation of patient's dentition. The dental patient system 102 may store images captured locally, in a networked folder, etc. At an operation 170*b*, the dental patient system 102 may send captured photos of the patient to the virtual dental care system 106. This operation may include a file and/or other data transfer over the computer-readable medium 104.

At an operation 170*c*, the virtual dental care system 106 may compare the captured photos to one or more treatment benchmarks. "Treatment benchmarks," as used herein, may include one or more standards or reference points of at least part of a treatment plan. Treatment benchmarks may include intended positions of teeth, jaws, palatal regions, etc. of dentition at a specific stage of a treatment plan. In some implementations, treatment benchmarks are represented as intended positions of a specific stage of a treatment plan on a 3D model of a patient's dentition. In various implementations, treatment benchmarks correspond to representations of a patient's dentition from which to assess a dental condition. As examples, treatment benchmarks may represent a variety of malocclusions for which the patient is to be assessed. At an operation 170*d*, the virtual care dental system 106 may assess a dental condition and/or progress of a treatment plan using the comparison of the captured photos and the treatment benchmarks. As noted herein, the assessment need not comprise a diagnosis of the dental condition and/or the progress through the treatment plan.

At an operation 170*e*, the virtual dental care system 106 may provide the dental patient system 102 and/or the dental professional system 150 the assessed dental condition and/or the progress assessment. This operation may occur as a file and/or data transfer over the computer-readable medium 104. The dental patient system 102 and/or the dental professional system 150 may perform additional operations with the assessed dental condition and/or the progress assessment. As one example, the dental patient system 102 may, at an operation 170*f*, display the dental condition and/or the progress assessment. For instance, the dental patient system 102 may display, e.g., in an application and/or in webpages, user interface elements (annotated 3D models, annotated images, informative and/or interactive user interface elements, etc.) that show an assessment to a patient.

As another example, the dental professional system 150 may, in an operation 170*g*, process a diagnosis and/or prescription for a patient using the dental condition and/or progress assessment. In the operation 170*g*, the diagnosis may also be based on one or more clinical images (intraoral scans, x-rays, CBCT scans, etc.) of the patient's dentition. In some implementations, a doctor may use software on the dental professional system 150 to perform a diagnosis of a dental condition and/or of progress of a treatment plan. As an example, a doctor may use treatment planning software on the dental professional system 150 to diagnose malocclusions and/or other dental conditions reflected in the photos from the patient. Instructions corresponding to the diagnosis may be processed by the dental professional system 150. In various implementations, a dental professional may provide a prescription to treat one or more dental conditions. As an example, a dental professional may prescribe through the dental professional system 150 one or more dental appliances (clear aligners, orthodontic appliances, restorative appliances, etc.) to treat dental conditions that are associated with the dental condition and/or progress assessment. For an initial assessment, the prescription may comprise an initial prescription for dental appliances. For a progress assessment, the prescription may comprise corrective dental appliances that are configured to correct deviation(s) from a treatment plan.

At an operation 170*h*, the dental professional system 150 may provide the diagnosis and/or prescription for treatment planning and/or virtual dental care to the virtual dental care system 106. At an operation 170*i*, the virtual care dental system 106 may use the diagnosis/prescription for treatment planning and/or virtual dental care. At an operation 170*j*, the dental professional system 150 may provide the diagnosis and/or prescription to the dental patient system 102. At an operation 170*k*, the dental patient system 102 may display the diagnosis to the patient.

In some embodiments, the elements of the system 100 (e.g., the virtual dental care modules 108 and/or the virtual dental care datastore(s) 120) may be operative to provide intelligent patient guidance to patients that use the dental patient system 102. "Intelligent patient guidance," as used herein, may include instructions to guide a patient to take one or more actions. In some implementations, the elements of the system 100 generate intelligent patient guidance using photos of a patient, treatment parameters supplied by a doctor, and/or other information.

In some implementations, intelligent patient guidance is supplied by automated agents without intervention (or with minimal intervention, e.g., a doctor providing treatment parameters and/or interacting with a guidance template). Intelligent patient guidance may include: e.g., instructions to change (and/or when to change) a specific dental appliance (e.g., an aligner, a retainer, etc.); instructions to continue use (and/or when to continue use) of a dental appliance in relation to a subsequent dental appliance, instructions to use (and/or a location of use) of a supplemental dental appliance (e.g., chewie, mint, etc.); instructions to direct attention to a region of a patient's dentition (anterior portions, posterior portions, portions that are likely to move during a specific stage, portions that anchor various tooth movements, etc.); instructions to notify a doctor at a specific time or in response to a specific event (e.g., teeth moving at a specific time, teeth moving in accordance with a specific movement pattern, etc.); instructions to capture one or more images of a patient's dentition for the purpose of progress tracking at a specified time/treatment stage; instructions to the patient to visit a doctor, set an appointment, or take other action in relation to a doctor; etc. As noted herein, intelligent patient guidance can include any combination and/or variations of the foregoing examples.

Intelligent patient guidance may accommodate deconfliction, e.g., may be determined based on prioritizing some forms of action and/or removing some conflicting forms of action from guidance. Guidance Rules may provide a set of conflicting or prioritized guidance to the patient. E.g., use a chewie (due to one rule) and set an appointment (due to another) and have the system alert the doctor (due to a third rule); in a case such as this, only an alert to a doctor rule might be activated because the doctor may override the other rules. Another example might be the rules indicating the use of a chewie on the first premolar and another rule indicating a chewie on the second premolar on the same side—clearly only one chewie is needed. Deconfliction may ensure that patient is provided with only relevant guidance.

Intelligent patient guidance supplied by the elements of the system 100 may be based on a dental condition and/or progress assessment (e.g., one reflected by images captured by a patient), treatment parameters, etc. "Treatment parameters," as used herein, may include a set of parameters that are used to specify attributes of a treatment plan to apply to a patient. Treatment parameters may include doctor-preference parameters, e.g., treatment parameters specifying treatment protocols that a doctor (and/or other doctors, e.g., those whose treatment protocols are used by a specific doctor) would prescribe for various patients and/or clinical conditions. Treatment parameters may include per-patient parameters, e.g., parameters used to specify treatment protocols for a specific patient. Per-patient parameters may be based on attributes of a patient (past treatments, anatomical information (attributes of specific dentitions, jaws, etc.), etc. Per-patient parameters need not be based on attributes of a specific patient, and, e.g., may include demographic information (information related to the patient's race, gender, age, etc.), information about historically treated cases (e.g., those with similar forms of dental conditions to the patient) information about idealized dental arches (e.g., those related to dental arches with idealized/near-idealized occlusions as defined by treatment professionals), and/or other information.

In some implementations, the elements of the system 100 may utilize a doctor guidance template, which, as used herein, may include a formatted data structure that specifies a set of rules that a doctor can use for tracking a treatment plan. Examples of rules could be as specific as central incisors deviations from the treatment plan of 0.75 millimeters (mm) should result in a new appointment; central incisor deviations of 0.5-0.75 mm should be watched; central incisor deviations that increase over a period of two (2) months should result in a new appointment; central incisor deviations of 0.25 to 0.5 mm should wear the current set of aligners for an additional week; and central incisor deviations less than 0.25 mm can be considered "on-track". Other rules may specify that teeth marked "Do No Move" should not deviate from their treatment position and any deviation greater than 0.25 mm should result in an appointment. Rules in a doctor guidance template may allow conditionals based on a treatment plan and/or other factors. In some implementations, rules in a doctor guidance template may be written with a temporal frame of reference and/or based on patient historical data (e.g., historical information about patient guidance provided to a patient in the past and/or historical measurement information). An example of how the elements of the system 100 may operate to provide intelligent patient guidance is shown in FIG. 1D.

At an operation 180*a*, the dental patient system 102 may capture one or more images of a patient. The one or more images may comprise photos taken by the camera of the dental patient system 102. The one or more photos may be captured by intelligent photo guidance techniques described further herein. The one or more images may include various perspectives and/or views of the dentition of the patient. The one or more photos captured at operation 180*a* need not include scan data, height map information, and/or data a clinical scanner uses to stitch together a mesh representation of patient's dentition. The one or more photos may reflect a state of a treatment plan that is intended for and/or is underway on the patient. As an example, the one or more photos may capture an initial assessment of the patient's dentition and/or reflect the patient's progress at a specified stage of a treatment plan. The dental patient system 102 may store images captured locally, in a networked folder, etc. At an operation 180*b*, the dental patient system 102 may send captured photos of the patient to the virtual dental care system 106. This operation may include a file and/or other data transfer over the computer-readable medium 104.

At an operation 180*c*, the dental professional system 150 may gather treatment parameters for the patient. As noted herein, the treatment parameters may include doctor-preference parameters, per-patient parameters, etc. At an operation 180*d*, the dental professional system 150 may send the treatment parameters to the virtual dental care system 106. This operation may include a file and/or transfer over the computer-readable medium 104. As noted herein, the treatment parameters may comprise doctor-preference parameters and/or per-patient parameters.

At an operation 180*e*, the virtual dental care system 106 may create and/or update a doctor guidance template with treatment parameters. As noted herein, the doctor guidance template may supply a template with one or more rules that a doctor can use to track implementation of a treatment plan to a patient. The doctor guidance template may accommodate one or more rules to perform guidance deconfliction and/or prioritize various forms of action given doctor preferences, patient attributes, etc. The virtual dental care system 106 may store a doctor guidance template in any relevant format, including but not limited to any transitory and/or non-transitory medium. The virtual dental care system 106 may, in an operation 180*f*, send a doctor guidance template to the dental professional system 150.

At an operation 180*g*, the dental professional system 150 may process instructions to review, edit, and/or approve a doctor guidance template. In some implementations, the dental professional system 150 may provide a doctor with a user interface and/or other software that allows the doctor to review doctor guidance templates, make any changes to a doctor guidance template, and/or approve/finalize a doctor guidance template so that it can be applied to a specific patient, such as the patient using the dental patient system 102. As an example, in some implementations, a doctor may provide instructions to override a specific part of a doctor guidance template based on one or more factors, such as factors related to specific attributes of a specific patient. The dental professional system 150 may, in an operation 180*h*, send a reviewed/edited/approved doctor guidance template to the virtual dental care system 106. This operation may occur as a file and/or data transfer over the computer-readable medium 104.

At an operation 180*i*, the virtual dental care system 106 may use the captured photos and optionally the guidance template to generate intelligent patient guidance rules (e.g., rules that guide application of the treatment parameters to the patient). In some implementations, the virtual care dental system 106 may use the captured photos that were captured at the dental patient system 102 and a doctor guidance template reviewed, edited, and/or approved by the dental professional system 150 to generate intelligent patient guidance rules for the patient. At an operation 180*j*, the virtual care dental system 106 can generate patient guidance instructions using the intelligent patient guidance rules. Patient guidance instructions may take the form of instructions to the patient to take specific actions (add/change a dental appliance, wear a dental appliance longer or shorter than initially prescribed), may take the form of instructions to modify appointments and/or tasks, and/or may take the form of instructions to interact with the doctor in new and/or modified ways (e.g., draw attention to an area of dentition that is of increased interest).

At an operation 180*k*, the virtual dental care system 106 may provide patient guidance instructions to the dental patient system 102 and/or the dental professional system 150. This operation may occur as a file and/or data transfer over the computer-readable medium 104.

At an operation 180*k*, the dental patient system 102 may guide a patient using patient guidance instructions. In various implementations, the patient system 102 may present a patient with automated and/or interactive software elements that instruct the patient to take specified actions in relation to their treatment plans. As noted herein, example actions include instructions to change a dental appliance, instructions to keep a dental appliance beyond an initially pre-scribed time, use a supplemental dental appliance at a specific time/location, set an appointment for a specific condition and/or at a specific time/place, etc. At an operation 180*l*, the dental professional system 150 may guide the doctor with patient guidance instructions. In various imple-mentations, the dental professional system 150 may present a doctor with automated and/or interactive software ele-ments that, e.g., set appointments for a patient, notify a doctor about one or more conditions and/or regions of a patient's dentition to focus on, etc.

In some embodiments, the elements of the system 100 (e.g., the virtual dental care modules 108 and/or the virtual dental care datastore(s) 120) may be operative to provide photo-based refinements to users of the dental professional system 150. "Photo-based refinements," as used herein, may include tools that allow a doctor performing virtual dental care to prescribe orders for patients whose treatments devi-ate from an intended course of treatment. The tools may use photos and may avoid requirements to rescan (e.g., perform a second and/or subsequent clinical scan after an initial clinical scan) the patient and/or provide a live evaluation of the patient, e.g., at the doctor's office. In some implemen-tations, photo-based refinements may provide tools for a doctor to create a secondary (e.g., a refined) treatment plan remotely without ever physically seeing and/or evaluating a patient. Photo-based refinements may optimize one or more camera parameters to align a patient's treatment plan to photos captured by/for the patient. Photo-based refinements may also optimize one or more pose parameters (e.g., location parameters, orientation parameters, etc.) of a patient's teeth to ensure the teeth are in appropriate spaces. As noted herein, photo-based refinements may be displayed to doctors as user interface elements (e.g., overlays) repre-senting a patient's dentition in relation to a treatment plan. Photo-based refinements can be used to plan one or more refinement treatment plans using 3D tooth shapes from a primary treatment plan and/or locations found using the techniques described herein; as noted herein, this informa-tion may be used to plan one or more new/refined treatment plans. An example of how the elements of the system 100 may operate to provide photo-based refinements is shown in FIG. 1E.

At an operation 190*a*, the dental patient system 102 may capture one or more images of a patient at a particular time, e.g., at one or more time during the course of virtual dental care. The one or more images may comprise photos taken by the camera of the dental patient system 102. The one or more photos may be captured by intelligent photo guidance tech-niques described further herein. The one or more images may include various perspectives and/or views of the den-tition of the patient. As an example, the one or more images may include a plurality of images that represent more than one perspective of the patient's dentition. For instance, the images may be taken from anterior, left buccal, right buccal, and/or other perspectives. As noted herein, the one or more images may be captured as the patient is intelligently guided to take photos of their dentition. The one or more photos captured at operation 190*a* need not include scan data, height map information, and/or data a clinical scanner uses to stitch together a mesh representation of patient's denti-tion. The one or more photos may reflect a state of a treatment plan that is intended for and/or is underway on the patient. As an example, the one or more photos may capture an initial assessment of the patient's dentition and/or reflect the patient's progress at a specified stage of a treatment plan. The dental patient system 102 may store images captured locally, in a networked folder, etc. At an operation 190*b*, the dental patient system 102 may send captured photos of the patient to the virtual dental care system 106. This operation may include a file and/or other data transfer over the computer-readable medium 104.

At an operation 190*c*, the dental professional system 150 may request a first treatment plan for the patient. In some implementations, a doctor may, through instructions pro-vided to the dental professional system 150, request a first treatment plan for a patient. The first treatment plan may comprise any set of instructions to address a dental condition of the patient. As an example, the first treatment plan may include instructions to move a patient's teeth from a first arrangement toward a target arrangement. The first treatment plan may prescribe use of successive dental appliances (e.g., a plurality of successive aligners shaped to receive and resiliently reposition a patient's teeth from the initial arrangement toward the target arrangement). The first treat-ment plan may include restoring attributes of a patient's dentition using crowns, bridges, implants, and/or other restorative dental appliances. In various implementations, the first treatment plan is based on a clinical scan, such as a clinical scan that occurred before the operation 190*a*.

At an operation 190*d*, the dental professional system 150 may send the request for the first treatment plan to the virtual dental care system 106. This operation may occur as a file and/or data transfer over the computer-readable medium 104.

At an operation 190*e*, the virtual dental care system 106 may retrieve the first treatment plan in response to the request for the first treatment plan. Retrieving the first treatment plan may involve providing instructions to a treatment datastore to retrieve a clinical data file associated with a patient. The clinical data file may represent an initial position of the patient's dentition, an intended target position of the patient's dentition, and/or a plurality of intermediate positions to move the patient's dentition from the initial position toward the intended target position. In some imple-mentations, the clinical data file may include specific clini-cal preferences (stage(s) at which interproximal reduction (IPR) was performed, locations and/or times of application of attachments applied during the first treatment plan, etc.). The clinical data file may also include clinical preferences of the doctor who managed prescription of the first treatment plan as well as specific attributes of dental appliances used to implement the first treatment plan.

At an operation 190*f*, the virtual dental care system 106 may identify an intended arrangement of a first treatment plan at the particular time that the photos of the patient were taken at the dental patient system 102. The virtual dental care system 106 may, e.g., use a length of time since initial implementation of the first treatment plan, spatial relation-ships between teeth in the photos captured at the dental patient system 102, and/or other information to identify the stage of the first treatment plan at which the photos were captured at the dental patient system 102. The virtual dental care system 106 may further evaluate a file that represents the intended arrangement of the identified stage of the first treatment plan to identify 3D structures, e.g., meshes cor-responding to the identified stage of the first treatment plan.

At an operation 190*g*, the virtual dental care system 106 may evaluate photo parameters of the photos captured at the dental patient system 102 to generate alignment data, e.g., data representing an alignment of the intended arrangement of the first treatment plan to the photos. In some implementations, the virtual dental care system 106 optimizes 3D parameters from the images captured at the dental patient system 102. Examples of 3D parameters that may be optimized include camera parameters, location parameters, orientation parameters, etc. 3D parameter optimization may be performed using a variety of techniques, such as differential rendering, expectation maximization, etc. Applicant hereby incorporates by reference the following applications as if set forth fully here: U.S. Pat. App. Ser. No. 62/952,850, U.S. patent application Ser. No. 16/417,354; U.S. patent application Ser. No. 16/400,980; U.S. patent application Ser. No. 16/455,441; and U.S. patent application Ser. No. 14/831,548 (now U.S. Pat. No. 10,248,883). Once photo parameters are evaluated/optimized, the virtual dental care system 106 may use those photo parameters to determine places where the patient's teeth are not tracking to the first treatment plan. For instance, the virtual dental care system 106 may evaluate where the patient's teeth are in intended locations/orientations as well as where teeth deviate from intended locations/orientations.

At an operation 190h, the virtual care dental system 106 may generate an alignment mesh (e.g., an updated, segmented mesh) using the alignment data. The alignment mesh may comprise a 3D representation of the patient's dentition that reflects the photos taken at the patient system 102. At an operation 190i, the virtual care dental system 106 may evaluate the first treatment plan for modifications using the alignment mesh. The virtual dental care system 106 may identify locations where the patient's teeth are off-track and/or deviating from an intended arrangement prescribed by the first treatment plan. The virtual dental care system 106 may store any modifications in a clinical data file associated with the patient. At an operation 190j, the virtual dental care system 106 may send proposed modifications to a doctor. This operation may occur as a file and/or data transfer over the computer-readable medium 104.

At an operation 190k, the dental professional system 150 may present and/or facilitate review of proposed modifications to the doctor. In various implementations, the dental professional system 150 shows a doctor the proposed modifications on a 3D model and/or images representing the patient's dentition. The dental professional system 150 may further allow the doctor to accept, reject, and/or further modify the 3D model and/or the images. As an example, the dental professional system 150 may allow the doctor to further move positions of attachments, modify aligners and/or force systems, modify stages at which IPR is performed, etc. At an operation 190l, the dental professional system 150 may send reviewed modifications to the virtual dental care system 106, e.g., as a file and/or data transfer over the computer-readable medium 104. At an operation 190m, the virtual dental care system 106 may update the first treatment plan with the reviewed modifications. In various implementations, the virtual dental care system 106 updates a clinical data file associated with the patient with the reviewed modifications.

For example, and as will be described in greater detail below, one or more of virtual dental care modules 108 may cause dental patient system 102, the dental professional system, 150, and/or the virtual dental care system 106 to recite steps of method claim using one or more of FIGS. 3, 7, 14, 15, and/or 17.

Intelligent Photo Guidance

To perform virtual orthodontic care, virtual dental care, and/or other remote medicine, the practitioner may wish to visually inspect the patient. For example, the practitioner may wish to inspect the patient's progress during a treatment plan, diagnose possible dental issues, and modify the treatment plan as needed. The availability of high-resolution cameras, for instance integrated with smartphones, allows patients to take sufficiently high-resolution photos that may enable the practitioner to inspect patients. However, patients may not know how to properly frame the clinically relevant body parts for the practitioner to inspect. For example, an orthodontic practitioner may require specific views of specific teeth of the patient. The patient may not be aware of which specific teeth to capture, which angles to take photos, whether to wear oral appliances, etc.

As will be described further below, the systems and methods provided in this disclosure may utilize artificial intelligence to provide a patient with guidance on taking clinically relevant orthodontic photos. The systems and methods provided in this disclosure may improve the functioning of a computing device by more efficiently acquiring image data, which may further reduce storage requirements and network bandwidth. In addition, the systems and methods provided herein may improve the field of virtual medicine by improving the functional capabilities of remote devices. Moreover, the systems and methods provided herein may improve the field of medical imaging by providing a near-real-time classification of images for various classifiers.

Figure 2:
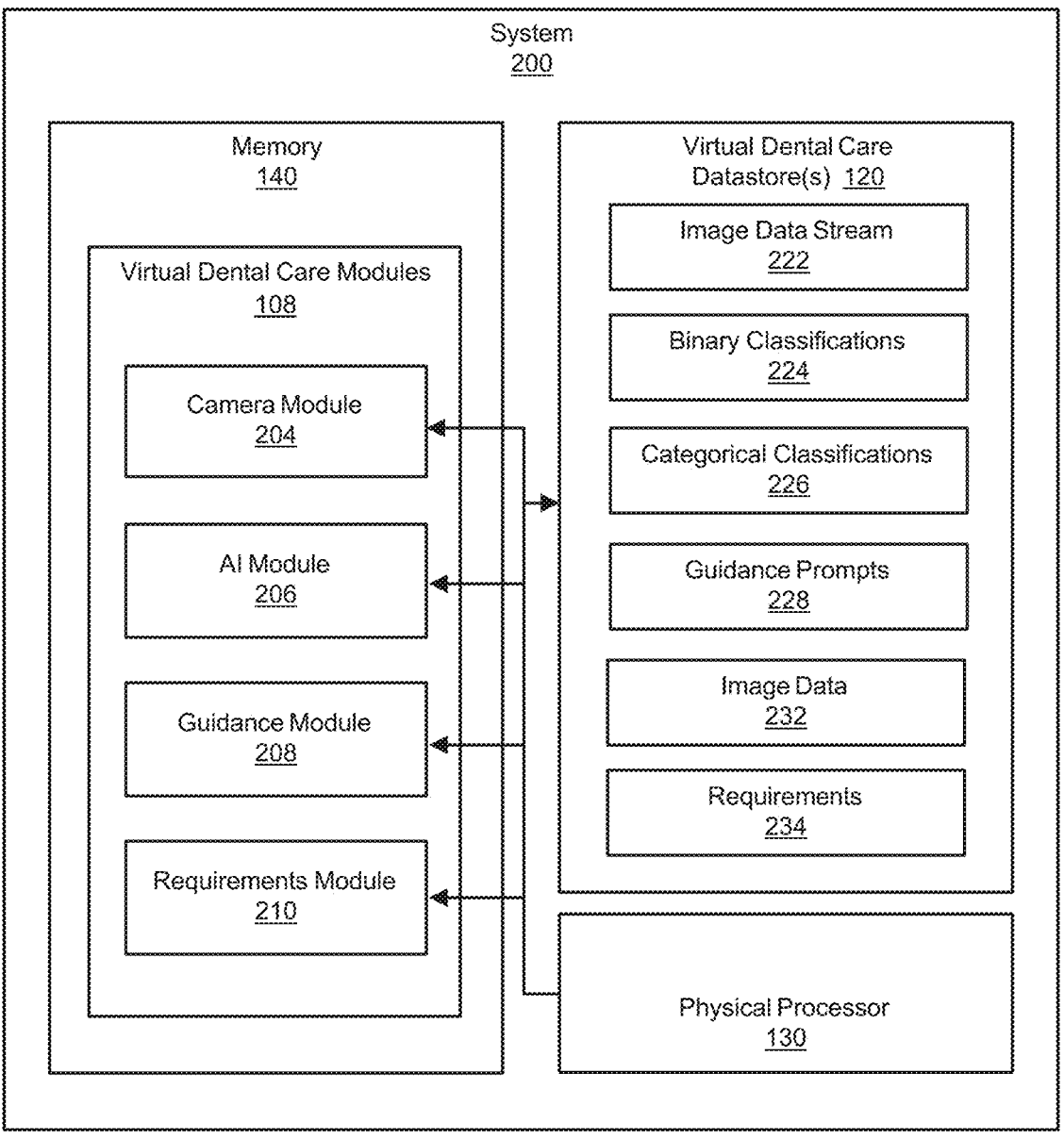
FIG. 2 shows a block diagram of an example system for photo guidance, in accordance with some embodiments.

FIG. 2 is a block diagram of an example system 200 for artificial intelligence (AI) assisted photo guidance. As illustrated in this figure, example system 200 may include one or more virtual dental care modules 108 for performing one or more tasks. As will be explained in greater detail below, virtual dental care modules 108 may include a camera module 204, an AI module 206, a guidance module 208, and a requirements module 210. Although illustrated as separate elements, one or more of virtual dental care modules 108 in FIG. 2 may represent portions of a single module or application.

In certain embodiments, one or more of virtual dental care modules 108 in FIG. 2 may represent one or more software applications or programs that, when executed by a computing device, may cause the computing device to perform one or more tasks. For example, and as will be described in greater detail below, one or more of virtual dental care modules 108 may represent modules stored and configured to run on one or more computing devices, such as the devices illustrated in FIG. 1A (e.g., dental patient system 102 and/or server 106). One or more of virtual dental care modules 108 in FIG. 2 may also represent all or portions of one or more special-purpose computers configured to perform one or more tasks.

As illustrated in FIG. 2, example system 200 may also include one or more virtual dental care datastore(s) 120, such as an image data stream datastore 222, binary classifications datastore 224, categorical classifications datastore 226, guidance prompts datastore 228, image data 232, and requirements data 234. Virtual dental care datastore(s) 120 may comprise one or more datastores configured to store any type or form of data or information.

FIG. 3 is a flow diagram of an exemplary computer-implemented method 300 for AI-assisted photo guidance. The steps shown in FIG. 3 may be performed by any suitable computer-executable code and/or computing system, including the system(s) illustrated in FIGS. 1 and 2. In one example, each of the steps shown in FIG. 3 may represent an algorithm whose structure includes and/or is represented by multiple sub-steps, examples of which will be provided in greater detail below.

As illustrated in FIG. 3, at step 302 one or more of the systems described herein may receive an image data stream from a camera. For example, camera module 204 may receive image data stream 222 from camera 132 of system 200 or another camera in communication with system 200.

In some embodiments, the term "image data stream" may refer to optical capture data which may be temporarily stored in a buffer (e.g., a camera buffer) or otherwise saved in a device memory. Examples of image data streams include, without limitation, one or more photos, video, etc. An image data stream may include additional sensor data, such as depth data.

The systems described herein may perform step 302 in a variety of ways. In one example, camera module 204 may receive image data stream 222 from a buffer of camera 132. Image data stream 222 may be image data temporarily stored, such as image data corresponding to a viewfinder of camera 132. In other examples, image data stream 222 may include captured and stored images.

FIG. 4 illustrates data flow of a device 400, which may correspond to system 200 and/or dental patient system 102. At 404, a camera image/video buffer may temporarily store image data (e.g., image data stream 222). Image data stream 222 may be raw image and/or video data or may be processed. For example, image data stream 222 may be corrected for any visual artefacts, compressed and/or decompressed, reformatted and/or resized for further processing, etc.

Returning to FIG. 3, at step 304 one or more of the systems described herein may determine, using an artificial intelligence scheme, one or more binary classifications and one or more categorical classifications from the image data stream. For example, AI module 206 may determine binary classifications 224 and categorical classifications 226 from image data stream 222.

In some embodiments, the term "binary classification" may refer to characteristics that may be defined as having one of two states (e.g., yes, or no). With respect to the image data stream, examples of binary classifications may include, without limitation, whether a particular tooth is visible, whether an upper jaw is visible, whether a lower jaw is visible, whether an appliance (e.g., an aligner, a cheek retractor, etc.) is visible, whether a focal distance threshold—corresponding to whether an entirety of the body part is visible—is satisfied, whether upper and lower teeth contact, whether a lighting threshold is satisfied, whether a localized calculus (e.g., plaque buildup) is present, and whether a gingiva recession is present.

In some embodiments, the term "categorical classification" may refer to characteristics that may be classified into one or more categories. In some implementations, the characteristics may be classified into one or more sets of mutually exclusive categories. With respect to the image data stream, examples of categorical classifications may include, without limitation, an anterior view, a left buccal view, and a right buccal view.

The systems described herein may perform step 304 in a variety of ways. In one example, AI module 206 may analyze image data stream 222 and save the analysis results as binary classifications 224 and categorical classifications 226. In FIG. 4, at 406, image data stream 222 may be classified by the neural network classifier (e.g., AI module 206).

Figure 5:
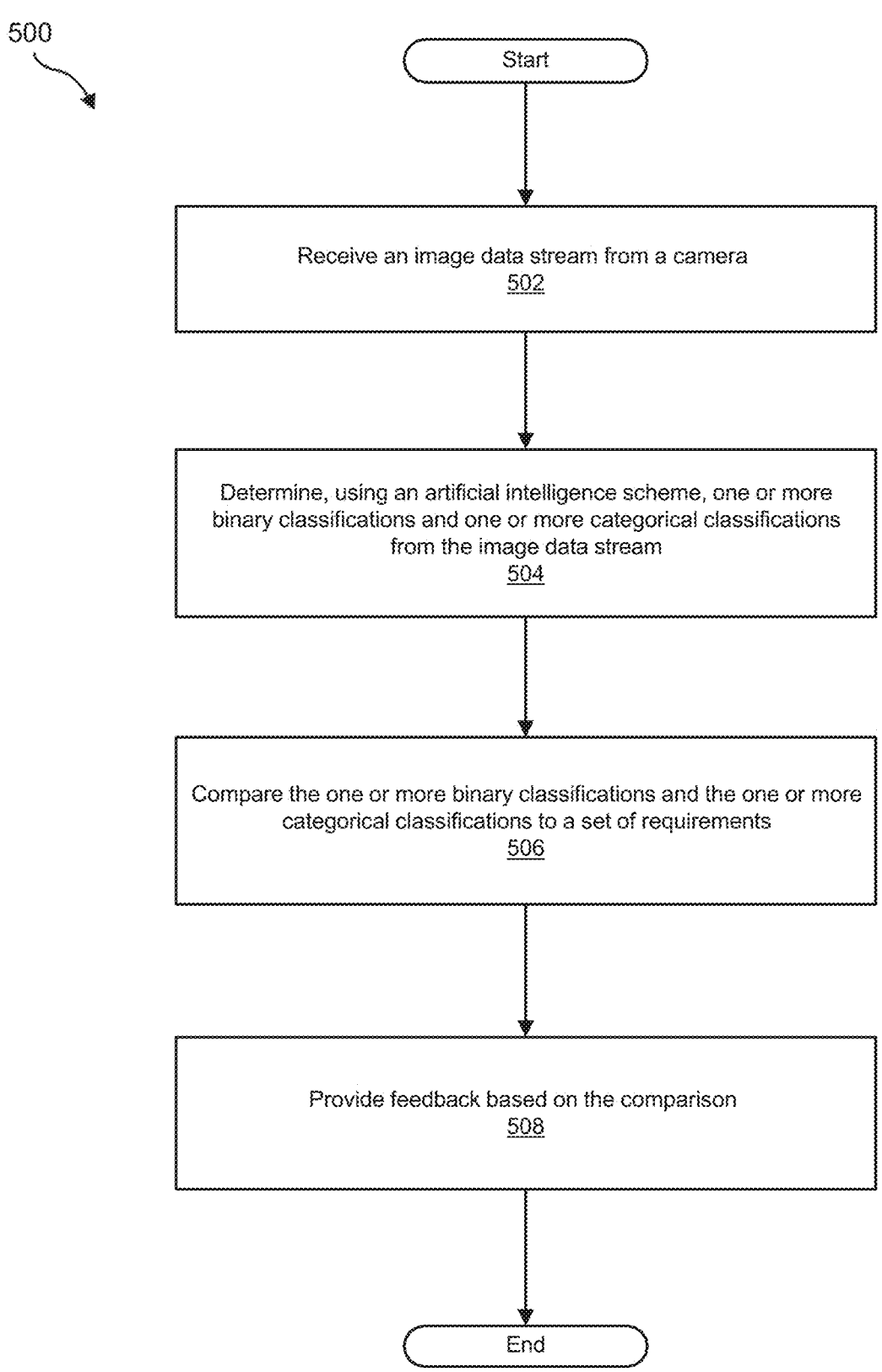
FIG. 5 shows an example neural network for photo guidance, in accordance with some embodiments.

FIG. 5 illustrates an environment 500 for classification. Images 522, which may correspond to image data stream 222, may be an input to neural network 506, which may correspond to AI module 206. Neural network 506 may include one or more AI schemes, such as a convolutional neural network, deep learning, etc. Neural network 506 may undergo training via training data in order to recognize the various classifications described above. Neural network 506 may determine categorical classifications 526, which may correspond to categorical classifications 226.

In addition, neural network 506 may include a binary classifier. The binary classifier may determine the binary classifications using binary cross-entropy, which may utilize a loss function to predict a probability of between two possible values for each binary classification. Neural network 506 may determine binary classifications 524, which may correspond to binary classifications 224.

Turning back to FIG. 3, at step 306 one or more of the systems described herein may compare the one or more binary classifications and the one or more categorical classifications to a set of requirements. For example, guidance module 208 may compare binary classifications 224 and categorical classifications 226 to requirements 234. The requirements may indicate what clinically relevant information may be required, particular with respect to photos.

The systems described herein may perform step 306 in a variety of ways. In one example, requirements module 210 may determine requirements 234 that may be customized for a particular patient at a particular state of treatment. For example, requirements module 210 may analyze patient data 136 and/or treatment data 138 to determine requirements 234. Patient data 136 may indicate patient-specific circumstances which may affect requirements 234. For example, patient data 136 may indicate that the patient is missing certain teeth such that requirements 234 may not require visibility of teeth that are known to be missing and therefore not visible.

In some examples, requirements module 210 may reside in server 106 such that requirements 234 may be sent to dental patient system 102. In other examples, server 106 may send patient data 136 and/or treatment data 138 to dental patient system 102 such that computing device 102 may locally determine requirements 234. FIG. 4 illustrates at 410 that requirements and expectations (e.g., requirements 234) may be an input for guidance generation and capture initiation at 408.

Requirements 234 may include, for instance, visibility of a particular body part, visibility of a particular appliance, and type of view captured. The particular body part may correspond to a tooth of interest identified from the current state of treatment plan. For example, patient data 136 and/or treatment data 138 may indicate significant movement for a certain tooth. The particular body part may further correspond to one or more teeth near the tooth of interest. For example, if significant movement is expected for a certain tooth, the neighboring teeth may be of interest.

In some examples, the diagnosis may require the patient to wear an appliance. For example, the patient may be required to wear a cheek retractor to properly expose the patient's teeth for viewing. In another example, the patient may be required to wear an orthodontic aligner so that the practitioner may inspect the aligner's interaction with the patient's teeth.

Guidance module 208 may determine from binary classifications 224 and categorical classifications 226 whether requirements 234 are met. For example, guidance module 208 may determine from categorical classifications 226 whether binary the required views of the patient's teeth are captured. Guidance module 208 may determine from binary classifications 224 may indicate whether the required teeth are in the required views.

Returning to FIG. 3, at step 308 one or more of the systems described herein may provide feedback based on the comparison. For example, guidance module 208 may provide guidance prompts 228.

In some embodiments, the term "guidance prompts" may refer to audio, visual, and/or haptic prompts that may provide instruction to a user. Examples of guidance prompts may include, without limitation, overlays on a device screen, text notifications, oral instructions, a tone or other sound, a vibration, etc.

The systems described herein may perform step 308 in a variety of ways. In one example, guidance module 208 may determine guidance prompts 228 based on the comparison. Guidance prompts 228 may include instructions for the user to manipulate system 200 into a configuration that may take images satisfying requirements 234. For example, the instructions may include an instruction to adjust a camera view of the camera to include a particular body part in the camera view, such as moving the camera closer or farther, pan/tilt/zoom the camera, change an angle, tracking or otherwise moving the camera, etc. The instructions may include an instruction to insert or remove a particular appliance. The instructions may also include an instruction to move a particular body part, such as open or close the patient's bite, open the patient's jaw wider, etc. The instruction may include an instruction to adjust one or more camera settings, such as zoom, focus, turn on/off a flash, etc.

Guidance prompts 228 may indicate if requirements 234 are met. For example, guidance prompts 228 may instruct the patient to take the photo to save as image data 232.

In FIG. 4, at 428 the guidance may be displayed (e.g., guidance prompts 228) or the image may be captured. Guidance prompts 228 may include visual prompts that may be displayed visually, such as an overlay showing guidelines, arrows, graphical instructions, as text in an overlay or window, light patterns, grayed out images, ghost images, etc. Guidance prompts 228 may include audible prompts that may be presented as audio, such as oral instructions, chimes, warning tones, increasing/decreasing beeps (e.g., as the view gets closer/further from satisfying requirements 234), etc. Guidance prompts 228 may include haptic prompts that may be presented as vibrations (e.g., of decreasing strength as requirements 234 are closer to satisfaction, a vibration when requirements 234 are satisfied), warning vibrations, or other haptic responses.

The feedback may include instructions to system 200 for performing automatic actions when requirements 234 are not satisfied. Guidance prompts 228 may instruct camera module 204 to automatically adjust one or more camera settings. For example, rather than instruction the patient to adjust the camera settings, camera module 204 may automatically make the adjustments. In another example, guidance prompts 228 may instruct camera module 204 to automatically capture image data 232 if requirements 234 are satisfied. Alternatively, automatically capturing image data 232 may include saving portions of image data stream 222 that satisfies requirements 234. In some examples, guidance prompts 228 may include a confirmation such that the patient may confirm or cancel the automatic actions.

In some examples, guidance prompts 228 may prevent certain actions, such as preventing capture of image data 232 of the body part when at least one of requirements 234 is not satisfied. In some examples, requirements 234 may include hardware requirements (e.g., camera resolution, zoom, etc.) such that guidance prompts 228 may prevent capture of image data 232 if the hardware requirements are not satisfied. In some examples, guidance prompts 228 may include sending a notification. System 200 may send a notification to server 106 or other computing device to inform the practitioner of certain results. For instance, the notification may indicate if an attachment has fallen off of a tooth, that a plaque buildup is detected, or other abnormal condition that may be highlighted for the practitioner.

Although method 300 is presented as a sequence of steps, in some examples, the steps of method 300 may be repeated as needed to provide continuous feedback until the desired images are captured. Thus, certain steps may be repeated, and requirements 234 and/or guidance prompts 228 may be continuously updated until image data 232 is sufficiently captured.

As described above, a patient may have a device, such as a smartphone, that is capable of taking photos. The smartphone may be provided a previously-trained neural network that may assist the patient in taking clinically relevant photos. The patient may be provided guidance to ensure the photos satisfy clinical requirements. The requirements may be customized to the patient at that particular stage of the patient's treatment. Thus, the patient's doctor may be able to remotely view the patient to track the patient's progress, update the treatment, or diagnose any issues.

Although the examples herein are described with respect to orthodontic care, in other implementations the remote care may include any other medical care that may be conducted via external photography.

Image Based Assessment

Image-based systems and methods as described herein may allow for remote assessment and follow-up with a patient during orthodontic treatment. The systems and methods allow a doctor to quickly and accurately assess a patient's progress or lack thereof based on photos or images the patient has taken. The photos or images to be taken outside the doctor's office or other clinical offices and instead may be taken by, for example, a handheld device such as a smart phone or digital camera. The assessment may include tracking the actual movement and position of a patient's teeth during orthodontic treatment as compared to the expected movement and position of the patient's teeth during orthodontic treatment.

In some embodiments, the patient captures two-dimensional photographic images of their teeth, which are then compared with three-dimensional models of the expected position of the patient's teeth during a given stage of treatment. The comparison may include determining the positional deviation or error between the actual position of the patient's teeth and the expected position of the patient's teeth based on a three-dimensional model of the patient's teeth for the particular stage of treatment. Other methods of assessing a patient's progress may include monitoring the fit of an orthodontic aligner on the patient's teeth. However, the fit of an orthodontic aligner or a gap between the orthodontic aligner and the patient's teeth is not necessarily reflective of an off-track deviation of the patient's teeth.

Figure 6:
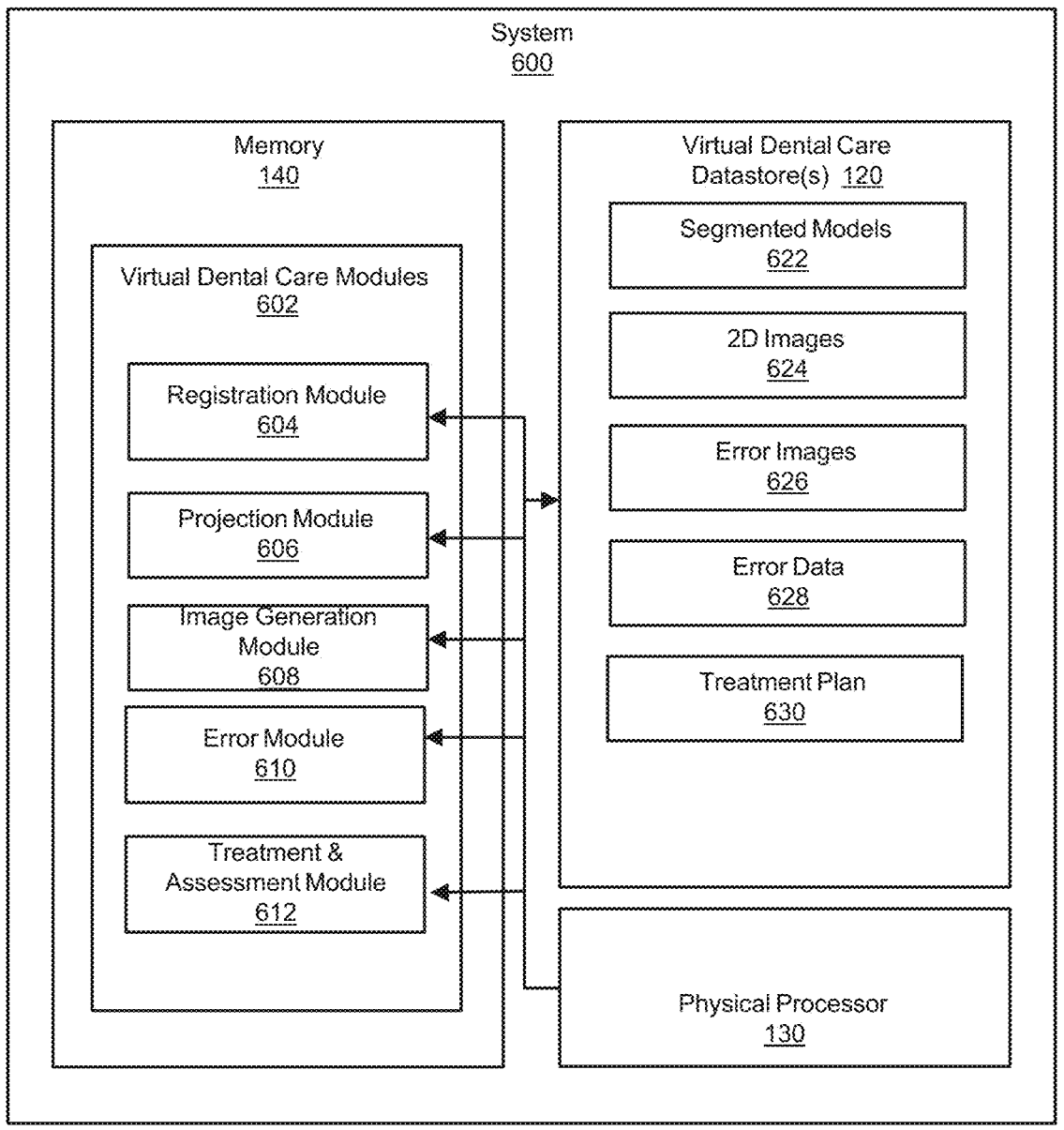
FIG. 6 shows a block diagram of an example system for differential error generation, according to embodiments herein.
Figure 7:
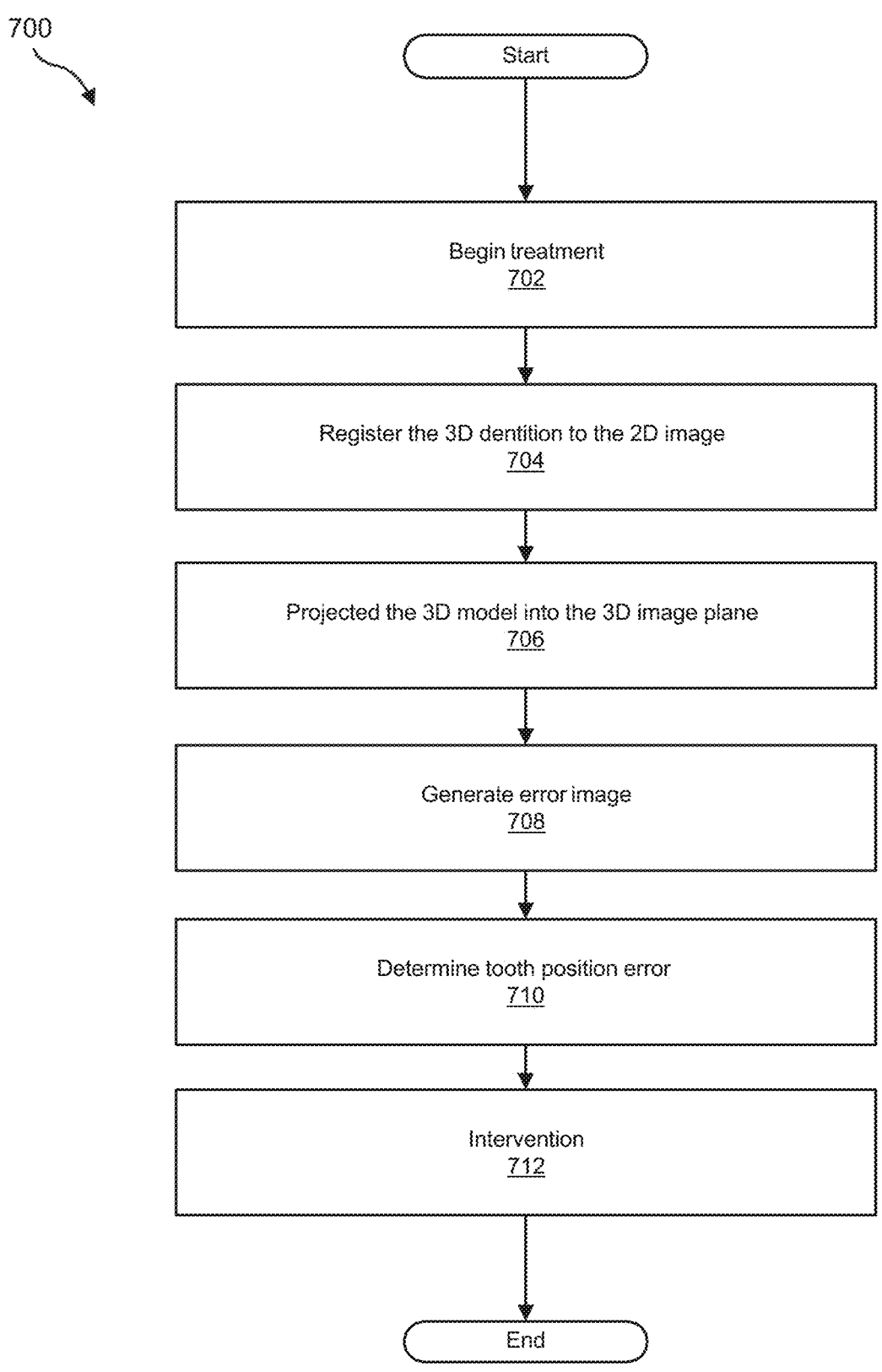
FIG. 7 shows a method of assessing the movement of teeth of a patient, according to embodiments herein, according to embodiments herein.

FIG. 6 is a block diagram of an example system 600 for determining an error between an expected tooth position and an actual tooth position. As illustrated in this figure, example system 600 may include one or more virtual dental care modules 602 for performing one or more tasks. As will be explained in greater detail below, virtual dental care modules 602 may include a registration module 604, a projection module 606, an image generation module 608, an error module 610, and a treatment and assessment module 612. Although illustrated as separate elements, one or more of virtual dental care modules 602 in FIG. 6 may represent portions of a single module or application.

In certain embodiments, one or more of virtual dental care modules 602 in FIG. 6 may represent one or more software applications or programs that, when executed by a computing device, may cause the computing device to perform one or more tasks. For example, and as will be described in greater detail below, one or more of virtual dental care modules 602 may represent modules stored and configured to run on one or more computing devices, such as the devices illustrated in FIG. 1A (e.g., dental patient system 102 and/or server 106). One or more of modules 602 in FIG. 6 may also represent all or portions of one or more special-purpose computers configured to perform one or more tasks.

As illustrated in FIG. 6, example system 600 may also include one or more virtual dental care datastore(s) 120, such as segmented teeth models 622, two-dimensional images 624, error images 626, error data 628, and treatment plan data 630. Virtual dental care datastore(s) 120 may include one or more datastores configured to store any type or form of data or information.

The virtual dental care datastore(s) 120 may include segmented teeth models 622 which may include data representing three-dimensional models of each individual tooth of the patient. The three-dimensional models may be generated based on an initial three-dimensional (or 3D) intraoral scan of the patient's teeth. During an intraoral scan, a handheld scanning device generates a three-dimensional model of the patient's upper and lower arches. After capturing three-dimensional models of the upper and lower arches, each tooth within the three-dimensional model is separated from the model to form an individual tooth model. These individual tooth models are then used during the treatment planning process in order to generate each of the of treatment stages to move the teeth from an initial position towards a target final position and then to generate orthodontic aligners that are worn on the patient's teeth in order to move the teeth from the initial position towards the final position.

The virtual dental care datastore(s) 120 may include two-dimensional (or 2D) images 624 which may include data representing two-dimensional images of the patient's mouth and teeth. In some embodiments, the two-dimensional images 624 are captured using the systems and methods described herein, for example by using the AI based photo capture system discussed above. The two-dimensional images 624 may include one or more of three buccal and two occlusal photos of the patient's teeth. For example, the three buccal photos may include an anterior image of the patient's teeth in occlusion, a left buccal image of the patient's teeth in occlusion, and a right buccal image of the patient's teeth in occlusion. In some embodiments, the buccal photos may also include images of the teeth in a neutral bite or non-occluded position. The two-dimensional images 624 may also include occlusal photos of the patient's teeth. For example, the two-dimensional images 624 may include an image of the occlusal surfaces of teeth of the patient's upper arch and an image of the occlusal surfaces of teeth of the patient's lower arch.

The virtual dental care datastore(s) 120 may include treatment plan data 630. The treatment plan data 630 may include the positions and orientations of each of the patient's teeth for each stage of a treatment plan. In some embodiments, the positions and orientations of the teeth may be stored as three-dimensional positional locations and angular orientations of each tooth and the patient's upper and lower arches. In some embodiments the positions and orientations of the patient's teeth may be stored as a collection of three-dimensional segmented models of the patient's upper and lower arches for each stage of treatment. In some embodiments, the treatment plan data may include other information such as the location of attachments on the patient's teeth, and other orthodontic devices such as wire and bracket braces, elastics, temporary anchorage devices, and other orthodontic devices.

The virtual dental care datastore(s) 120 may include error images 626. The systems and methods disclosed herein may generate error images 626 based on a difference in tooth position between a two-dimensional image of the patient's teeth and a three-dimensional dentition model that is generated based on the expected tooth position for a current stage of the patient's treatment plan. As discussed below with respect to capital FIG. 7, the error images 626 may be generated through a process of registering the 3D model of the patient's expected tooth positions to a current stage two-dimensional photograph or photographs of the patient's dentition. After registration, the dentition is projected into the same image plane as the two-dimensional image and then the difference between the position and orientation of the teeth and the two-dimensional image and the three-dimensional projection are used to form of an error image, for example as shown in FIG. 8. In FIG. 9, a plurality of error images are shown wherein the error between the tooth position in the three-dimensional dentition model and the tooth position in the two-dimensional images are shown via an overlay over the two-dimensional image. In FIG. 10 a plurality of error images are shown wherein the error between the tooth position and the three in the three-dimensional dentition model in the tooth position in the two-dimensional images are shown via an outline of the tooth position of the digital model overlaid onto the two-dimensional images. In FIG. 11 error images may include 3D generated models of the treatment plans current stage next to the 2D image of the patient's teeth.

The virtual dental care datastore(s) 120 may include error data 628. The systems and methods disclosed herein may generate error data in many ways. For example, the error data may be generated based on the differences between the position and orientation of the teeth and the two-dimensional image and the three-dimensional projection. The error data 628 may include differential position and rotational angles in three-dimensional space for each of the teeth in the patient's dentition. FIG. 12 shows an example of a chart generated using error data 628 including differential position between the expected position of each of the patient's tooth at each stage of treatment and the actual position of each of the patient's teeth.

The virtual dental care modules 602 may include a registration module 604. The registration module 604 registers the patient's three-dimensional dentition including three-dimensional segmented models of the teeth and arrangements as found in the current stage of the treatment plan with two-dimensional images of the patient's teeth taken during the current stage of the treatment plan. The three-dimensional segmented models and the two-dimensional images may be registered in many ways. For example, edge detection techniques may be used to determine the edges and shapes of the teeth in the two-dimensional images in order to determine which teeth are visible in the two-dimensional image and where they are located within the two-dimensional image and which teeth in the two-dimensional image correspond to particular teeth and the three-dimensional image.

The virtual dental care modules 602 may include a projection module 606. The projection module 606 projects the three-dimensional dentition for the current stage of treatment onto the two-dimensional image of the patient. The projection may be made based on knowledge of the properties of the camera when the image was taken. The properties may include camera focal length and aperture, camera focusing distance, camera angle and orientation, and the distance between the camera and the patient's dentition, among other properties. Using the property information, the three-dimensional dentition is projected as a two-dimensional image in the same coordinate space as the teeth within the two-dimensional image.

The virtual dental care modules 602 may include an image generation module 608. The image generation module 608 generate error images such as the error images depicted in FIGS. 8, 9, 10, and 11. The projection from the projection module may be used to generate the error images in the image generation module 608. For example, in FIG. 8 a two-dimensional error image is generated based on the difference between the positions of the teeth in the two-dimensional image and the positions of the teeth in the three-dimensional projection. The outline shown in FIG. 8 represents the error between the location of the teeth and the 3D projection and the 2D image. In FIG. 9, a plurality of error images are shown wherein the error between the tooth position in the three-dimensional dentition model and the tooth position in the two-dimensional images are shown via an overlay over the two-dimensional image. In FIG. 10, a plurality of error images are shown wherein the error between the tooth position in the three in the three-dimensional dentition model and the tooth position in the two-dimensional images are shown via an outline of the tooth position in the digital model overlaid onto the two-dimensional images. In FIG. 11, error images may include three-dimensional generated models of the teeth in a current stage of the treatment plan next to the two-dimensional image of the patient's teeth. In FIG. 12, three-dimensional error images are shown including a first image depicting a three-dimensional view of the patient's expected tooth position based on a treatment plan side-by-side with the actual position of the patient's teeth based on the two-dimensional images.

The virtual dental care modules 602 may include an error generation module 610. The error generation module 610 quantifies the error between the positions of the teeth in the two-dimensional images and the three-dimensional projections. The error may be determined in many ways, for example, the error image in FIG. 8 may be analyzed to find the pixel difference for each tooth of the patient's dentition. The pixel difference may be the difference between, for example, a location of an edge of a tooth in the two-dimensional image and the position of a corresponding edge of the corresponding tooth in the two-dimensional projection of the three-dimensional model. The number of pixels between the corresponding edges may be determined and then based on the dimensions of the pixels within the image, the real-world distance between the corresponding edges may be determined. For example, if each pixel within an image corresponds to 100 μm and there are 10 pixels between the corresponding edges of the corresponding teeth, then the error between the expected location of the tooth at the current stage and the actual location of the tooth at the current stage from that particular projection's point of view is 1000 μm. Such analysis may be carried out from multiple projection's points of view, for example in FIGS. 8, 9, and 10, left buccal, right buccal, and anterior projections of points of view are shown. In some embodiments, the maximum error for each tooth is determined from the error in of each projection in this error may be used to generate charts for each stage for example such as shown in FIG. 12.

The virtual dental care modules 602 may include a treatment and assessment module 612. The treatment and assessment module 612 may perform an assessment of the patient's teeth or facilitate the performance of an assessment of the patient's teeth and help determine guidance and potential intervention and treatment for the patient based on the progress of the patient's treatment determined from the errors between the actual positions of the patient's teeth and the expected positions of the patient's teeth, as discussed herein. The assessment and treatment may take many forms, for example the assessment may determine whether and how far off track the patient's treatment is, as compared to the expected positions of the patient's teeth for each stage of treatment. Based on this information additional, intervention or treatment may be suggested to the patient or doctor, as discussed herein.

FIG. 7 shows a method 700 of assessing the movement of teeth of a patient. The method 700 may begin at step 702 with the initiation of orthodontic treatment of the patient's teeth. Initiation of orthodontic treatment to the patient's teeth may include many processes. In some embodiments, the patient's dentition is scanned with the three-dimensional intraoral scanner in order to generate a three-dimensional model of the patient's dentition. The three-dimensional model of the patient's dentition may include individually segmented teeth representing each of the patient's teeth of their upper and lower arches. An assessment may be made as to desired final positions of the patient's teeth based on the initial position of the patient's teeth obtained from the intraoral scan. A series of intermediate tooth positions of the patient's teeth may be generated to incrementally move the teeth through a series of stages from the initial positions towards the final positions. Dental appliances may be fabricated based on the intermediate positions of the patient's teeth in order to move the teeth from the initial positions towards the final positions. A patient then wears each of the dental appliance for a period of time, for example 10 days to two weeks, during which time the dental appliance applies forces to the patient's teeth to move the teeth from a first position at the beginning of the treatment stage towards a second position at the end of the treatment stage. Each appliance is worn in succession in order to move the patient's teeth.

However, treatment may not progress as expected. Sometimes a patient's compliance may not be as expected. A patient may not wear the dental appliances throughout the day, for example they may take them off before eating and forget to put them on after completing their meal. Such lack of compliance may lead to teeth positions lagging their expected positions. Sometimes teeth provide more or less resistance to movement than expected. This may result in teeth moving slower or faster than expected. Differences in compliance and tooth resistance may result in a treatment going off-track, such that the actual position of the patient's tooth during a given stage of treatment may deviate from the expected position to a degree that an appliance may not fit the patient's teeth or may otherwise not provide the desired movement for stage.

Doctors may monitor the progress of the patient's treatment in order to anticipate or determined that a patient's treatment has gone off-track or may be progressing towards off-track so that they can provide intervention in order to bring the treatment back on track or to generate a new treatment plan to treat the patient's teeth.

At some point during treatment the doctor may decide to assess a patient's progress, for example at each stage of the patient's treatment their doctor may request the patient to take one or more photos of the patient's teeth, guided by the artificial intelligence systems and methods discussed herein.

At step 704 the process may register the three-dimensional model of the patient's dentition at the current stage of treatment with the two-dimensional image or images of the patient's teeth. The registration and other processes that occur during step 704 may be carried out by one or more modules of the system described herein, for example by the registration module 604. The registration module 604 may register the patient's three-dimensional dentition, including the three-dimensional segmented models, to the two-dimensional images in many ways. For example, edge detection techniques may be used to determine the edges and shapes of the teeth in the two-dimensional images in order to determine which teeth are visible in the two-dimensional image and where they are located within the two-dimensional image and which teeth in the two-dimensional image correspond to particular teeth and the three-dimensional image.

At step 706 the three-dimensional image of the patient's teeth is projected into the two-dimensional image plane of one or more of the two-dimensional images. The projection module 606 may carry out the processes of step 706 by projecting the three-dimensional dentition for the current stage of treatment onto the two-dimensional image of the patient. The projection may be made based on knowledge of the properties of the camera when the image was taken. The properties may include camera focal length and aperture, camera focusing distance, camera angle and orientation, in the distance between the camera and the patient's dentition, among other properties. Using the property information, the three-dimensional dentition is projected as a two-dimensional image in the same coordinate space as the teeth within the two-dimensional image.

At step 708 in error image is generated. The image generation module 608 may generate the error images at step 708. Examples of error images are depicted in FIGS. 8, 9, 10, and 11. At step 708 the projection generated at step 706 by the projection module 606 may be used to generate the error images. For example, in generating the error image depicted in FIG. 8, a two-dimensional error image is generated based on the difference between the positions of the teeth in the two-dimensional image and the positions of the teeth in the three-dimensional projection. The outline shown in FIG. 8 represents the error between the location of the teeth and the 3D projection and the 2D image. In generating the error images depicted in FIG. 9, the error image depicted in FIG. 8 may be used to create an overlay over the two-dimensional image. The overlay may be a mask, wherein the color properties of the image are adjusted in order to highlight the positional errors of the teeth for example the mask may adjust the brightness luminance or color values of the two-dimensional image based on the error mask.

In generating the error images depicted in FIG. 10, an overlay including in outline of the teeth of the projected three-dimensional model of the current stage of treatment is overlaid onto the two-dimensional image of the patient's teeth. The outline may be opaque or translucent and may take on one or more colors for example the outline may be a white outline the black outline or another color.

In some embodiments, the overlay shown in FIG. 9 and the overlay in FIG. 10 may vary based on one or more factors. For example, the color, brightness, thickness, and other properties of the overlay may vary based on the degree of error between the expected position of the tooth and the actual position of the tooth. In some embodiments, the overlay may be a two-dimensional rendering of the three-dimensional model of the patient's teeth the patient's teeth which may be rendered on top of the two-dimensional image. The two-dimensional rendering of the three-dimensional model may be shown as partially translucent, in false color, or may include other indications to show the difference between the expected position of the patient's teeth and the actual position of the patient's teeth. In some embodiments, the overlay may be blinked on and off in order to help an observer observe the differing positions in the patient's teeth.

In generating the error images depicted in FIG. 11, a three-dimensional model of the treatment plan's current stage and a two-dimensional image of the patient's teeth may be generated. The three-dimensional model and the two-dimensional image are generated side-by-side to allow for simultaneous viewing of each image. In some embodiments, a three-dimensional model of the patient's teeth may be generated based on the positions of the teeth in the two-dimensional images of the patient. The two-dimensional images may be used as textures to provide appropriate color and shading to the three-dimensional model. This three-dimensional model of the patient's teeth may be displayed side-by-side or simultaneously with the three-dimensional model of the patient's teeth in their expected position.

In generating the error images depicted in FIG. 12, a first image depicting a three-dimensional view of the patient's expected tooth position based on a treatment plan is displayed side-by-side with the actual position of the patient's teeth based on the two-dimensional images.

In some embodiments, error images may be generated for a plurality of stages of the patient's treatment. For example, error images may be generated at each stage of the patient's treatment in order to allow a doctor to assess a patient's progress over time. In some embodiments, the error images may be presented with a user interface that includes user adjustable navigation tools such as a time selector or slider whereby the doctor may quickly move between error images of various stages of treatment. In some embodiments, the user interface may include navigation and zoom tools that allow a doctor other user to zoom in and out on the patient's error images to more closely observe the error and may allow the doctor to pan and rotate the error images in order to further facilitate assessment of the patient's dentition. In some embodiments, the various views of the error images may be synchronized with each other such that a zoom, pan, or rotation of one model or image causes a corresponding zoom, pan, or rotation of another model or image.

At step 710 the positional error of each tooth may be determined. The process of step 710 may be performed by the error generation module 610. At step 710, the error between the positions of the teeth in the two-dimensional images and the three-dimensional projections is quantified. The error may be quantified in many ways, for example, the error image in FIG. 8 may be analyzed to find the pixel difference for each tooth of the patient's dentition. The pixel difference may be the difference between, for example a location of an edge of tooth in the two-dimensional image and the position of a corresponding edge of the corresponding tooth in the two-dimensional projection. The number of pixels between the corresponding edges may be determined and then based on the dimensions of the pixels within the image the real-world distance between the corresponding edges may be determined. For example, if each pixel within an image corresponds to 100 µm and there are 10 pixels between the corresponding edges of the corresponding teeth, then the error between the expected location of the tooth at the current stage and the actual location of the tooth at the current stage from that particular projection's point of view is 1000 µm. Such analysis may be carried out from multiple projection's points of view, for example in FIGS. 8, 9, and 10, left buccal, right buccal, and anterior projections of points of view are shown. In some embodiments, the maximum error for each tooth is determined from the error in of each projection. This error may be used to generate charts for each stage, for example, such as shown in FIG. 12. In some embodiments, charts, such as those shown in FIG. 12, may be generated in a subsequent error image generation step 708.

At step 712 intervention in the patient's treatment and/or revisions to the treatment plan may be generated as discussed herein, for example with respect to FIGS. 13-18.

FIG. 8 shows differential error images of teeth of a patient for a stage of treatment. The top image is a right buccal view error image 870, the middle image is a left buccal view error image 880, and the bottom image is an anterior view error image 890. The error images 870, 880, 890 are two-dimensional error images generated based on the difference between the positions of the teeth in the two-dimensional image in the positions of the teeth in the three-dimensional projection. The error image 870, represents the error between the location of the teeth and the three-dimensional projection and the three-dimensional image, as viewed from a right buccal position. The error image shows differences in the actual position of the patient's teeth and the expected position of the patient's teeth. In the right buccal view, the right molars 841, the right bicuspids 843, the right canine 845, the incisors 847, and the left canine 842 are visible. With reference to the left canine 842, the first edge 844 of the error image 840 corresponds to the edge of the left canine 842 in the two-dimensional image. The second edge 846 corresponds to the same edge of the left canine 842 of the three-dimensional model of the patient's teeth projected in the same plane as the two-dimensional image of the patient's teeth such that the edge aligns with edge of the tooth and the three-dimensional model from the perspective of the camera that took the two-dimensional image of the patient's dentition from the right buccal side of the patient. The difference between the location of the first edge 844 and the second edge 846 quantifies the displacement of the tooth 842 in the plane of the two-dimensional image 840.

The error image 850, represents the error between the location of the teeth and the three-dimensional projection and the three-dimensional image as viewed from a left buccal position. The error image shows differences in the actual position of the patient's teeth and the expected position of the patient's teeth. In the left buccal view, the left molars 851, the left bicuspids 853, the left canine 842, the incisors 847, and the right canine 845 are visible. With reference to the left canine 842, the first edge 854 of the error image 850 corresponds to the edge of the left canine 842 in the two-dimensional image taken from the left buccal perspective. The second edge 856 corresponds to the same edge of the left canine 842 of the three-dimensional model of the patient's teeth projected in the same plane as the two-dimensional image of the patient's teeth such that the edge aligns with edge of the tooth and the three-dimensional model from the perspective of the camera that took the two-dimensional image of the patient's dentition from the left buccal side of the patient. The difference between the location of the first edge 854 and the second edge 856 quantifies the displacement of the tooth 842 in the plane of the two-dimensional image 850.

The error image 860, represents the error between the location of the teeth and the three-dimensional projection and the three-dimensional image as viewed from an anterior position. The error image shows differences in the actual position of the patient's teeth and the expected position of the patient's teeth. In the anterior view, the left canine 842, the incisors 847, and the right canine 845 are visible. With reference to the left canine 842, the first edge 864 of the error image 860 corresponds to the edge of the left canine 842 in the two-dimensional image taken from the anterior perspective. The second edge 866 corresponds to the same edge of the left canine 842 of the three-dimensional model of the patient's teeth projected in the same plane as the two-dimensional image of the patient's teeth such that the edge aligns with edge of the tooth and the three-dimensional model from the perspective of the camera that took the two-dimensional image of the patient's dentition from the left buccal side of the patient. The difference between the location of the first edge 864 and the second edge 866 quantifies the displacement of the tooth 842 in the plane of the two-dimensional image 860.

In some embodiments, the differences between the locations of the edges of the teeth in the three different image planes of the error images 840, 850, 860 may be used to directly determine the displacement of the teeth with respect to the expected location of the teeth. In some embodiments the locations of the teeth in the error images 840, 850, 860 may be used to determine the location of the teeth and three-dimensional space based on known angles and orientations of the camera and the image plane in which the two-dimensional images were taken. As discussed below, the error image may be used to highlight or otherwise indicate the difference between the expected position of the patient's teeth and the actual position of the patient's teeth.

For example, in FIG. 9 the error images are used to create a mask in the two-dimensional images of the patient's teeth. In generating the error images depicted in FIG. 9, the error image depicted in FIG. 8 is used to create a mask that generates an overlay over the two-dimensional image. The color properties of the masked area of the two-dimensional image may be altered to highlight the difference in the locations of the teeth in the two-dimensional image, as compared to the three-dimensional projection. In some embodiments the color properties of the masked portion of the images are adjusted in order to highlight the positional deviation of the teeth, for example the mask may adjust the brightness, luminance, or color values of the two-dimensional image based on the error mask.

The error images 970, 980, 990 are two-dimensional error images generated based on the difference between the positions of the teeth in the two-dimensional image in the positions of the teeth in the three-dimensional projection. In the error image 970, the mask 978 represents the error between the location of the teeth and the three-dimensional projection and the three-dimensional image as viewed from a right buccal position. In the right buccal view, the right molars 841, the right bicuspids 843, the right canine 845, the incisors 847, and the left canine 842 are visible. With reference to the left canine 842, the first edge 974 of the mask 978 corresponds to the edge of the left canine 842 in the two-dimensional image. The second edge 976 corresponds to the same edge of the left canine 842 of the three-dimensional model of the patient's teeth projected in the same plane as the two-dimensional image of the patient's teeth such that the edge aligns with edge of the tooth and the three-dimensional model from the perspective of the camera that took the two-dimensional image of the patient's dentition from the right buccal side of the patient. Thus, the overlay created by the mask 978 highlights the positional difference between the location of the first edge 974 and the second edge 976 of the tooth 842 in the plane of the two-dimensional image 970.

In the error image 980, the mask 982 represents the error between the location of the teeth and the three-dimensional projection and the three-dimensional image as viewed from a left buccal position. In the left buccal view, the left molars 851, the left bicuspids 853, the left canine 842, the incisors 847, and the right canine 845 are visible. With reference to the left canine 842, the first edge 984 of the mask 982 corresponds to the edge of the left canine 842 in the two-dimensional image taken from the left buccal perspective. The second edge 986 corresponds to the same edge of the left canine 842 of the three-dimensional model of the patient's teeth projected in the same plane as the two-dimensional image of the patient's teeth such that the edge aligns with edge of the tooth and the three-dimensional model from the perspective of the camera that took the two-dimensional image of the patient's dentition from the left buccal side of the patient. Thus, the overlay created by the mask 982 highlights the positional difference between the location of the first edge 984 and the second edge 986 highlights the positional difference between the location of the first edge 984 and the second edge 986 of the tooth 842 in the plane of the two-dimensional image 980.

In the error image 990, the mask 992 represents the error between the location of the teeth and the three-dimensional projection and the three-dimensional image as viewed from an anterior position. In the anterior view, the left canine 842, the incisors 847, and the right canine 845 are visible. With reference to the left canine 842, the first edge 994 of the mask 996 corresponds to the edge of the left canine 842 in the two-dimensional image taken from the anterior perspective. The second edge 996 corresponds to the same edge of the left canine 842 of the three-dimensional model of the patient's teeth projected in the same plane as the two-dimensional image of the patient's teeth such that the edge aligns with edge of the tooth and the three-dimensional model from the perspective of the camera that took the two-dimensional image of the patient's dentition from the left buccal side of the patient. Thus, the overlay created by the mask 992 highlights the positional difference between the location of the first edge 994 and the second edge 996 highlights the positional difference between the location of the first edge 994 and the second edge 996 of the tooth 842 in the plane of the two-dimensional image 990.

In some embodiments, the differences between the locations of the edges of the teeth in the three different image planes of the error images 840, 850, 860 may be used to directly determine the displacement of the teeth with respect to the expected location of the teeth. In some embodiments the locations of the teeth in the error images 840, 850, 860 may be used to determine the location of the teeth and three-dimensional space based on known angles and orientations of the camera and the image plane in which the two-dimensional images were taken. As discussed below, the error image may be used to highlight or otherwise indicate the difference between the expected position of the patient's teeth and the actual position of the patient's teeth.

FIG. 10 depicts outlined error images 1000, 1010, 1020 of teeth of a patient for a stage of treatment. Error image 1000 depicts a two-dimensional image of the patient's dentition from a right buccal perspective. The patient's teeth 1004 in their current position are depicted in the two-dimensional image while the outline 1002 depicts the expected position of the patient's teeth according to the current stage of the treatment plan. The outline 1002 is generated based on a projection onto the two-dimensional image plane of a three-dimensional model of the patient's teeth at the expected position according to the current stage of the treatment plan. Each visible tooth of the dentition is represented in the outline 1002. The outline represents the edges of the teeth in the projected three-dimensional model. Each tooth outline may represent an outline of a silhouette of the patient's tooth from the two-dimensional image perspective. In some embodiments a tooth outline tooth outline may be defined by an occlusal or incisal edge, the interproximal edges of the teeth, and the gingival margin.

Error image 1010 depicts a two-dimensional image of the patient's dentition from a right buccal perspective. The patient's teeth 1014 in their current position are depicted in the two-dimensional image while the outline 1012 depicts the expected position of the patient's teeth according to the current stage of the treatment plan. The outline 1012 is generated based on a projection onto the two-dimensional image plane of a three-dimensional model of the patient's teeth at the expected position according to the current stage of the treatment plan. Each visible tooth of the dentition is represented in the outline 1012.

Error image 1020 depicts a two-dimensional image of the patient's dentition from a right buccal perspective. The patient's teeth 1024 in their current position are depicted in the two-dimensional image while the outline 1022 depicts the expected position of the patient's teeth according to the current stage of the treatment plan. The outline 1022 is generated based on a projection onto the two-dimensional image plane of a three-dimensional model of the patient's teeth at the expected position according to the current stage of the treatment plan. Each visible tooth of the dentition is represented in the outline 1022.

FIG. 11 shows a side-by-side of a three-dimensional rendered teeth image 1130 of the patient's teeth in their expected position that is based on the treatment plan and a two-dimensional image 1140 of the actual position of the patient's teeth. In generating the error images depicted in FIG. 11 the three-dimensional model 1130 of the treatment plan's current stage and the two-dimensional image 1140 of the patient's teeth may be generated. The three-dimensional model 1130 and the two-dimensional image 1140 may be generated side-by-side to allow for simultaneous viewing of each image. In some embodiments, image 1140 may represent a three-dimensional model of the patient's teeth in their actual current position generated based on the positions of the teeth in the two-dimensional images of the patient. The two-dimensional images may be used as textures to provide appropriate color and shading to the three-dimensional model. This three-dimensional model of the patient's teeth may be displayed side-by-side or simultaneously with the three-dimensional model of the patient's teeth in their expected position.

FIG. 12 shows charts 1250, 1260 of differential error, sometimes referred to as the degree of on-track or off-track of the teeth for teeth of a patient for each stage of treatment. Each column 1252 in the charts 1250, 1260 represents a tooth of an arch of a patient by its corresponding tooth number. Each row 1254 in the charts 1250, 1260 represents a stage of a treatment plan. The shading in each stage for each tooth depicts the degree of variation between the expected position of the patient's tooth and that stage and the actual position of the patient's tooth in that stage for example as determined above. The legend 1256 shows that the darker the shading the more off-track the patient's tooth. The chart 1250 shows the upper jaw tracking for the patient's teeth through stage 12 of a treatment plan. As shown by block 1257, block 1258, and block 1259 tooth 2, tooth 4, and tooth 7 are deviating from their expected position more than the other teeth. However, as shown by chart 1260, by stage 20 tooth 4 merely maintains its level off-trackness, while block 1268 and block 1269 show that tooth 2 and tooth 7 have continued to get further off-track over the course of treatment a doctor may use such a chart to determine whether and how to provide guidance to or treatment intervention for the patient.

Guidance Generation

Monitoring and assessing a patient's treatment progress in order to determine appropriate treatment guidance for the patient and then providing the treatment guidance to the patient may be a difficult, expensive, and time-consuming task. The use of stage by stage tracking or other periodic tracking and tooth deviations, as discussed above, allows a doctor to at least partially simplify the task of determining the type of guidance to give a patient and providing that guidance to the patient. For example, the patient may take pictures of their dentition using the artificial intelligence guidance, as discussed above and then the deviation of each of the patient's teeth from there expected position may be determined, as also discussed above. In addition, other image-based analysis may be conducted on the captured images in order to aid in assessment of the patient's treatment progress. Based on this information and doctor provided guidance information, the patient's teeth may be assessed and appropriate guidance for continuing or modifying the patient's treatment may be provided to the doctor or the patient.

Figure 13:
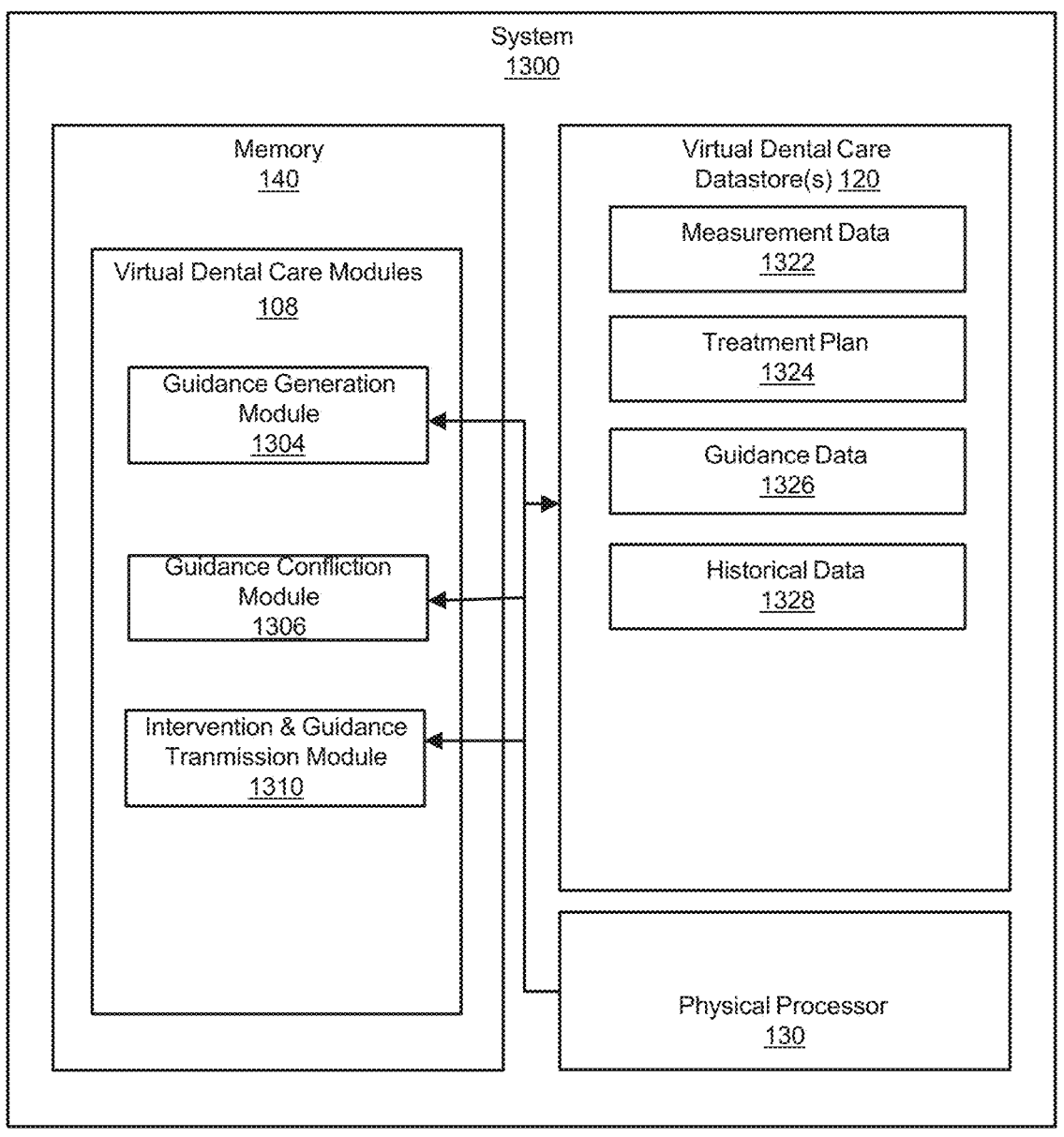
FIG. 13 shows a block diagram of an example system for providing guidance, according to embodiments herein.

FIG. 13 shows a block diagram of an example system 1300 for providing guidance. As illustrated in this figure, example system 1300 may include one or more virtual dental care modules 108 for performing one or more tasks. As will be explained in greater detail below, virtual dental care modules 108 may include a guidance generation module 1304, a guidance deconfliction module 1306, and a guidance and intervention transmission module 1308. Although illustrated as separate elements, one or more of virtual dental care modules 108 in FIG. 13 may represent portions of a single module or application.

In certain embodiments, one or more of virtual dental care modules 108 in FIG. 13 may represent one or more software applications or programs that, when executed by a computing device, may cause the computing device to perform one or more tasks. For example, and as will be described in greater detail below, one or more of virtual dental care modules 108 may represent modules stored and configured to run on one or more computing devices, such as the devices illustrated in FIG. 1A (e.g., dental patient system 102 and/or server 106). One or more of virtual dental care modules 108 in FIG. 13 may also represent all or portions of one or more special-purpose computers configured to perform one or more tasks.

As illustrated in FIG. 13, example system 1300 may also include one or more virtual dental care datastore(s) 120, such as measurement data 1322, treatment plan data 1324, guidance information 1326, and historical data 1323. Virtual dental care datastore(s) 120 may comprise any type or form of data or information.

The virtual dental care datastore(s) 120 may include measurement data 1322. Measurement data may include data, such as the error data discussed above with respect to FIG. 6. For example, the measurement data may include error data generated based on the differences between the position and orientation of the teeth and a two-dimensional image of a patient's teach and a give stage of treatment and a three-dimensional projection of the three-dimensional model of the patient's teeth for the given stage of treatment. The measurement data 1322 may include differential position and rotational angles in three-dimensional space for each of the teeth in the patient's dentition. In some embodiments, the measurement data may also include the presence and absence of attachments and other orthodontic devices on the patient's dentition. In some embodiments, the measurement data 1322 may include information regarding the fit of the aligner on the patient's teeth. For example, the measurement data 1322 may include the tooth receiving cavities of a dental appliance that do not properly fit on the patient's teeth. In some embodiments, the measurement data 1322 may include a magnitude of the and/or improper fit of the dental appliance such as the distance between and includes all or part of an incisal surface of a tooth receiving cavity and a corresponding occlusal or incisal surface of a corresponding tooth.

In some embodiments, the measurement data 1322 may include the above-described data for each of the stages of the treatment plan and may further include rates of change and other information determined based on the differences between the patient's teeth and orthodontic appliances used for treatment over multiple stages of the treatment plan. In some embodiments, the measurement data 1322 includes per-tooth deviations from the current treatment plan in the anterior, left buccal, and right buccal views, as discussed above. In some embodiments, the measurement data 1322 may include measure distances and angles of the deviation between the expected and actual positions and orientations of each tooth. In some embodiments, the measurement data 1322 may include both a distance and direction of the deviation of the tooth. For example, the error information may include data indicating that a tooth is not tracking in intrusion and is 0.25 mm from the expected position in the treatment plan.

The virtual dental care datastore(s) 120 may include treatment plan data 1324. The treatment plan data 1324 may include the positions and orientations of each of the patient's teeth for each stage of a treatment plan 1514. In some embodiments, the positions and orientations of the teeth may be stored as three-dimensional positional locations and angular orientations of each tooth and the patient's upper and lower arches. In some embodiments the positions and orientations of the patient's teeth may be stored as a collection of three-dimensional segmented models of the patient's upper and lower arches for each stage of treatment. In some embodiments, the treatment plan data may include other information such as the location of attachments on the patient's teeth, and other orthodontic devices such as wire and bracket braces, elastics, temporary anchorage devices, and other orthodontic devices.

The virtual dental care datastore(s) 120 may include guidance information 1326. The guidance information 1326 may include a doctor's guidance template data 1512. The doctor's guidance template data 1512 may include information in threshold values that the doctor uses for tracking a treatment plan and determining potential variations in treatment and guidance to provide to the patient based on the threshold values. For example, the thresholds values could be as specific as if the central incisors deviate from the treatment plan by 0.75 mm, the guidance should be sent to the patient to schedule a new appointment, if one of the central incisors deviation between 0.5-0.75 mm from the treatment plan, then further deviations should be watched, if the central incisor deviations increase over a period of 2 months should result in a new appointment, if the central incisor deviations are between 0.25 to 0.5 mm, then the patient should be given guidance to wear the current set of aligners for an additional week, and central incisor deviations less than 0.25 mm can be considered "on-track". Other thresholds may specify that teeth marked "Do No Move" according to the treatment plan should not deviate from their treatment position and any deviation greater than 0.25 mm should result in an appointment.

The guidance information 1326 may also include case-by-case guidance 1516 based on one or more of the particular treatment plan and the particular patient. For example, a treatment plan with a particularly out of place tooth may have case specific thresholds that are higher or lower than the thresholds in the doctor's guidance template or, for example, the patient may be missing one or more teeth and accordingly the case-by-case guidance data may omit any thresholds related to the missing teeth or may include patient specific thresholds related to closing a gap formed by the missing tooth.

The virtual dental care datastore(s) 120 may include historical data 1323. The historical data 1323 may include information related to guidance previously provided to the patient and historical measurement information 1524. The use of historical data 1323 may allow guidance thresholds to be written with a temporal frame of reference. For example, the guidance thresholds may include things such as if a condition worsens over a certain number of weeks, then provide the particular type of guidance.

The modules 1102 may include a guidance generation module 1304. The guidance generation module receives the measurement data 1322, the treatment plan data 1322, guidance information 1326, and the historical data 1323 and uses this information to apply the guidance to the patient's current dental occlusion, such as the position of the patient's teeth, with respect to the expected occlusion in the treatment plan. For example, the guidance may include a threshold such as if the incisor's position as determined by the measurement data 1322 is greater than 0.5 mm from the expected position, then send guidance to the patient to schedule an appointment, or by incorporating historical data, if the deviation of the incisor's position increases by more than 0.1 in two consecutive stages then send guidance to the patient to schedule an appointment. In some embodiments, for example in which treatment plans include the use of attachments, the guidance generation module may generate guidance to the patient, or the doctor based on the absence or detachment of an attachment.

The guidance may also include guidance related to the timing of switching aligners for example guidance to where the dental liner for an additional amount of time before changing to the aligner for the next stage of treatment or to change to the next stage at an earlier time. The guidance may also include instructions to wear a retainer or switch from an aligner to a retainer. Other interventions are guidance may include instructions on how to use and when to use chewies, when to schedule an orthodontic follow-up appointment, and other guidance. The guidance may also include instructions to the doctor or example to contact the patient for follow-up appointment or to guide the next steps of treatment and suggested interventions for consideration by the doctor.

In some embodiments, conflicting guidance or duplicative guidance may be given to the patient based on differences in one or more of the guidance template and the case-by-case guidance. For example, a patient may have multiple issues more than one of which may result in providing guidance to the patient to schedule an appointment while other guidance may suggest to the that the patient immediately see the doctor. In such cases the guidance deconfliction module 1306 may determine that the patient should only receive guidance to immediately see the doctor rather than to both immediately see the doctor and schedule an appointment. In some embodiments, the threshold may indicate that guidance should be provided for the patient to use a chewie on the first premolar and another threshold may indicate that guidance should be provided for the patient to use a chewie on the second premolar on the same side. Here, only one chewie is needed, accordingly, the guidance may be deconflicted to indicate that the patient should use a single chewie on the first and second premolars. In this way the guidance the confliction module 1306 can prevent the system from providing conflicting or confusing guidance to the patient.

The modules 1102 may include a guidance and intervention transmission module 1308. The guidance and intervention transmission module 1308 may transmit guidance or intervention information to one or more of the patient and the doctor. The guidance or intervention information may be sent via many means. For example, the guidance may be sent via text message, email, smart phone or browser-based application notifications, automated telephone calls, calendar invites, or other forms of messaging and communication. In some embodiments the guidance may include both text and audiovisual information, such as a video or image showing the proper use of a chewie.

Figure 14:
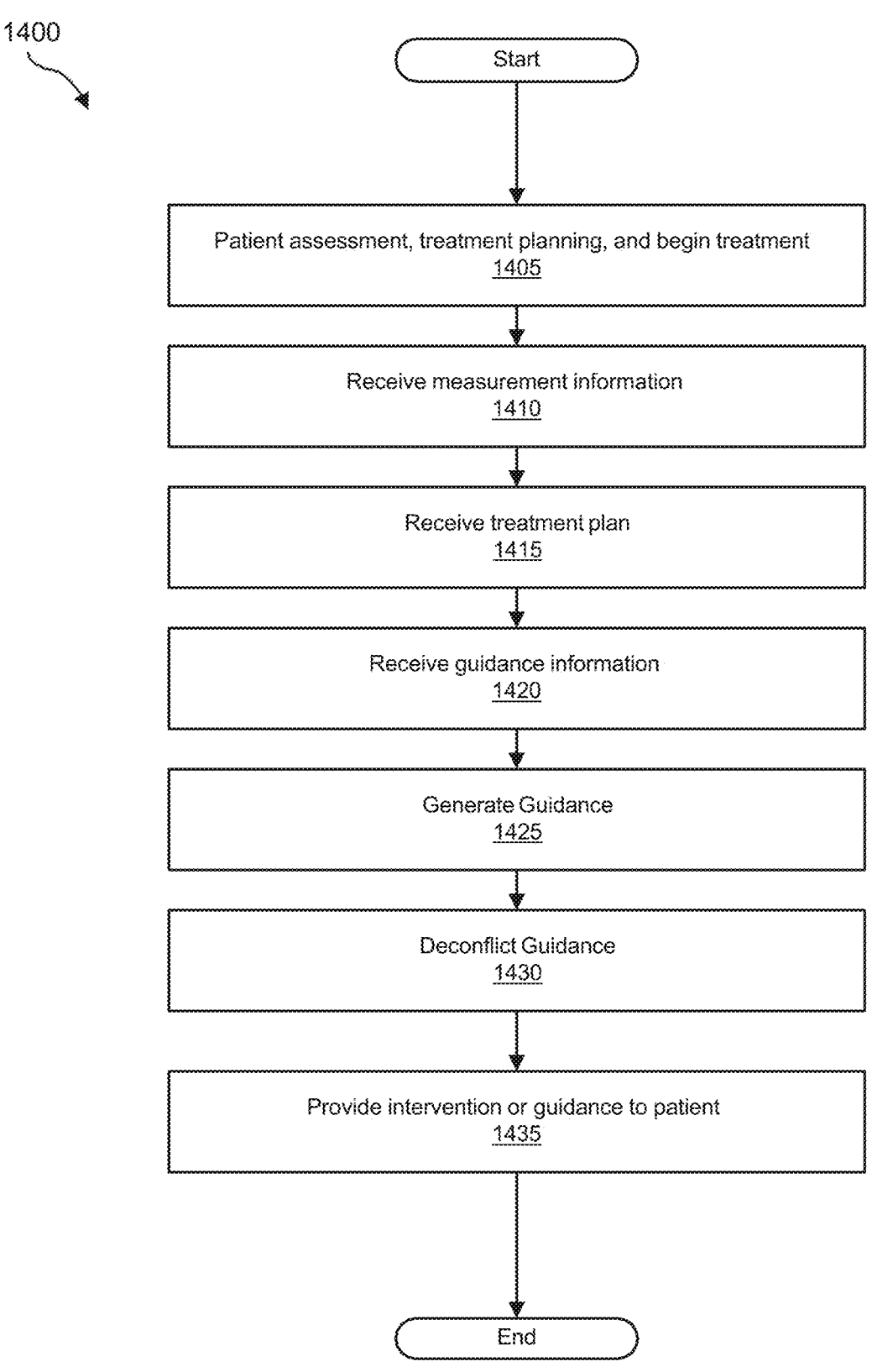
FIG. 14 shows a method of providing guidance, according to embodiments herein, according to embodiments herein.
Figure 15:
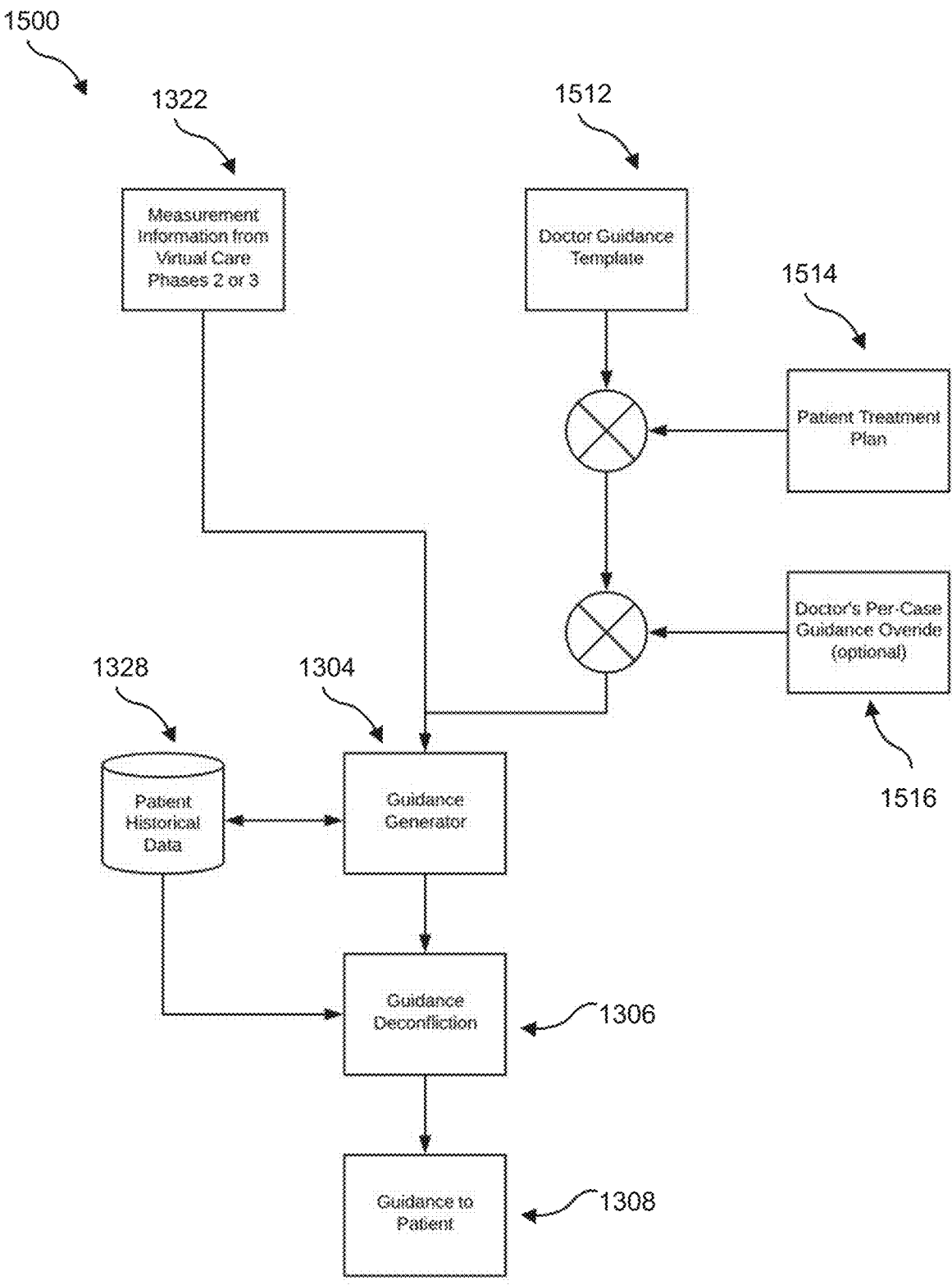
FIG. 15 shows a process flow diagram for generating and providing orthodontic guidance to a patient, according to embodiments herein.

FIG. 14 is a flow diagram of an exemplary computer-implemented method 1400 for determining and providing guidance. FIG. 15 is a process and information flow diagram 1350 of the exemplary computer-implemented method 1300 for determining and providing guidance. The steps and information flow shown in FIGS. 14 and 15 may be performed by any suitable computer-executable code and/or computing system, including the system(s) illustrated in FIGS. 1 and 13. In one example, each of the steps shown in FIGS. 14 and 15 may represent an algorithm whose structure includes and/or is represented by multiple sub-steps, examples of which will be provided in greater detail below.

With reference to FIGS. 14 and 15, at step 1405 the patient assessment, treatment planning, and the beginning of treatment may occur, for example as discussed above with reference to step 2002 of FIG. 20. At step 1410 the guidance generation module 1304 receives measurement data 1322. The measurement data 1322 may include two-dimensional images received from a patient over a communication network. In some embodiments, measurement data 1322 may include error data 628 received from, for example, the error module 610.

At step 1415 the guidance generation module 1304 receives the treatment plan data 1514. In some embodiments, guidance generation module 1304 receives the treatment plan data 1514 from the treatment planning system or module.

At step 1420 the guidance generation module 1304 receives the guidance information the guidance information may include both the doctor's guidance template information 1514 and the case-by-case guidance information 1516.

At step 1425 the guidance generation module 1304 uses the received information from step 1420 and applies the received guidance to the patient's current dental occlusion based on the measurement data 1322 and the treatment plan data 1514. As discussed above, the guidance may include guidance related to the timing of switching aligners for example guidance to where the dental liner for an additional amount of time before changing to the aligner for the next stage of treatment or to change to the next stage at an earlier time based on thresholds as discussed above. The guidance may also include instructions to switch from wearing an aligner to a wearing retainer. Other interventions are guidance may include instructions on how to use and when to use chewies, when to schedule an orthodontic follow-up appointment, and other guidance. In some embodiments, for example in which treatment plans include the use of attachments, the guidance generation module may generate guidance to the patient, or the doctor based on the absence or detachment of an attachment.

At step 1430 the guidance the confliction module 1306 the conflicts the guidance provided by the guidance generation module 1304. For example, the confliction module 1306 may determine that the patient should only receive guidance to immediately see the doctor rather than to both immediately see the doctor and schedule an appointment. In some embodiments, the threshold may indicate that guidance should be provided for the patient to use a chewie on the first premolar and another threshold may indicate that guidance should be provided for the patient to use a chewie on the second premolar on the same side. Here, only one chewie is needed, accordingly, the confliction module 1306 may indicate that the patient should use a single chewie on the first and second premolars. In this way, the system may be prevented from providing conflicting or confusing guidance to the patient.

At step 1435 the guidance and intervention transmission module 1308 may transmit guidance or intervention information to one or more of the patient and the doctor. At step 1435 the guidance or intervention information may be sent via many means. For example, the guidance may be sent via text message, email, smart phone or browser-based application notifications, automated telephone calls, calendar invites, or other forms of messaging and communication. In some embodiments the guidance may include both text and audiovisual information, such as a video or image showing the proper use of a chewie.

In some embodiments, the guidance generation module 1304 may indicate that the treatment intervention may be desired, for example, when the positions of the teeth have deviated to the point where a new treatment planning process should begin to generate new stages of treatment to move the teeth from a current position towards the desired final position.

Photo Based Treatment Refinement

The practice of medicine is rapidly evolving toward tele-medicine—the remote treatment of patients. By using the above described systems and methods a doctor may remotely assess the patient's treatment progress and in the rare cases when the patient's progress becomes so off-track as to warrant a revised treatment plan, the images captured using the artificial intelligence guidance, discussed above, along with the segmented dental scans generated at the initiation of treatment may be used to prescribe a secondary order for an off-track patient using only their primary treatment plan data and a set of orthodontic photographs taken by the patient with a phone camera, without rescanning the patient or calling the patient back into the office.

Figure 16:
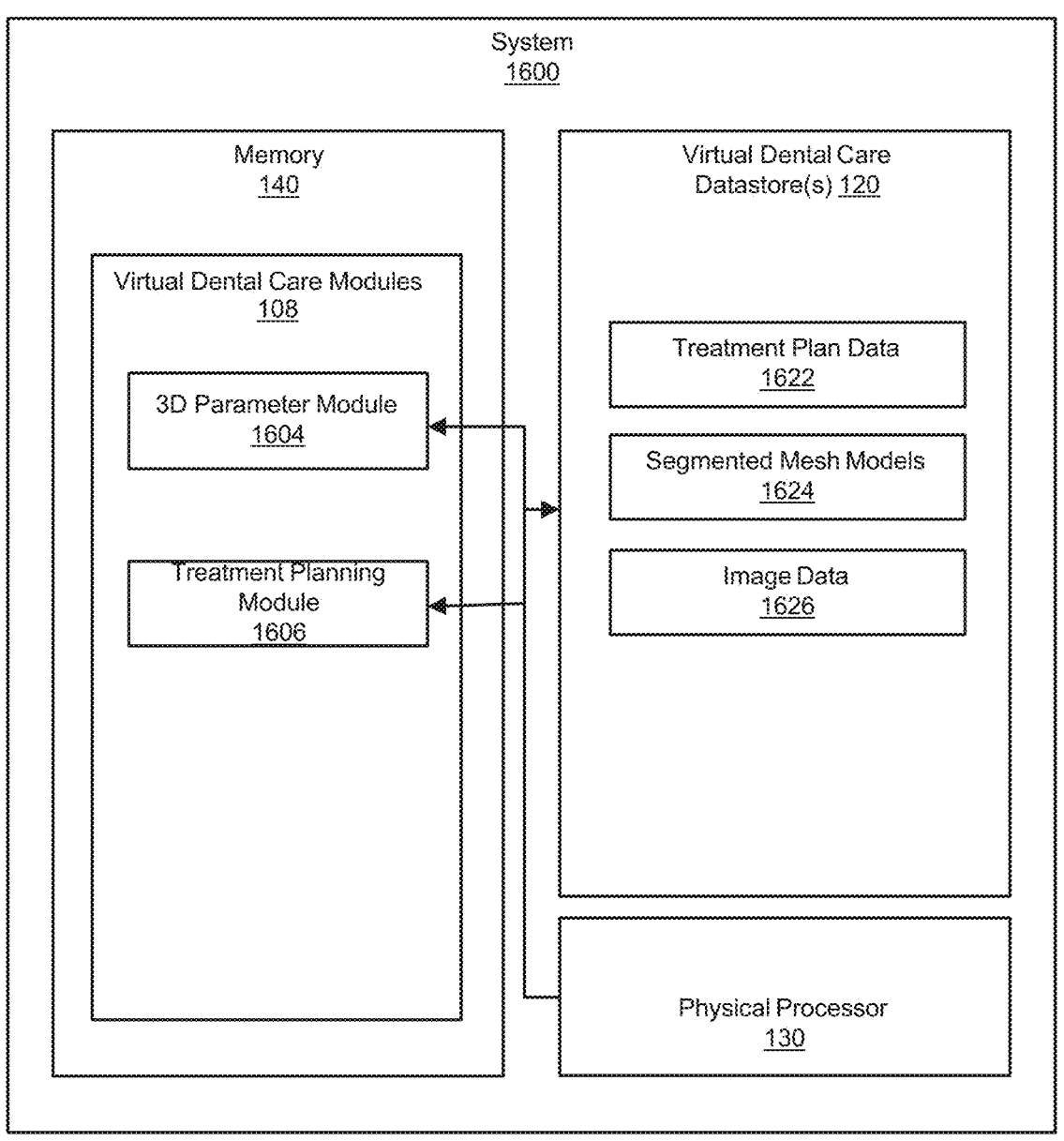
FIG. 16 shows a block diagram of an example system for off-track treatment planning, according to embodiments herein.

FIG. 16 shows a block diagram of an example system for off-track treatment planning. As illustrated in this figure, example system 1600 may include one or more virtual dental care modules 108 for performing one or more tasks. As will be explained in greater detail below, virtual dental care modules 108 may include a three-dimensional parameterization module 1604 and a treatment planning module 1606. Although illustrated as separate elements, one or more of virtual dental care modules 108 in FIG. 16 may represent portions of a single module or application.

In certain embodiments, one or more of virtual dental care modules 108 in FIG. 16 may represent one or more software applications or programs that, when executed by a computing device, may cause the computing device to perform one or more tasks. For example, and as will be described in greater detail below, one or more of virtual dental care modules 108 may represent modules stored and configured to run on one or more computing devices, such as the devices illustrated in FIG. 1A (e.g., dental patient system 102 and/or server 106). One or more of virtual dental care modules 108 in FIG. 16 2 may also represent all or portions of one or more special-purpose computers configured to perform one or more tasks.

As illustrated in FIG. 16, example system 1600 may also include one or more virtual dental care datastore(s) 120, such as treatment plan data 1622, segmented mesh models 1624, and image data 1626. Virtual dental care datastore(s) 120 may include one or more datastores configured to store any type or form of data or information.

Virtual dental care datastore(s) 120 may include treatment plan data 1622. The treatment plan data 1622 may include the positions and orientations of each of the patient's teeth for each stage of a treatment plan. In some embodiments, the positions and orientations of the teeth may be stored as three-dimensional positional locations and angular orientations of each tooth and the patient's upper and lower arches. In some embodiments the positions and orientations of the patient's teeth may be stored as a collection of three-dimensional segmented models of the patient's upper and lower arches for each stage of treatment. In some embodiments, the treatment plan data may include other information such as the location of attachments on the patient's teeth, and other orthodontic devices such as wire and bracket braces, elastics, temporary anchorage devices, and other orthodontic devices.

Virtual dental care datastore(s) 120 may include segmented mesh models 1624. In some embodiments the segmented mesh models of the patient's teeth may be stored separately from the treatment plan data. The segmented mesh models may include three-dimensional mesh models of each of the patient's teeth.

Virtual dental care datastore(s) 120 may include image data 1626. The image data 1626 may include a two-dimensional image data, such as the two-dimensional image data captured using the artificial intelligence guidance, as discussed above.

The three-dimensional parameterization module 1604 receives the treatment plan data 1622 and the image data 1626 and uses the data to generate a three-dimensional model of the patient's dentition at a current position by determining the appropriate positions for the patient's teeth and placing the segmented tooth models from the treatment plan data into those positions. The three-dimensional parameterization model 1604 may use information such as the error data discussed above in order to determine the three-dimensional positions of the patient's teeth. In some embodiments, in addition to the three buccal images discussed above, upper, and lower arch occlusal photos may also be used in order to determine the three-dimensional positions of the patient's teeth. Various methods may be used to align the three-dimensional models of the patient's teeth with the two-dimensional images of the patient's teeth. For example, in some embodiments a differential rendering algorithm may be used to align the teeth, or an expectation-maximization algorithm may be used to match the position and orientation of the three-dimensional models of the patient's teeth with a corresponding locations and orientations of the teeth in the two-dimensional image. The three-dimensional parameterization module 1604 may output a new segmented dental mesh model of the patient's teeth in their current positions.

The treatment planning module 1606 may use the new segmented dental mesh model output by the three-dimensional parameterization module 1604 along with the treatment plan information in order to generate a revised treatment plan to move the patient's teeth from the new current position to the desired final position. In some embodiments, the revised treatment plan may move the teeth to a different, new desired final position.

Figure 17:
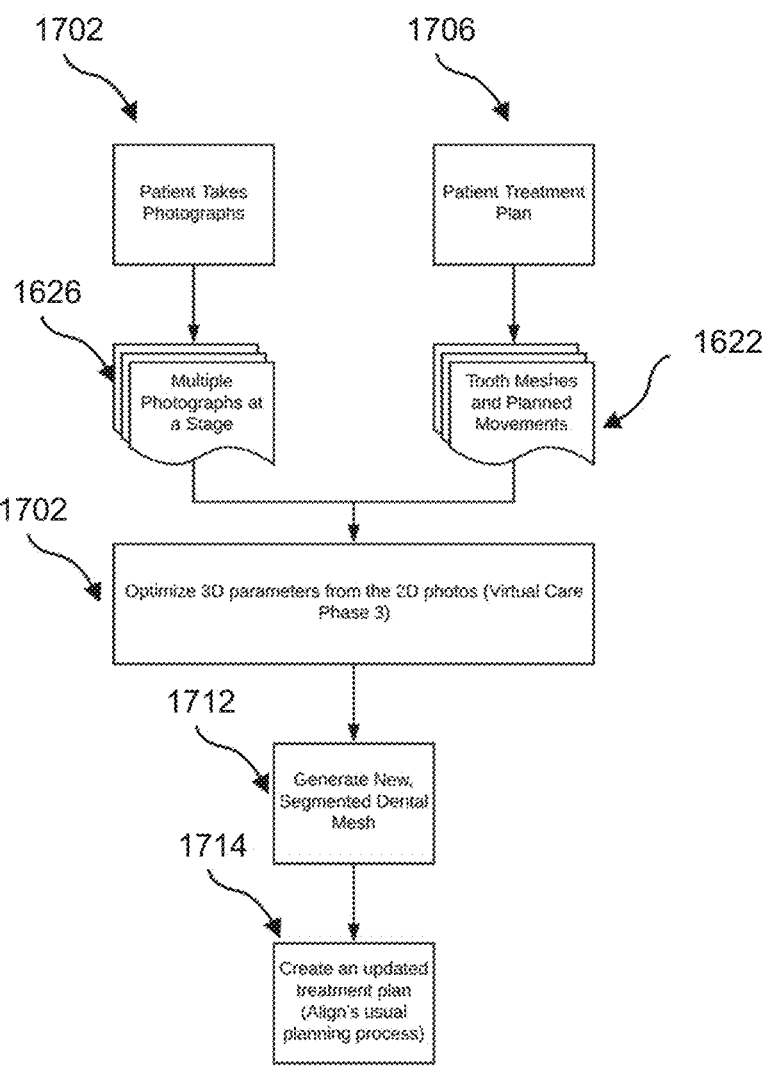
FIG. 17 shows a method of generating a treatment plan for off-track treatment of a patient, according to embodiments herein.

FIG. 17 is a flow diagram of an exemplary computer-implemented method 17 300 for photo-based treatment refinement. The steps shown in FIG. 17 may be performed by any suitable computer-executable code and/or computing system, including the system(s) illustrated in FIGS. 1 and 16. In one example, each of the steps shown in FIG. 17 may represent an algorithm whose structure includes and/or is represented by multiple sub-steps, examples of which will be provided in greater detail below.

At step 1702 a patient takes two-dimensional photographs 1626 of their teeth. The photographs may include a left buccal, a right buccal, an anterior, and upper and lower occlusal the use of the patient's teeth. The capturing of the two-dimensional photographs 1626 may be guided by the artificial intelligence guidance system discussed above.

At step 1706 a treatment plan is gathered. The treatment plan may be gathered or generated, as discussed above. The treatment plan 1622 may include tooth meshes and the planned movements of the teeth for the initial treatment of the patient's dentition.

At step 1710 the three-dimensional parameterization module 1604 receives the treatment plan data 1622 and the image data 1626 and uses the data to generate a three-dimensional model of the patient's dentition at a current position by determining the appropriate positions for the patient's teeth and placing the segmented tooth models from the treatment plan data into those positions. The three-dimensional parameterization model 1604 may use information such as the error data discussed above in order to determine the three-dimensional positions of the patient's teeth. In some embodiments, in addition to the three buccal images discussed above, upper, and lower arch occlusal photos may also be used in order to determine the three-dimensional positions of the patient's teeth. Various methods may be used to align the three-dimensional models of the patient's teeth with the two-dimensional images of the patient's teeth. For example, in some embodiments a differential rendering algorithm may be used to align the teeth, or an expectation-maximization algorithm may be used to match the position and orientation of the three-dimensional models of the patient's teeth with a corresponding locations and orientations of the teeth in the two-dimensional image.

At step 1712 the three-dimensional parameterization module 1604 may output a new segmented dental mesh model of the patient's teeth in their current positions. FIG. 18 shows segmented mesh teeth arches generated from existing scans of a patient's teeth and 2D images for a patent's teeth using the algorithms discussed above, according to embodiments herein. The alignment 1810 shows the alignment of a mesh depicting expected position of the patient's teeth 1804 according to the treatment plan with a mesh of the actual current position of the patient's teeth 1802 generated using the segmented three-dimensional models of the patient's teeth and the two-dimensional images captured by the patient.

The alignment 1820 shows the alignment of a mesh depicting the alignment of the three-dimensional mesh models 1806 of the patient's teeth from the treatment plan with a mesh of the actual current position of the patient's teeth 1802 generated using the segmented three-dimensional models of the patient's teeth and the two-dimensional images captured by the patient. The close agreement between the two models shows that the algorithms discussed above produce meshes of suitable accuracy for use in treatment planning without rescanning the patient's teeth.

At step 1714 treatment planning module 1606 may use the new segmented dental mesh model output by the three-dimensional parameterization module 1604 along with the treatment plan information in order to generate a revised treatment plan to move the patient's teeth from the new current position to the desired final position. In some embodiments, the revised treatment plan may move the teeth to a different, new desired final position.

The updated treatment plan may be used to fabricate new dental appliances to move the patient's teeth from the new current position to a desired final position.

Treatment Based Photo Guidance

As discussed herein, to perform virtual orthodontic care, virtual dental care, and/or other remote medicine, the practitioner may wish to visually inspect the patient's dentition. For example, the practitioner may wish to inspect the patient's progress during a treatment plan, diagnose possible issues, and modify the treatment plan as needed. A dental practitioner or the treatment data 138, including a treatment plan, may be used to determine clinically relevant views from which image the patient's teeth.

Using the determined views, as described herein, the systems and methods provided in this disclosure may utilize artificial intelligence or other guidance means to provide a patient with guidance on taking clinically relevant orthodontic photos. The systems and methods provided in this disclosure may improve the functioning of a computing device by more efficiently acquiring image data, which may further reduce storage requirements and network bandwidth. In addition, the systems and methods provided herein may improve the field of virtual medicine by improving the functional capabilities of remote devices.

Figure 21:
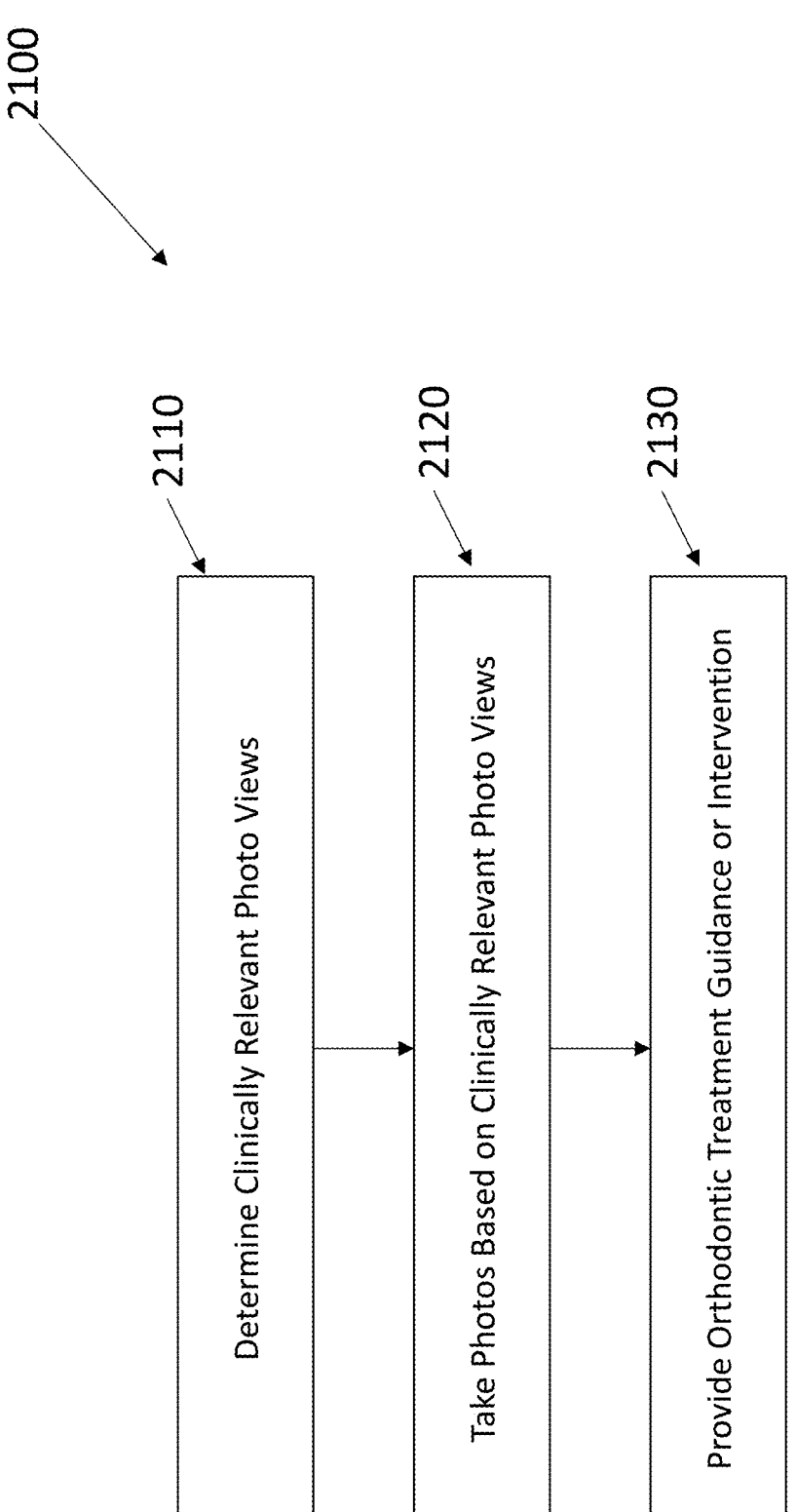
FIG. 21 depicts a method for acquiring and using clinically relevant images of a patient's teeth.

FIG. 21 depicts a method 2100 for acquiring and using clinically relevant images of a patient's teeth. The method may include determining clinically relevant photos views for taking clinically relevant images of the patient's teeth, taking the clinically relevant images of the patient's teeth including providing guidance for the capture of the images, and providing orthodontic treatment guidance or intervention based on the clinically relevant images.

At block 2110 clinically relevant photo or image view are determined. The clinically relevant photo or image views may include one or more of the teeth to be included in the image, a position, an orientation, and a field of view from which to take in image of a patient's dentition. In some embodiments, a dental professional such as the treating orthodontist or dentist may request one or more of the patient's teeth the image from one or more directions. For example, a dental professional may indicate that the upper central incisors included in the images and that the images be acquired from the occlusal direction and the buccal direction. In some embodiments, the treatment plan may be used in order to determine the views from which to take the clinically relevant images.

Figures 22A, 22B, 22C, 22D:
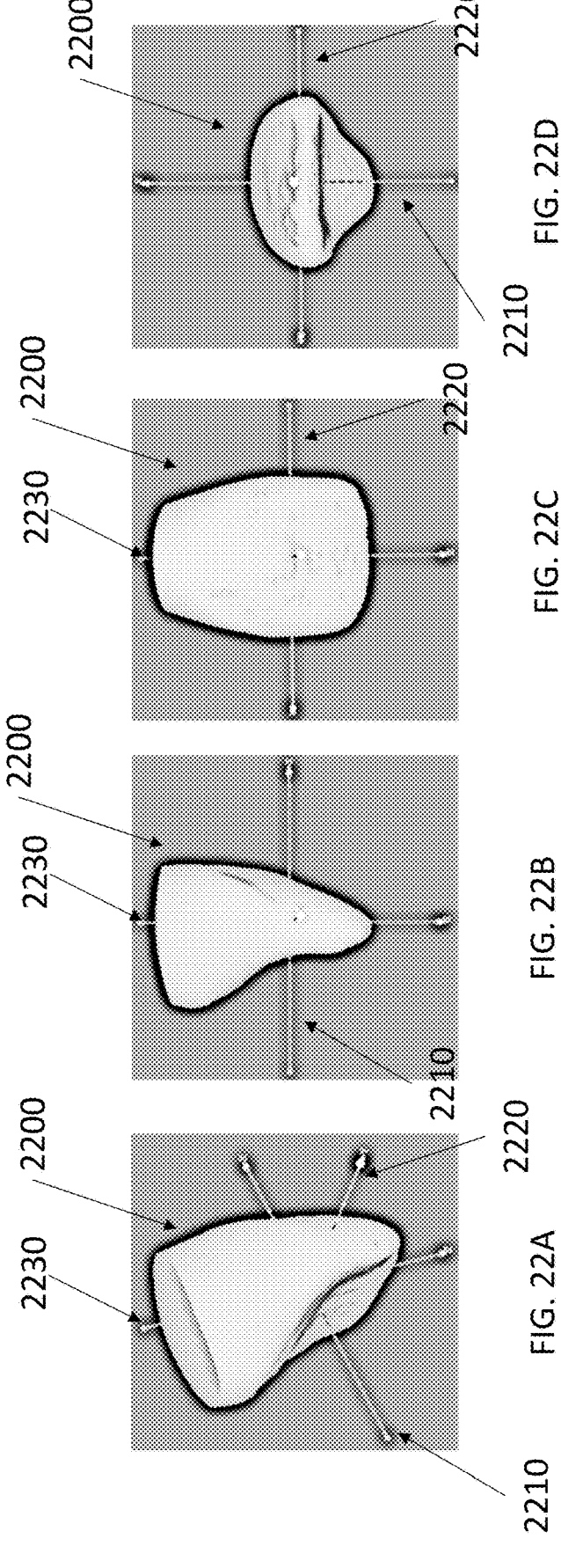
FIGS. 22A, 22B, 22C, and 22D depict teeth and an example set of axes about which a teeth may move, in accordance with some embodiments.

During orthodontic treatment, clinically relevant images are taken in order to capture the movement of the patient's teeth. In order to capture the movement of the patient's teeth the images should be taken from one or more views that are normal to the plane in which the teeth are translating or parallel to the axis about which the patient's teeth are rotating. FIGS. 22A-D depict an example set of axes about which a teeth may move. FIG. 22A depicts an isometric view of an upper central incisor. The mesial-distal axis 2220 may extend through the width of the tooth along the mesial-distal direction and may be referred to as the y-axis, the buccal-lingual axis 2210 may extend through the thickness of the tooth along the buccal-lingual direction and may be referred to as the x-axis, and the occlusal-gingival axis 2230 may extend through the length tooth along the occlusal-gingival direction and may be referred to as the z-axis. In some embodiments the x-axis, y-axis and z-axis are orthogonal to each other.

When a tooth movement for a treatment stage includes translation in the XZ plane shown in FIG. 22B or along the x-axis or z-axis, or includes rotation about the y-axis, then the clinically relevant image of the patient's teeth may include an image taken normal to or displaced from the XZ plane or along the y-axis. When a tooth movement for a treatment stage includes translation in the XY plane shown in FIG. 22D or along the x-axis or y-axis, or includes rotation about the z-axis, then the clinically relevant image of the patient's teeth may include an image taken normal to or displaced from the XY plane or along the z-axis. When a tooth movement for a treatment stage includes translation in the YZ plane shown in FIG. 22C or along the y-axis or z-axis, or includes rotation about the x-axis, then the clinically relevant image of the patient's teeth may include an image taken normal to or displaced from the YZ plane or along the x-axis.

As discussed above, a dental professional may select views for capturing the movement of the patient's teeth. In some embodiments, the treatment plan may be used in order to determine the views from which to take the clinically relevant images. As discussed elsewhere herein, a treatment plan may include a series of stages for moving the patient's teeth from an initial position towards a final position. Each treatment stage may include an initial position of the treatment stage and a final position of the treatment stage. The final position of a first treatment stage may correspond to the initial position of a second treatment stage. At block 2210, the virtual dental care system 106 may use the treatment data 138, including the treatment plan data, to determine which teeth are moving during a particular stage of treatment and in which directions and about which axes they are translating and/or rotating. Based on this determination, one or more views for capturing the movement of the patient's teeth may be determined. In some embodiments, determine which teeth are moving may include determining which teeth are scheduled to make a difficult movement during a treatment stage, such as a rotating canine, an intruding tooth, or an extruding tooth.

In some embodiments, the one or more views may be selected from one or more predetermined views. For example, the predetermined views may be a buccal view of the patient's teeth from an buccal direction centered along the patient's midline, one or more buccal views of the patient's teeth taken from a location offset on one side or the other from the patient's midline, for example offset 15°, 30°, 45°, 60°, 75°, and 90° offset to the left and right of the patient's midline, and one or more occlusal views taken from an occlusal position to capture the occlusal or incisal surfaces of the patient's teeth.

In some of embodiments the one or more views may be selected from one or more predetermined views of each of the patient's teeth. For example, the treatment plan may indicate that one or more teeth are moving or rotating in excess of a threshold amount during a particular stage of the treatment plan. The selected views may include a buccal image and an occlusal image of each of the teeth that are moving or rotating in excess of the threshold amount during the stage of the treatment plan. In some embodiments, a single image may capture more than one tooth accordingly views of adjacent teeth that may be within a field of view of an image being system such as a camera may be consolidated. For example, the virtual dental care system 106 after determining the desired clinically relevant views for each tooth may then consolidate one or more views for example of the one or more views of adjacent teeth. For example, in some embodiments of the left and right upper central incisors may be moving during a particular treatment stage accordingly, the virtual dental care system 106 may initially determine that buccal images and occlusal images for both the right and left central upper incisors should be captured, however at a consolidation step the two buccal images may be consolidated into a single buccal image and the two occlusal images may be consolidated into a single occlusal image that captures of teeth.

In some embodiments, at block 2110, patient specific views are determined. For example, the predicted tooth movement during a treatment stage may be assessed and based on the predicted tooth movement a patient specific view may be determined. Although the tooth movements in a treatment plan may be expressed as vectors in the three axes discussed above, not all tooth movements are along one of the orthogonal axes. In some embodiments, the movement of each tooth during each stage of the treatment may be determined and then a position and orientation of the clinically relevant view of the tooth from a perspective that is normal to the tooth movement may be determined in this view or perspective may be a patient specific view for capturing the patient's teeth for the treatment stage.

Figures 23A, 23B, 23C, 23D, 23E:
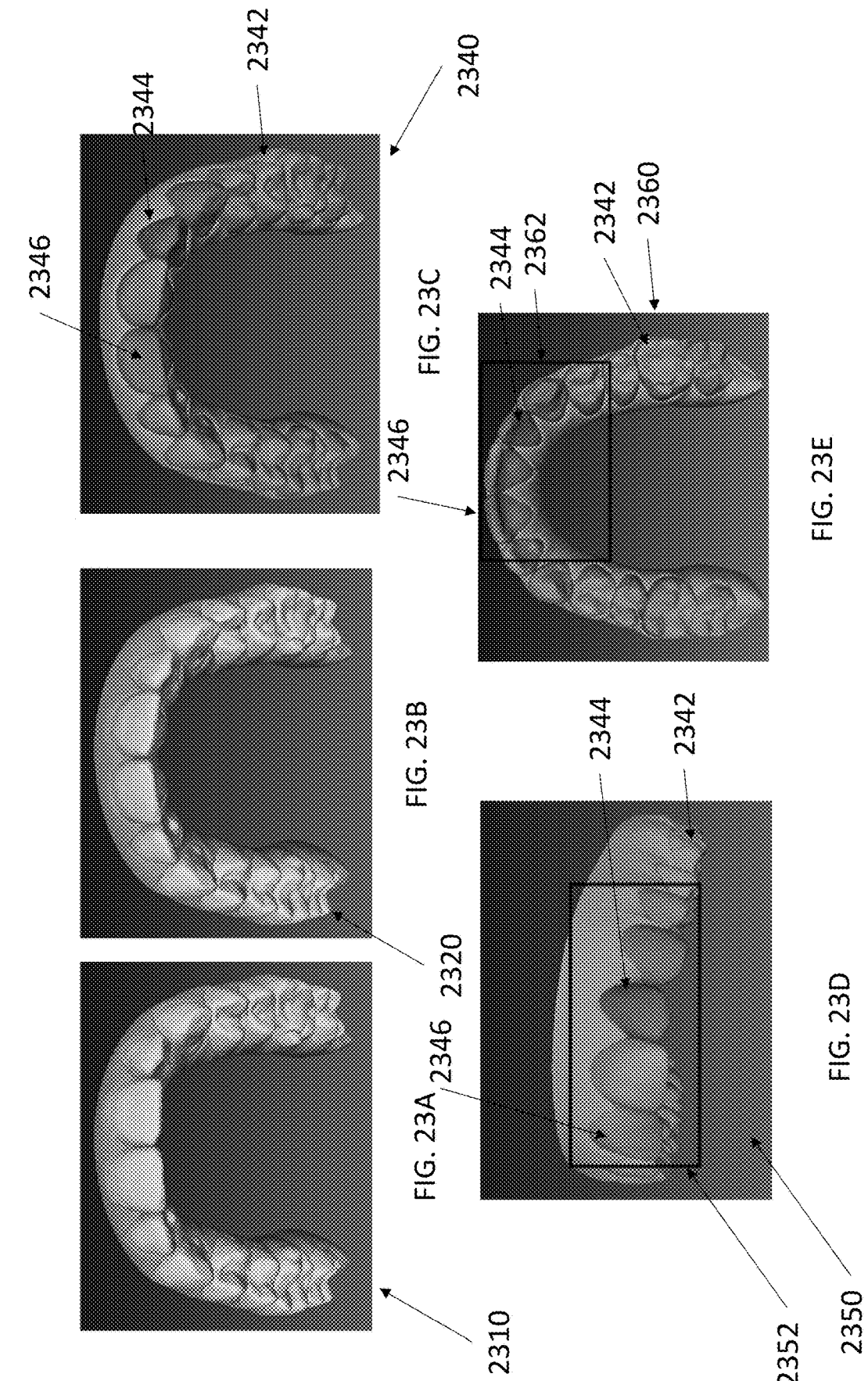
FIGS. 23A 23B, and 23C depict images of a patient's dentition determined based on a treatment plan, in accordance with some embodiments.
FIGS. 23D and 23E depict models of the patient's dentition and clinically relevant views for capturing the movement of the patient's teeth, in accordance with some embodiments.

FIGS. 23A-C depict images determined based on a treatment plan. FIG. 23A depicts a model 2310 of the patient's dentition for a first stage of treatment. The model may include a three-dimensional model formed by connected vertices that depicted the surface of the patient's teeth. FIG. 23B depicts a similar model 2320 of the patient's dentition for a second stage of treatment. FIG. 23C depicts a three-dimensional model 2340 of the patient's teeth for that is color-coded or shaded based on the vertex wise distance between the surfaces of the patient's teeth and the first and second stages. The darker shaded teeth for example tooth 2344 and tooth 2346 are moving during this stage of treatment while tooth 2342 is not moving or moving very little during the state of treatment. At block 210 the virtual dental care system 106 may be determined that tooth 2344 and tooth 2346 should be imaged in order to assess the patient's dentition. Based on this determination the virtual dental care system 106 may determine one or more clinically relevant views.

FIG. 23D depicts a model 2350 of the patient's dentition and a first clinically relevant view 2352 for capturing the movement of the patient's teeth 2344 and 2346. View 2352 is a buccal view of the patient's teeth and may capture movement in mesial-distal directions and the occlusal-gingival directions. FIG. 23E depicts a model 2360 which may be the same model 2350 of the patient's dentition and a second clinically relevant view 2362 for capturing the movement of the patient's teeth 2344 and 2346. View 2362 is an occlusal view of the patient's teeth and may capture movement in the buccal-lingual direction and the mesial distal direction. View 2362 may also capture rotation of the teeth about the occlusal-gingival axis.

After determining the clinically relevant views the process may proceed to block 2120. At block 2120 guidance may be provided to acquire photos based on the clinically relevant views. The guidance may be provided as discussed herein with respect to FIGS. 2-5 in the 'Intelligent Photo Guidance' section. For example, one or more systems described herein may receive a clinically relevant view from the virtual dental care system 106 and an image data stream from a camera. For example, camera module 204 may receive image data stream 222 from camera 132 of system 200 or another camera in communication with system 200.

The one or more systems may then compare an image from the image data stream to the clinically relevant view, for example using an artificial intelligence scheme, one or more binary classifications and one or more categorical classifications from the image data stream. For example, AI module 206 may determine binary classifications 224 and categorical classifications 226 from image data stream 222. Based on a determination, the system may provide feedback as to how to change the view provided in the data stream or how to otherwise move the camera to capture the clinically relevant view. In some embodiments, the feedback may include guidance prompts which may refer to audio, visual, and/or haptic prompts that may provide instruction to a user. Examples of guidance prompts may include, without limitation, overlays on a device screen, text notifications, oral instructions, a tone or other sound, a vibration, etc.

Guidance prompts 228 may include instructions for the user to manipulate system 200 into a configuration that may take images satisfying requirements 234. For example, the instructions may include an instruction to adjust a camera view of the camera to include a particular body part in the camera view, such as moving the camera closer or farther, pan/tilt/zoom the camera, change an angle, tracking or otherwise moving the camera, etc. The instructions may include an instruction to insert or remove a particular appliance. The instructions may also include an instruction to move a particular body part, such as open or close the patient's bite, open the patient's jaw wider, etc. The instruction may include an instruction to adjust one or more camera settings, such as zoom, focus, turn on/off a flash, etc.

When the system determines that the data stream includes the clinically relevant view the system may automatically capture the image or may instruct the user to provide input to capture the image. This process may repeat for each of the medically relevant views.

After capturing the clinically relevant views the process may proceed to block 2130. At block 2130 orthodontic treatment guidance or intervention may be provided. The guidance or intervention may be provided as discussed herein with respect to FIGS. 13-18 in the "Guidance Generation" and "Photo Based Treatment Refinement" sections. For example, a guidance generation module 1304 may receive guidance and apply the received guidance to the patient's current dental occlusion based on measurement data 1322 and the treatment plan data 1514. As discussed herein, the guidance may include guidance related to the timing of switching aligners for example guidance to where the dental liner for an additional amount of time before changing to the aligner for the next stage of treatment or to change to the next stage at an earlier time based on thresholds as discussed above. The guidance may also include instructions to switch from wearing an aligner to a wearing retainer. Other interventions are guidance may include instructions on how to use and when to use chewies, when to schedule an orthodontic follow-up appointment, and other guidance. In some embodiments, for example in which treatment plans include the use of attachments, the guidance generation module may generate guidance to the patient, or the doctor based on the absence or detachment of an attachment.

The guidance may be transmitted to one or more of the patient and the doctor or later revision to the patient. For example, the guidance may be sent via text message, email, smart phone or browser-based application notifications, automated telephone calls, calendar invites, or other forms of messaging and communication. In some embodiments the guidance may include both text and audiovisual information, such as a video or image showing the proper use of a chewie.

Intervention may include revisions to the treatment plan. For example, if it is determined that the patient's orthodontic treatment is off track to a sufficient degree that a new treatment plan should be developed, then the clinically relevant images may be used to generate a three-dimensional model of the patient's current dentition. The current dentition may then be used to develop an updated treatment plan for moving the teeth from their current position towards a position. For example, as shown and described with respect to FIGS. 16 and 17, herein.

Virtual Care—Aligner Fit

As described herein, using tele-orthodontics or a virtual care system, patients may take their own photographs of their own dentition and send these photographs to their doctor. The doctor may then assess patients' progress toward treatment goals. As described herein, the doctor may assess patients' actual dentitions via photographs and the virtual care system. However, patients and doctors may wish to use tele-orthodontics for assessing orthodontic appliances, such as assessing "aligner fit" for assessing the quality of seating of an aligner on the patient's dentition.

When using a clear aligner for a patient's treatment, aspects of aligner fit may be visible from photographs taken by the patient. As described further herein, the present disclosure provides systems and methods for remote assessment of the quality of seating for clear aligners.

FIG. 24 is a flow diagram of an exemplary computer-implemented method 2400 for assessing the quality of seating for clear aligners. The steps shown in FIG. 24 may be performed by any suitable computer-executable code and/or computing system, including the systems illustrated in FIGS. 1A, 1B, 1C, 1D, 1E, 2, 3, 4, 6, 13, 15, 16, 19, and 20. In one example, each of the steps shown in FIG. 24 may represent an algorithm whose structure includes and/or is represented by multiple sub-steps, examples of which will be provided in greater detail below.

As illustrated in FIG. 24, at step 2410 one or more of the systems described herein may receive image data of a patient's dentition and an orthodontic appliance. For example, example system 200 in FIG. 2, system 600 in FIG. 6, system 1300 in FIG. 13, or system 1600 in FIG. 16 may receive image data, similar to image data stream 222, image data 232, 2D images 624, etc., of the patient's dentition. As described herein, the patient may take their own photographs of their own dentition using their own devices (e.g., using dental patient system 102. This image data may include image data captured with the patient wearing their orthodontic appliance, which may be a clear aligner. The patient may capture the image data during a middle or near an end of a treatment stage, although the patient may capture the image data at any time.

The systems described herein may perform step 2410 in a variety of ways. In one example, the image data may be uploaded from a patient's device to another computing device, such as a server or other computer (e.g., virtual dental care system 106 and/or dental professional system 150) for further processing. In other examples, the image data may be processed on the patient's device.

FIG. 25A illustrates image data 2500 of a patient's dentition including an orthodontic appliance.

At step 2420 one or more of the systems described herein may identify, from the image data, the orthodontic appliance. For example, example system 200 in FIG. 2, system 600 in FIG. 6, system 1300 in FIG. 13, or system 1600 in FIG. 16 may identify the orthodontic appliance, which may be a clear aligner.

The systems described herein may perform step 2420 in a variety of ways. In one example, semantic segmentation may be performed to classify each pixel of the image data into one of a plurality of classes. For example, a probability of belonging to each class may be determined for each pixel of the image data. Each pixel may be classified based on which class the pixel has the highest probability of matching. The classes may include, for example, a tooth class indicating the patient's teeth (which may be portions of the teeth not covered by the orthodontic appliance), a gap class indicating a gap between the orthodontic appliance and a corresponding gingival edge, and a space class indicating a space between an incisal edge of the orthodontic appliance and an incisal edge of a corresponding tooth. In other examples, other classes may be used, such as a gum class corresponding to the patient's gums, an appliance class, other classes, etc. By performing the semantic segmentation, pixels corresponding to the orthodontic appliance (e.g., the gap class and the space class) may be distinguished from pixels corresponding to the patient's dentition without the appliance (e.g., the tooth class). As will be described further below, the gap class and/or the space class may also correspond to a misalignment.

FIG. 25B illustrates mask data 2502 in which semantic segmentation has identified a gap region 2510, a space region 2520, and a space region 2530. FIG. 25C illustrates image data 2504 in which mask data 2502 is overlaid onto image data 2500 to better show how semantic segmentation may produce mask data 2502.

In some examples, the semantic segmentation may be performed using machine learning. For example, neural network 406 or other machine learning scheme may be used to perform the semantic segmentation. In some example, neural network 406 may be trained to perform the semantic segmentation by inputting an image data set, such as a training data set, for semantic segmentation by the neural network. This training data set may have a corresponding mask data set of the desired semantic segmentation. The training may further include computing an error between an output of the neural network (e.g. by performing the semantic segmentation) and the mask data set corresponding to the image data set and adjusting the parameters of neural network 406 to reduce the error.

In other examples, identifying the orthodontic appliance may include evaluating a color value of each pixel to identify a tooth portion without the orthodontic appliance and a tooth portion with the orthodontic appliance. For instance, a threshold-based segmentation may be used in which color thresholds corresponding to teeth, gums, appliances over teeth, and appliances without teeth, may be used to classify each pixel.

In other examples, identifying the orthodontic appliance may include applying one or more filters to the image data to determine a tooth edge and an orthodontic appliance edge. For instance, an edge-based segmentation may be used to find edges and regions inside the edges may be designated by class based on color features, such as the color threshold described herein.

At step 2430 one or more of the systems described herein may calculate a misalignment height of a misalignment of the orthodontic appliance with respect to the patient's dentition. For example, example system 200 in FIG. 2, system 600 in FIG. 6, system 1300 in FIG. 13, or system 1600 in FIG. 16 may calculate the misalignment height of a misalignment determined using the identified orthodontic appliance.

The systems described herein may perform step 2430 in a variety of ways. In one example, the misalignment height may be calculated from a pixel height of the misalignment, which may be identified from misalignment classes such as the gap class and/or the space class as described herein. For instance, in FIGS. 25B and/or 25C, the pixel heights of gap region 2510, space region 2520, and space region 2530 may be calculated.

As seen in FIGS. 25B and 25C, each misalignment may occur in several regions, such as across a horizontal range. In such examples, the misalignment height may be calculated from aggregating the plurality of identified misalignments. For example, for space region 2530, the various heights across space region 2530 may be determined. The misalignment height for space region 2530 may be calculated using, for example, an 80th percentile value of the various heights, although in other examples, other percentiles may be used. Alternatively, other aggregating functions, such as average, mode, etc. may be used. The misalignment height for gap region 2510 and space region 2520 may be similarly calculated.

Although pixel heights may be used, in some examples, the pixel height may be converted to a standard unit of measurement. For instance, the patient's doctor may prefer to see misalignment heights measured in millimeters or other unit of measurement. To convert the pixel measurement, a reference object, such as an incisor, may be identified from the image data. The reference object may be selected based on having an available known measurement. For example, the incisor measurement may be obtained from a treatment plan for the patient. A pixel height of the incisor may be determined from the image data and used with the incisor measurement to determine a conversion factor between pixels and the standard unit of measurement (e.g., mm). The misalignment height may be converted from pixels to the standard unit of measurement using the conversion factor.

In some examples, the misalignment height may be further adjusted. The semantic segmentation may overestimate misalignment regions. In such instances, a thickness offset may be subtracted from the calculated misalignment height to simulate a material thickness of the orthodontic appliance. The thickness offset may be obtained from a treatment plan for the patient.

In some examples, the misalignment height may be tracked over time using image data over time. For example, the patient may capture image data at various points in time during a treatment stage. A misalignment trend may be identified from the tracked misalignment heights. The misalignment trend may be defined as a general trend (e.g., increasing, decreasing, etc.), as height deltas (e.g., the changes in misalignment height at each point in time), or by actual misalignment height values.

At step 2440 one or more of the systems described herein may determine whether the misalignment height satisfies a misalignment threshold. For example, example system 200 in FIG. 2, system 600 in FIG. 6, system 1300 in FIG. 13, or system 1600 in FIG. 16 may determine whether the misalignment height satisfies a misalignment threshold. The misalignment threshold may be predetermined or precalculated, such as based on patient history and/or other empirical data, or may be manually selected, such as by the patient's doctor.

The systems described herein may perform step 2440 in a variety of ways. In one example, the misalignment threshold may comprise a plurality of misalignment thresholds. For example, 0.5 mm space may not be desirable but may not necessarily require corrective action and therefore may be set as a low threshold. However, 0.75 mm may require corrective action and thus be set as a high threshold. In some examples, if the misalignment trend is tracked, the misalignment threshold may include a misalignment trend threshold. For example, if the misalignment height remains at 0.75 mm at multiple points of time, corrective action may be needed.

At step 2450 one or more of the systems described herein may, in response to satisfying the misalignment threshold, provide a notification. For example, example system 200 in FIG. 2, system 600 in FIG. 6, system 1300 in FIG. 13, or system 1600 in FIG. 16 may provide a notification if the misalignment threshold is satisfied.

The systems described herein may perform step 2450 in a variety of ways. In one example, the notification may include a message or other notification to the patient's doctor. In some examples, the notification may include providing a visual overlay of the misalignment, as in FIG. 25C. In some examples, a color may indicate a type of misalignment.

In some examples, if the misalignment threshold includes a plurality of misalignment thresholds, the notification may include increasing priority based on the threshold met. For each range between the multiple thresholds, a different color may be used when depicting mask data. For example, if the misalignment height is below a low threshold, a low priority color such as blue may be used. If between the low and high threshold, a low warning color such as yellow may be used. If exceeding the high threshold, a high warning color such as orange may be used.

In some examples, the misalignment threshold may include the misalignment trend threshold. The notification may be provided in response to satisfying the misalignment trend threshold.

The virtual care system described herein may allow the patient's doctor to remotely monitor aspects of the patient's treatment progression. Such monitoring may allow early intervention when needed. For example, in response to the notification, the doctor may recommend certain actions or changes in treatment, such as repeating a particular stage, using chewable object (e.g., "chewies") to help the patient chew the orthodontic appliance into place, restart treatment, etc.

Computing System

FIG. 19 is a block diagram of an example computing system 1910 capable of implementing one or more of the embodiments described and/or illustrated herein. For example, all or a portion of computing system 1910 may perform and/or be a means for performing, either alone or in combination with other elements, one or more of the steps described herein (such as one or more of the steps illustrated in FIGS. 3, 7, 14, 15, 17, 21, 24, 26, 29, 32, and 35). All or a portion of computing system 1910 may also perform and/or be a means for performing any other steps, methods, or processes described and/or illustrated herein.

Computing system 1910 broadly represents any single or multi-processor computing device or system capable of executing computer-readable instructions. Examples of computing system 1910 include, without limitation, workstations, laptops, client-side terminals, servers, distributed computing systems, handheld devices, or any other computing system or device. In its most basic configuration, computing system 1910 may include at least one processor 1914 and a system memory 1916.

Processor 1914 generally represents any type or form of physical processing unit (e.g., a hardware-implemented central processing unit) capable of processing data or interpreting and executing instructions. In certain embodiments, processor 1914 may receive instructions from a software application or module. These instructions may cause processor 1914 to perform the functions of one or more of the example embodiments described and/or illustrated herein.

System memory 1916 generally represents any type or form of volatile or non-volatile storage device or medium capable of storing data and/or other computer-readable instructions. Examples of system memory 1916 include, without limitation, Random Access Memory (RAM), Read Only Memory (ROM), flash memory, or any other suitable memory device. Although not required, in certain embodiments computing system 1910 may include both a volatile memory unit (such as, for example, system memory 1916) and a non-volatile storage device (such as, for example, primary storage device 1932, as described in detail below). In one example, one or more of virtual dental care modules 108 from FIG. 1A may be loaded into system memory 1916.

In some examples, system memory 1916 may store and/or load an operating system 1940 for execution by processor 1914. In one example, operating system 1940 may include and/or represent software that manages computer hardware and software resources and/or provides common services to computer programs and/or applications on computing system 1910. Examples of operating system 1940 include, without limitation, LINUX, JUNOS, MICROSOFT WINDOWS, WINDOWS MOBILE, MAC OS, APPLE'S IOS, UNIX, GOOGLE CHROME OS, GOOGLE'S ANDROID, SOLARIS, variations of one or more of the same, and/or any other suitable operating system.

In certain embodiments, example computing system 1910 may also include one or more components or elements in addition to processor 1914 and system memory 1916. For example, as illustrated in FIG. 19, computing system 1910 may include a memory controller 1918, an Input/Output (I/O) controller 1920, and a communication interface 1922, each of which may be interconnected via a communication infrastructure 1912. Communication infrastructure 1912 generally represents any type or form of infrastructure capable of facilitating communication between one or more components of a computing device. Examples of communication infrastructure 1912 include, without limitation, a communication bus (such as an Industry Standard Architecture (ISA), Peripheral Component Interconnect (PCI), PCI Express (PCIe), or similar bus) and a network.

Memory controller 1918 generally represents any type or form of device capable of handling memory or data or controlling communication between one or more components of computing system 1910. For example, in certain embodiments memory controller 1918 may control communication between processor 1914, system memory 1916, and I/O controller 1920 via communication infrastructure 1912.

I/O controller 1920 generally represents any type or form of module capable of coordinating and/or controlling the input and output functions of a computing device. For example, in certain embodiments I/O controller 1920 may control or facilitate transfer of data between one or more elements of computing system 1910, such as processor 1914, system memory 1916, communication interface 1922, display adapter 1926, input interface 1930, and storage interface 1934.

As illustrated in FIG. 19, computing system 1910 may also include at least one display device 1924 coupled to I/O controller 1920 via a display adapter 1926. Display device 1924 generally represents any type or form of device capable of visually displaying information forwarded by display adapter 1926. Similarly, display adapter 1926 generally represents any type or form of device configured to forward graphics, text, and other data from communication infrastructure 1912 (or from a frame buffer, as known in the art) for display on display device 1924.

As illustrated in FIG. 19, example computing system 1910 may also include at least one input device 1928 coupled to I/O controller 1920 via an input interface 1930. Input device 1928 generally represents any type or form of input device capable of providing input, either computer or human generated, to example computing system 1910. Examples of input device 1928 include, without limitation, a keyboard, a pointing device, a speech recognition device, variations, or combinations of one or more of the same, and/or any other input device.

Additionally or alternatively, example computing system 1910 may include additional I/O devices. For example, example computing system 1910 may include I/O device 1936. In this example, I/O device 1936 may include and/or represent a user interface that facilitates human interaction with computing system 1910. Examples of I/O device 1936 include, without limitation, a computer mouse, a keyboard, a monitor, a printer, a modem, a camera, a scanner, a microphone, a touchscreen device, variations, or combinations of one or more of the same, and/or any other I/O device.

Communication interface 1922 broadly represents any type or form of communication device or adapter capable of facilitating communication between example computing system 1910 and one or more additional devices. For example, in certain embodiments communication interface 1922 may facilitate communication between computing system 1910 and a private or public network including additional computing systems. Examples of communication interface 1922 include, without limitation, a wired network interface (such as a network interface card), a wireless network interface (such as a wireless network interface card), a modem, and any other suitable interface. In at least one embodiment, communication interface 1922 may provide a direct connection to a remote server via a direct link to a network, such as the Internet. Communication interface

1922 may also indirectly provide such a connection through, for example, a local area network (such as an Ethernet network), a personal area network, a telephone or cable network, a cellular telephone connection, a satellite data connection, or any other suitable connection.

In certain embodiments, communication interface 1922 may also represent a host adapter configured to facilitate communication between computing system 1910 and one or more additional network or storage devices via an external bus or communications channel. Examples of host adapters include, without limitation, Small Computer System Interface (SCSI) host adapters, Universal Serial Bus (USB) host adapters, Institute of Electrical and Electronics Engineers (IEEE) 1394 host adapters, Advanced Technology Attachment (ATA), Parallel ATA (PATA), Serial ATA (SATA), and External SATA (eSATA) host adapters, Fiber Channel interface adapters, Ethernet adapters, or the like. Communication interface 1922 may also allow computing system 1910 to engage in distributed or remote computing. For example, communication interface 1922 may receive instructions from a remote device or send instructions to a remote device for execution.

In some examples, system memory 1916 may store and/or load a network communication program 1938 for execution by processor 1914. In one example, network communication program 1938 may include and/or represent software that enables computing system 1910 to establish a network connection 1942 with another computing system (not illustrated in FIG. 19) and/or communicate with the other computing system by way of communication interface 1922. In this example, network communication program 1938 may direct the flow of outgoing traffic that is sent to the other computing system via network connection 1942. Additionally or alternatively, network communication program 1938 may direct the processing of incoming traffic that is received from the other computing system via network connection 1942 in connection with processor 1914.

Although not illustrated in this way in FIG. 19, network communication program 1938 may alternatively be stored and/or loaded in communication interface 1922. For example, network communication program 1938 may include and/or represent at least a portion of software and/or firmware that is executed by a processor and/or Application Specific Integrated Circuit (ASIC) incorporated in communication interface 1922.

As illustrated in FIG. 19, example computing system 1910 may also include a primary storage device 1932 and a backup storage device 1933 coupled to communication infrastructure 1912 via a storage interface 1934. Storage devices 1932 and 1933 generally represent any type or form of storage device or medium capable of storing data and/or other computer-readable instructions. For example, storage devices 1932 and 1933 may be a magnetic disk drive (e.g., a so-called hard drive), a solid-state drive, a floppy disk drive, a magnetic tape drive, an optical disk drive, a flash drive, or the like. Storage interface 1934 generally represents any type or form of interface or device for transferring data between storage devices 1932 and 1933 and other components of computing system 1910. In one example, virtual dental care datastore(s) 120 from FIG. 1A may be stored and/or loaded in primary storage device 1932.

In certain embodiments, storage devices 1932 and 1933 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 1932 and 1933 may also include other similar structures or devices for allowing computer software, data, or other computer-readable instructions to be loaded into computing system 1910. For example, storage devices 1932 and 1933 may be configured to read and write software, data, or other computer-readable information. Storage devices 1932 and 1933 may also be a part of computing system 1910 or may be a separate device accessed through other interface systems.

Many other devices or subsystems may be connected to computing system 1910. Conversely, all of the components and devices illustrated in FIG. 19 need not be present to practice the embodiments described and/or illustrated herein. The devices and subsystems referenced above may also be interconnected in different ways from that shown in FIG. 19. Computing system 1910 may also employ any number of software, firmware, and/or hardware configurations. For example, one or more of the example embodiments disclosed herein may be encoded as a computer program (also referred to as computer software, software applications, computer-readable instructions, or computer control logic) on a computer-readable medium. The term "computer-readable medium," as used herein, generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The computer-readable medium containing the computer program may be loaded into computing system 1910. All or a portion of the computer program stored on the computer-readable medium may then be stored in system memory 1916 and/or various portions of storage devices 1932 and 1933. When executed by processor 1914, a computer program loaded into computing system 1910 may cause processor 1914 to perform and/or be a means for performing the functions of one or more of the example embodiments described and/or illustrated herein. Additionally or alternatively, one or more of the example embodiments described and/or illustrated herein may be implemented in firmware and/or hardware. For example, computing system 1910 may be configured as an Application Specific Integrated Circuit (ASIC) adapted to implement one or more of the example embodiments disclosed herein.

FIG. 20 is a block diagram of an example network architecture 2000 in which client systems 2010, 2020, and 2030 and servers 2040 and 2045 may be coupled to a network 2050. As detailed above, all or a portion of network architecture 2000 may perform and/or be a means for performing, either alone or in combination with other elements, one or more of the steps disclosed herein (such as one or more of the steps illustrated in FIGS. 3, 7, 14, 15, 17, 21, 24, 26, 29, 32, and 35). All or a portion of network architecture 2000 may also be used to perform and/or be a means for performing other steps and features set forth in the instant disclosure.

Client systems 2010, 2020, and 2030 generally represent any type or form of computing device or system, such as example computing system 1910 in FIG. 19. Similarly, servers 2040 and 2045 generally represent computing devices or systems, such as application servers or database servers, configured to provide various database services and/or run certain software applications. Network 2050 generally represents any telecommunication or computer network including, for example, an intranet, a WAN, a LAN, a PAN, or the Internet. In one example, client systems 2010, 2020, and/or 2030 and/or servers 2040 and/or 2045 may include all or a portion of system 100 from FIG. 1A or the other systems and devices disclosed herein.

As illustrated in FIG. 20, one or more storage devices 2060(1)-(N) may be directly attached to server 2040. Similarly, one or more storage devices 2070(1)-(N) may be directly attached to server 2045. Storage devices 2060(1)-(N) and storage devices 2070(1)-(N) generally represent any type or form of storage device or medium capable of storing data and/or other computer-readable instructions. In certain embodiments, storage devices 2060(1)-(N) and storage devices 2070(1)-(N) may represent Network-Attached Storage (NAS) devices configured to communicate with servers 2040 and 2045 using various protocols, such as Network File System (NFS), Server Message Block (SMB), or Common Internet File System (CIFS).

Servers 2040 and 2045 may also be connected to a Storage Area Network (SAN) fabric 2080. SAN fabric 2080 generally represents any type or form of computer network or architecture capable of facilitating communication between a plurality of storage devices. SAN fabric 2080 may facilitate communication between servers 2040 and 2045 and a plurality of storage devices 2090(1)-(N) and/or an intelligent storage array 2095. SAN fabric 2080 may also facilitate, via network 2050 and servers 2040 and 2045, communication between client systems 2010, 2020, and 2030 and storage devices 2090(1)-(N) and/or intelligent storage array 2095 in such a manner that devices 2090(1)-(N) and array 2095 appear as locally attached devices to client systems 2010, 2020, and 2030. As with storage devices 2060(1)-(N) and storage devices 2070(1)-(N), storage devices 2090(1)-(N) and intelligent storage array 2095 generally represent any type or form of storage device or medium capable of storing data and/or other computer-readable instructions.

In certain embodiments, and with reference to example computing system 1910 of FIG. 19, a communication interface, such as communication interface 1922 in FIG. 19, may be used to provide connectivity between each client system 2010, 2020, and 2030 and network 2050. Client systems 2010, 2020, and 2030 may be able to access information on server 2040 or 2045 using, for example, a web browser or other client software. Such software may allow client systems 2010, 2020, and 2030 to access data hosted by server 2040, server 2045, storage devices 2060(1)-(N), storage devices 2070(1)-(N), storage devices 2090(1)-(N), or intelligent storage array 2095. Although FIG. 20 depicts the use of a network (such as the Internet) for exchanging data, the embodiments described and/or illustrated herein are not limited to the Internet or any particular network-based environment.

In at least one embodiment, all or a portion of one or more of the example embodiments disclosed herein may be encoded as a computer program and loaded onto and executed by server 2040, server 2045, storage devices 2060(1)-(N), storage devices 2070(1)-(N), storage devices 2090(1)-(N), intelligent storage array 2095, or any combination thereof. All or a portion of one or more of the example embodiments disclosed herein may also be encoded as a computer program, stored in server 2040, run by server 2045, and distributed to client systems 2010, 2020, and 2030 over network 2050.

As detailed above, computing system 1910 and/or one or more components of network architecture 2000 may perform and/or be a means for performing, either alone or in combination with other elements, one or more steps of any of the methods disclosed herein.

Although the examples herein are described with respect to orthodontic care, in other implementations the remote care may include any other medical care that may be conducted via external photography.

While the foregoing disclosure sets forth various embodiments using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered example in nature since many other architectures can be implemented to achieve the same functionality.

In some examples, all or a portion of example system 100 in FIG. 1A may represent portions of a cloud-computing or network-based environment. Cloud-computing environments may provide various services and applications via the Internet. These cloud-based services (e.g., software as a service, platform as a service, infrastructure as a service, etc.) may be accessible through a web browser or other remote interface. Various functions described herein may be provided through a remote desktop environment or any other cloud-based computing environment.

In various embodiments, all or a portion of example system 100 in FIG. 1A may facilitate multi-tenancy within a cloud-based computing environment. In other words, the software modules described herein may configure a computing system (e.g., a server) to facilitate multi-tenancy for one or more of the functions described herein. For example, one or more of the software modules described herein may program a server to enable two or more clients (e.g., customers) to share an application that is running on the server. A server programmed in this manner may share an application, operating system, processing system, and/or storage system among multiple customers (i.e., tenants). One or more of the modules described herein may also partition data and/or configuration information of a multi-tenant application for each customer such that one customer cannot access data and/or configuration information of another customer.

According to various embodiments, all or a portion of example system 100 in FIG. 1A may be implemented within a virtual environment. For example, the modules and/or data described herein may reside and/or execute within a virtual machine. As used herein, the term "virtual machine" generally refers to any operating system environment that is abstracted from computing hardware by a virtual machine manager (e.g., a hypervisor). Additionally or alternatively, the modules and/or data described herein may reside and/or execute within a virtualization layer. As used herein, the term "virtualization layer" generally refers to any data layer and/or application layer that overlays and/or is abstracted from an operating system environment. A virtualization layer may be managed by a software virtualization solution (e.g., a file system filter) that presents the virtualization layer as though it were part of an underlying base operating system. For example, a software virtualization solution may redirect calls that are initially directed to locations within a base file system and/or registry to locations within a virtualization layer.

In some examples, all or a portion of example system 100 in FIG. 1A may represent portions of a mobile computing environment. Mobile computing environments may be implemented by a wide range of mobile computing devices, including mobile phones, tablet computers, e-book readers, personal digital assistants, wearable computing devices (e.g., computing devices with a head-mounted display, smartwatches, etc.), and the like. In some examples, mobile computing environments may have one or more distinct features, including, for example, reliance on battery power, presenting only one foreground application at any given time, remote management features, touchscreen features, location and movement data (e.g., provided by Global Positioning Systems, gyroscopes, accelerometers, etc.), restricted platforms that restrict modifications to system-level configurations and/or that limit the ability of third-party software to inspect the behavior of other applications, controls to restrict the installation of applications (e.g., to only originate from approved application stores), etc. Various functions described herein may be provided for a mobile computing environment and/or may interact with a mobile computing environment.

In addition, all or a portion of example system 100 in FIG. 1A may represent portions of, interact with, consume data produced by, and/or produce data consumed by one or more systems for information management. As used herein, the term "information management" may refer to the protection, organization, and/or storage of data. Examples of systems for information management may include, without limitation, storage systems, backup systems, archival systems, replication systems, high availability systems, data search systems, virtualization systems, and the like.

In some embodiments, all or a portion of example system 100 in FIG. 1A may represent portions of, produce data protected by, and/or communicate with one or more systems for information security. As used herein, the term "information security" may refer to the control of access to protected data. Examples of systems for information security may include, without limitation, systems providing managed security services, data loss prevention systems, identity authentication systems, access control systems, encryption systems, policy compliance systems, intrusion detection and prevention systems, electronic discovery systems, and the like.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations, or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

The processor as disclosed herein can be configured with instructions to perform any one or more steps of any method as disclosed herein.

It will be understood that although the terms "first," "second," "third," etc. may be used herein to describe various layers, elements, components, regions, or sections without referring to any particular order or sequence of events. These terms are merely used to distinguish one layer, element, component, region or section from another layer, element, component, region, or section. A first layer, element, component, region, or section as described herein could be referred to as a second layer, element, component, region, or section without departing from the teachings of the present disclosure.

As used herein, the term "or" is used inclusively to refer items in the alternative and in combination.

As used herein, characters such as numerals refer to like elements.

The present disclosure includes the following numbered clauses:

Clause 1. A method of assessing an image quality of a dental image, the method comprising: receiving a first dental image; cropping the first dental image; generating a score of overall image quality for the cropped first dental image using a trained neural network, wherein the trained neural network is trained using a plurality or ranked sub-sets of dental images and a loss function configured to preserve a relative ranking order of the ranked sub-sets of dental images, further wherein the sub-sets of dental images are ranked based on perceived overall image quality; and outputting an indicator of the score of overall image quality.

Clause 2. The method of clause 1, wherein the first dental image is un-resized when generating the overall image quality score.

Clause 3. The method of clause 1, further comprising masking the cropped first dental image to mask out regions that do not correspond to teeth or teeth and gingiva prior to generating the score of overall image quality.

Clause 4. The method of clause 3, wherein generating the score of overall image quality for the cropped and masked first dental image comprising using the trained neural network, wherein the trained neural network is trained using a plurality of ranked sub-sets of dental images that are masked to mask out regions that do not correspond to teeth or teeth and gingiva.

Clause 5. The method of clause 1, wherein the indicator of the score of overall image quality is configured to indicate that the overall image quality is sufficient for use with dental treatment planning.

Clause 6. The method of clause 1, wherein outputting the indicator of the score of overall image quality comprises providing feedback to a user of an assessed overall image quality.

Clause 7. The method of clause 5, wherein the first dental image is captured with a camera of a tablet computer, a cell phone, or a laptop computer.

Clause 8. The method of clause 1, wherein generating the score of overall image quality is performed on a local processor.

Clause 9. The method of clause 8, wherein the local processor is one of: a processor of a cell phone, a processor of a tablet, or a processor of a laptop computer.

Clause 10. The method of clause 1, wherein receiving the first dental image comprises receiving the first dental image from a cloud-based data storage device.

Clause 11. The method of clause 1, further comprising calculating the indicator of the score of overall image quality by applying a threshold to the score of overall image quality.

Clause 12. The method of clause 10, wherein the threshold indicates good or poor overall image quality.

Clause 13. The method of clause 1, wherein the first dental image is a digital photographic image.

Clause 14. The method of clause 1, wherein the first dental image is one of: an x-ray image, a panoramic dental scan image, a video image, a stitched image based on two or more individual images, or a combination thereof.

Clause 15. The method of clause 1, wherein outputting the indicator of the score of overall image quality comprises indicating that a new dental image should be captured.

Clause 16. The method of clause 1, wherein outputting the indicator of the score of overall image quality comprises providing a link to a video showing how to capture quality dental images.

Clause 17. The method of clause 1, wherein outputting the indicator of the score of overall image quality comprises displaying, in a browser window, the score of overall image quality.

Clause 18. The method of clause 1, wherein the trained neural network is trained using ranked sub-sets of dental images comprising ranked pairs of dental images.

Clause 19. The method of clause 1, wherein perceived overall image quality includes one or more of: perceived image darkness, perceived image blurriness, focus, inclusion of shadows, or a combination thereof.

Clause 20. The method of clause 2, wherein the masking is based on a neural network trained to identify teeth within each of the dental images.

Clause 21. The method of clause 1, wherein the trained neural network is a convolutional neural network.

Clause 22. A method of assessing an image quality of a dental image, the method comprising: receiving a first dental image; cropping the first dental image; masking the cropped first dental image to mask out regions that do not correspond to teeth or teeth and gingiva; generating a score of overall image quality for the cropped and masked first dental image using a trained neural network, wherein the trained neural network is trained using a plurality or ranked sub-sets of dental images and a loss function configured to preserve a relative ranking order of the ranked sub-sets of dental images, further wherein the sub-sets of dental images are ranked based on perceived overall image quality, wherein the plurality or ranked sub-sets of dental images are masked to mask out regions that do not correspond to teeth or teeth and gingiva; and outputting an indicator of the score of overall image quality.

Clause 23. An apparatus for assessing an image quality of a dental image, the apparatus comprising: one or more processors; and a memory storing instructions that, when executed by the one or more processors, causes the one or more processor to perform a method comprising: receiving a first dental image; cropping the first dental image; generating a score of overall image quality for the cropped first dental image using a trained neural network, wherein the trained neural network is trained using a plurality or ranked sub-sets of dental images and a loss function configured to preserve a relative ranking order of the ranked sub-sets of dental images, further wherein the sub-sets of dental images are ranked based on perceived overall image quality; and outputting an indicator of the score of overall image quality.

Clause 24. The apparatus of clause 23, wherein the first dental image is un-resized when generating the overall image quality score.

Clause 25. The apparatus of clause 23, further comprising masking the cropped first dental image to mask out regions that do not correspond to teeth or teeth and gingiva prior to generating the score of overall image quality.

Clause 26. The apparatus of clause 25, wherein generating the score of overall image quality for the cropped and masked first dental image comprising using the trained neural network, wherein the trained neural network is trained using a plurality of ranked sub-sets of dental images that are masked to mask out regions that do not correspond to teeth or teeth and gingiva.

Clause 27. The apparatus of clause 23, wherein the indicator of the score of overall image quality is configured to indicate that the overall image quality is sufficient for use with a dental treatment plan.

Clause 28. The apparatus of clause 23, wherein outputting the indicator of the score of overall image quality comprises providing feedback to a user of an assessed overall image quality.

Clause 29. The apparatus of clause 28, wherein the first dental image is captured with a camera of a tablet computer, a cell phone, or a laptop computer.

Clause 30. The apparatus of clause 29, wherein generating the score of overall image quality is performed on a local processor.

Clause 31. The apparatus of clause 30, wherein the local processor is one of: a processor of a cell phone, a processor of a tablet, or a processor of a laptop computer.

Clause 32. The apparatus of clause 23, wherein receiving the first dental image comprises receiving the first dental image from a cloud-based data storage device.

Clause 33. The apparatus of clause 23, wherein the processor further configured to calculate the indicator of the score of overall image quality by applying a threshold to the score of overall image quality.

Clause The apparatus of clause 33, wherein the threshold indicates good or poor overall image quality.

Clause 35. The apparatus of clause 23, wherein the first dental image is a digital photographic image.

Clause 36. The apparatus of clause 23, wherein the first dental image is one of: an x-ray image, a panoramic dental scan image, a video image, a stitched image based on two or more individual images, or a combination thereof.

Clause 37. The apparatus of clause 23, wherein outputting the indicator of the score of overall image quality comprises indicating that a new dental image should be captured.

Clause 38. The apparatus of clause 23, wherein outputting the indicator of the score of overall image quality comprises providing a link to a video showing how to capture quality dental images.

Clause 39. The apparatus of clause 23, wherein outputting the indicator of the score of overall image quality comprises displaying, in a browser window, the score of overall image quality.

Clause 40. The apparatus of clause 23, wherein the trained neural network is trained using ranked sub-sets of dental images comprising ranked pairs of dental images.

Clause 41. The apparatus of clause 23, wherein perceived overall image quality includes one or more of:

perceived image darkness, perceived image blurriness, focus, inclusion of shadows, or a combination thereof.

Clause 42. The apparatus of clause 24, wherein the masking is based on a neural network trained to identify teeth within each of the dental images.

Clause 43. The apparatus of clause 23, wherein the trained neural network is a convolutional neural network.

Clause 44. A computer-implemented method comprising: determining, using a camera, whether a dental imaging assistive device is present for capturing a plurality of clinically relevant photos of a person's dentition satisfying clinically acceptable criteria, the clinically acceptable criteria including at least a plurality of clinically acceptable positions and a plurality of clinically acceptable orientations of teeth relative to the camera; determining a photo capture mode based on a state of the dental imaging assistive device; determining, based on the photo capture mode, one or more photo parameters to define the clinically acceptable criteria; providing, in response to the one or more photo parameters, automated instructions for capturing the plurality of clinically relevant photos; preprocessing preliminary photos from the camera in response to the automated instructions; and capturing, using the camera based on the preprocessed preliminary photos, the plurality of clinically relevant photos.

Clause 45. The method of clause 44, wherein the state of the dental imaging assistive device comprises a presence of the dental imaging assistive device or an absence of the dental imaging assistive device.

Clause 46. The method of clause 45, wherein the dental imaging assistive device corresponds to a photo tube device, the photo tube device including a first end configured to couple an electronic device including the camera and a second end configured to engage with a patient's anatomy.

Clause 47. The method of clause 44, wherein the state of the dental imaging assistive device comprises an identity of a type of dental imaging assistive device that is determined to be present, wherein the dental imaging assistive device comprises a cheek retractor or a photo tube.

Clause 48. The method of clause 47, wherein determining a photo capture mode based on a state of the dental imaging assistive device comprises: capturing an initial photo; and identifying the dental imaging assistive device in the initial photo.

Clause 49. The method of clause 46, wherein determining a photo capture mode based on a state of the dental imaging assistive device further comprises receiving a user indication of the photo tube device.

Clause 50. The method of clause 49, wherein preprocessing the preliminary photos comprises cropping the dental imaging assistive device from the preliminary photos.

Clause 51. The method of clause 44, wherein the dental imaging assistive device corresponds to a cheek retractor.

Clause 52. The method of clause 51, wherein determining a photo capture mode based on a state of the dental imaging assistive device comprises: capturing an initial photo; and identifying the cheek retractor in the initial photo.

Clause 53. The method of clause 51, wherein determining a photo capture mode based on a state of the dental imaging assistive device further comprises receiving a user indication of the cheek retractor.

Clause 54. The method of clause 44, wherein determining a photo capture mode based on a state of the dental imaging assistive device comprises detecting an absence of the dental imaging assistive device.

Clause 55. The method of clause 54, wherein detecting the absence of the dental imaging assistive device comprises: capturing an initial photo; and identifying no assistive device in the initial photo.

Clause 56. The method of clause 54, wherein detecting the absence of the dental imaging assistive device comprises receiving a user indication of no assistive device.

Clause 57. The method of clause 44, wherein determining the photo capture mode is further based on detecting an assisted mode.

Clause 58. The method of clause 57, wherein detecting the assisted mode comprises: capturing a front initial photo with a front camera and a back initial photo with a back camera; and detecting a first person in the front initial photo and a second person in the back initial photo.

Clause 59. The method of clause 57, wherein detecting the assisted mode comprises receiving a user indication of the assisted mode.

Clause 60. The method of clause 44, wherein preprocessing the preliminary photos comprises detecting a face in the preliminary photos.

Clause 61. The method of clause 44, wherein preprocessing the preliminary photos comprises detecting a facial landmark in the preliminary photos.

Clause 62. The method of clause 61, wherein the facial landmark corresponds to a mouth and preprocessing the preliminary photos further comprises cropping around the detected mouth in the preliminary photos.

Clause 63. The method of clause 44, wherein preprocessing the preliminary photos comprises resizing the preliminary photos.

Clause 64. The method of clause 44, wherein preprocessing the preliminary photos comprises padding the preliminary photos.

Clause 65. The method of clause 64, wherein the padding changes an aspect ratio of the photo to a 2:1 aspect ratio.

Clause 66. The method of clause 44, wherein the camera is one of a plurality of selectable cameras, and wherein the method further comprises selecting, based on the determined photo capture mode, the camera for capturing the plurality of clinically relevant photos.

Clause 67. The method of clause 78, wherein the plurality of selectable cameras comprises a front camera and a back camera of a mobile device.

Clause 68. The method of clause 44, wherein providing the automated instructions comprises mirroring the automated instructions for display.

Clause 69. The method of clause 44, further comprising determining, based on the photo capture mode, a capture order for capturing the plurality of clinically relevant photos.

Clause 70. The method of clause 69, wherein the capture order comprises a right view, a center view, and a left view.

Clause 71. The method of clause 69, wherein the capture order comprises a center view, a right view, and a left view.

Clause 72. The method of clause 69, wherein the automated instructions include instructions for the capture order.

Clause 73. The method of clause 44, wherein preprocessing the preliminary photos comprises detecting whether the preliminary photos satisfy the one or more photo parameters.

Clause 74. The method of clause 73, wherein capturing the plurality of clinically relevant photos further comprises capturing, using the preprocessed preliminary photos in response to satisfying the clinically acceptable criteria, the plurality of clinically relevant photos.

Clause 75. A system comprising: one or more processors; a camera; and memory storing computer program instructions that, when executed by the one or more processors, causes the system to perform a method comprising: determining, using a camera, whether a dental imaging assistive device is present for capturing a plurality of clinically relevant photos of a person's dentition satisfying clinically acceptable criteria, the clinically acceptable criteria including at least a plurality of clinically acceptable positions and a plurality of clinically acceptable orientations of teeth relative to the camera; determining a photo capture mode based on a state of the dental imaging assistive device; determining, based on the photo capture mode, one or more photo parameters to define the clinically acceptable criteria; providing, in response to the one or more photo parameters, automated instructions for capturing the plurality of clinically relevant photos; preprocessing preliminary photos from the camera in response to the automated instructions; and capturing, using the camera based on the preprocessed preliminary photos, the plurality of clinically relevant photos.

Clause 76. The system of clause 75, further comprising a mobile device, wherein the mobile device includes the one or more processors, the camera, and the memory.

Clause 77. The system of clause 75, wherein the state of the dental imaging assistive device comprises a presence of the dental imaging assistive device or an absence of the dental imaging assistive device.

Clause 78. The system of clause 77, wherein the dental imaging assistive device corresponds to a photo tube device, the photo tube device including a first end configured to couple an electronic device including the camera and a second end configured to engage with a patient's anatomy.

Clause 79. The system of clause 78, wherein determining a photo capture mode based on a state of the dental imaging assistive device comprises: capturing an initial photo; and identifying the photo tube device in the initial photo.

Clause 80. The system of clause 78, wherein determining a photo capture mode based on a state of the dental imaging assistive device further comprises receiving a user indication of the photo tube device.

Clause 81. The system of clause 78, wherein preprocessing the preliminary photos comprises cropping the photo tube device from the preliminary photos.

Clause 82. The system of clause 75, wherein the dental imaging assistive device corresponds to a cheek retractor.

Clause 83. The system of clause 82, wherein determining a photo capture mode based on a state of the dental imaging assistive device comprises: capturing an initial photo; and identifying the cheek retractor in the initial photo.

Clause 84. The system of clause 82, wherein determining a photo capture mode based on a state of the dental imaging assistive device further comprises receiving a user indication of the cheek retractor.

Clause 85. The system of clause 75, wherein determining a photo capture mode based on a state of the dental imaging assistive device comprises detecting an absence of the dental imaging assistive device.

Clause 86. The system of clause 85, wherein detecting the absence of the dental imaging assistive device comprises: capturing an initial photo; and identifying no assistive device in the initial photo.

Clause 87. The system of clause 85, wherein detecting the absence of the dental imaging assistive device comprises receiving a user indication of no assistive device.

Clause 88. The system of clause 75, wherein determining the photo capture mode is further based on detecting an assisted mode.

Clause 89. The system of clause 88, wherein detecting the assisted mode comprises:
capturing a front initial photo with a front camera and a back initial photo with a back camera; and
detecting a first person in the front initial photo and a second person in the back initial photo.

Clause 90. The system of clause 88, wherein detecting the assisted mode comprises receiving a user indication of the assisted mode.

Clause 91. The system of clause 75, wherein preprocessing the preliminary photos comprises detecting a face in the preliminary photos.

Clause 92. The system of clause 75, wherein preprocessing the preliminary photos comprises detecting a facial landmark in the preliminary photos.

Clause 93. The system of clause 92, wherein the facial landmark corresponds to a mouth and preprocessing the preliminary photos further comprises cropping around the detected mouth in the preliminary photos.

Clause 94. The system of clause 75, wherein preprocessing the preliminary photos comprises resizing the preliminary photos.

Clause 95. The system of clause 75, wherein preprocessing the preliminary photos comprises padding the preliminary photos.

Clause 96. The system of clause 95, wherein the padding changes an aspect ratio of the photo to a 2:1 aspect ratio.

Clause 97. The system of clause 75, wherein the photo capture mode designates a front camera as the camera for capturing the plurality of clinically relevant photos.

Clause 98. The system of clause 75, wherein the photo capture mode designates a back camera as the camera for capturing the plurality of clinically relevant photos.

Clause 99. The system of clause 75, wherein providing the automated instructions comprises mirroring the automated instructions for display.

Clause 100. The system of clause 75, wherein the photo capture mode designates a capture order.

Clause 101. The system of clause 100, wherein the capture order comprises a right view, a center view, and a left view.

Clause 102. The system of clause 100, wherein the capture order comprises a center view, a right view, and a left view.

Clause 103. The system of clause 100, wherein the automated instructions include instructions for the capture order.

Clause 104. The system of clause 75, wherein preprocessing the preliminary photos comprises detecting whether the preliminary photos satisfy the one or more photo parameters.

Clause 105. The system of clause 104, wherein capturing the plurality of clinically relevant photos further comprises capturing, using the preprocessed preliminary photos in response to satisfying the clinically acceptable criteria, the plurality of clinically relevant photos.

Clause 106. A non-transitory computer-readable storage medium storing instructions that, when executed by one or more processors of a device, cause the one or more processors to perform the method of any one of clauses 1-22 and 44-74.

Embodiments of the present disclosure have been shown and described as set forth herein and are provided by way of example only. One of ordinary skill in the art will recognize numerous adaptations, changes, variations, and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A computer-implemented method comprising:

determining, using a camera, whether a dental imaging assistive device is present for capturing a plurality of clinically relevant photos of a person's dentition satisfying clinically acceptable criteria, the clinically acceptable criteria including at least a plurality of clinically acceptable positions and a plurality of clinically acceptable orientations of teeth relative to the camera;

determining a photo capture mode based on a state of the dental imaging assistive device, wherein the state of the dental imaging assistive device comprises a presence of the dental imaging assistive device or an absence of the dental imaging assistive device, and the dental imaging assistive device corresponds to a photo tube device, the photo tube device including a first end configured to couple an electronic device including the camera and a second end configured to engage with a patient's anatomy;

determining, based on the photo capture mode, one or more photo parameters to define the clinically acceptable criteria;

providing, in response to the one or more photo parameters, automated instructions for capturing the plurality of clinically relevant photos;

preprocessing preliminary photos from the camera in response to the automated instructions; and capturing, using the camera based on the preprocessed preliminary photos, the plurality of clinically relevant photos.

2. The method of claim 1, wherein the state of the dental imaging assistive device comprises an identity of a type of dental imaging assistive device that is determined to be present.

3. The method of claim 2, wherein determining a photo capture mode based on a state of the dental imaging assistive device comprises:

capturing an initial photo; and identifying the dental imaging assistive device in the initial photo.

4. A computer-implemented method comprising:

determining, using a camera, whether a dental imaging assistive device is present for capturing a plurality of clinically relevant photos of a person's dentition satisfying clinically acceptable criteria, the clinically acceptable criteria including at least a plurality of clinically acceptable positions and a plurality of clinically acceptable orientations of teeth relative to the camera;

determining a photo capture mode based on a state of the dental imaging assistive device, wherein determining a photo capture mode based on a state of the dental imaging assistive device comprises detecting an absence of the dental imaging assistive device, and wherein detecting the absence of the dental imaging assistive device comprises:

capturing an initial photo; and identifying no assistive device in the initial photo;

determining, based on the photo capture mode, one or more photo parameters to define the clinically acceptable criteria;

providing, in response to the one or more photo parameters, automated instructions for capturing the plurality of clinically relevant photos;

preprocessing preliminary photos from the camera in response to the automated instructions; and capturing, using the camera based on the preprocessed preliminary photos, the plurality of clinically relevant photos.

5. The method of claim 1, wherein determining the photo capture mode is further based on detecting an assisted mode, wherein detecting the assisted mode comprises:

capturing a front initial photo with a front camera and a back initial photo with a back camera; and detecting a first person in the front initial photo and a second person in the back initial photo.

6. A computer-implemented method comprising:

determining, using a camera, whether a dental imaging assistive device is present for capturing a plurality of clinically relevant photos of a person's dentition satisfying clinically acceptable criteria, the clinically acceptable criteria including at least a plurality of clinically acceptable positions and a plurality of clinically acceptable orientations of teeth relative to the camera;

determining a photo capture mode based on a state of the dental imaging assistive device;

determining, based on the photo capture mode, one or more photo parameters to define the clinically acceptable criteria;

providing, in response to the one or more photo parameters, automated instructions for capturing the plurality of clinically relevant photos;

preprocessing preliminary photos from the camera in response to the automated instructions, wherein preprocessing the preliminary photos comprises detecting a facial landmark in the preliminary photos, wherein the facial landmark corresponds to a mouth and preprocessing the preliminary photos further comprises cropping around the detected mouth in the preliminary photos; and capturing, using the camera based on the preprocessed preliminary photos, the plurality of clinically relevant photos.

7. The method of claim 1, wherein the camera is one of a plurality of selectable cameras, and wherein the method further comprises selecting, based on the determined photo capture mode, the camera for capturing the plurality of clinically relevant photos.

8. The method of claim 7, wherein the plurality of selectable cameras comprises a front camera and a back camera of a mobile device.

9. The method of claim 1, further comprising determining, based on the photo capture mode, a capture order for capturing the plurality of clinically relevant photos.

10. A system comprising:

one or more processors;

a camera; and memory storing computer program instructions that, when executed by the one or more processors, causes the system to perform a method comprising:

determining, using a camera, whether a dental imaging assistive device is present for capturing a plurality of clinically relevant photos of a person's dentition satisfying clinically acceptable criteria, the clinically acceptable criteria including at least a plurality of clinically acceptable positions and a plurality of clinically acceptable orientations of teeth relative to the camera;

determining a photo capture mode based on a state of the dental imaging assistive device, wherein the dental imaging assistive device corresponds to a photo tube device, the photo tube device including a first end configured to couple an electronic device including the camera and a second end configured to engage with a patient's anatomy;

determining, based on the photo capture mode, one or more photo parameters to define the clinically acceptable criteria;

providing, in response to the one or more photo parameters, automated instructions for capturing the plurality of clinically relevant photos;

preprocessing preliminary photos from the camera in response to the automated instructions; and capturing, using the camera based on the preprocessed preliminary photos, the plurality of clinically relevant photos.

11. The system of claim 10, further comprising a mobile device, wherein the mobile device includes the one or more processors, the camera, and the memory.

12. The system of claim 10, wherein the state of the dental imaging assistive device comprises a presence of the dental imaging assistive device or an absence of the dental imaging assistive device.

13. The system of claim 10, wherein the state of the dental imaging assistive device comprises an identity of a type of dental imaging assistive device that is determined to be present.

14. The system of claim 10, wherein determining a photo capture mode based on a state of the dental imaging assistive device comprises:

capturing an initial photo; and identifying the dental imaging assistive device in the initial photo.

15. A system comprising:

one or more processors;

a camera; and memory storing computer program instructions that, when executed by the one or more processors, causes the system to perform a method comprising:

determining, using a camera, whether a dental imaging assistive device is present for capturing a plurality of clinically relevant photos of a person's dentition satisfying clinically acceptable criteria, the clinically acceptable criteria including at least a plurality of clinically acceptable positions and a plurality of clinically acceptable orientations of teeth relative to the camera;

determining a photo capture mode based on a state of the dental imaging assistive device, wherein determining a photo capture mode based on a state of the dental imaging assistive device comprises detecting an absence of the dental imaging assistive device, wherein detecting the absence of the dental imaging assistive device comprises:

capturing an initial photo; and identifying no assistive device in the initial photo;

determining, based on the photo capture mode, one or more photo parameters to define the clinically acceptable criteria;

providing, in response to the one or more photo parameters, automated instructions for capturing the plurality of clinically relevant photos;

preprocessing preliminary photos from the camera in response to the automated instructions; and capturing, using the camera based on the preprocessed preliminary photos, the plurality of clinically relevant photos.

16. The system of claim 10, wherein determining the photo capture mode is further based on detecting an assisted mode.

17. The system of claim 16, wherein detecting the assisted mode comprises:

capturing a front initial photo with a front camera and a back initial photo with a back camera; and detecting a first person in the front initial photo and a second person in the back initial photo.

18. A system comprising:

one or more processors;

a camera; and memory storing computer program instructions that, when executed by the one or more processors, causes the system to perform a method comprising:

determining, using a camera, whether a dental imaging assistive device is present for capturing a plurality of clinically relevant photos of a person's dentition satisfying clinically acceptable criteria, the clinically acceptable criteria including at least a plurality of clinically acceptable positions and a plurality of clinically acceptable orientations of teeth relative to the camera;

determining a photo capture mode based on a state of the dental imaging assistive device;

determining, based on the photo capture mode, one or more photo parameters to define the clinically acceptable criteria;

providing, in response to the one or more photo parameters, automated instructions for capturing the plurality of clinically relevant photos;

preprocessing preliminary photos from the camera in response to the automated instructions, wherein preprocessing the preliminary photos comprises detecting a facial landmark in the preliminary photos, wherein the facial landmark corresponds to a mouth and preprocessing the preliminary photos further comprises cropping around the detected mouth in the preliminary photos; and capturing, using the camera based on the preprocessed preliminary photos, the plurality of clinically relevant photos.

19. A system comprising:

one or more processors;

a plurality of selectable cameras; and memory storing computer program instructions that, when executed by the one or more processors, causes the system to perform a method comprising:

determining, using at least one of the plurality of cameras, whether a dental imaging assistive device is present for capturing a plurality of clinically relevant photos of a person's dentition satisfying clinically acceptable criteria, the clinically acceptable criteria including at least a plurality of clinically acceptable positions and a plurality of clinically acceptable orientations of teeth relative to the cameras;

determining a photo capture mode based on a state of the dental imaging assistive device;

selecting, based on the determined photo capture mode, a first camera of the plurality of cameras for capturing the plurality of clinically relevant photos;

determining, based on the photo capture mode, one or more photo parameters to define the clinically acceptable criteria;

providing, in response to the one or more photo parameters, automated instructions for capturing the plurality of clinically relevant photos;

preprocessing preliminary photos from the first camera in response to the automated instructions; and capturing, using the first camera based on the preprocessed preliminary photos, the plurality of clinically relevant photos.

20. The system of claim 19, wherein plurality of selectable cameras comprises a front camera and a back camera of a mobile device.

21. The system of claim 10, wherein the method further comprises determining, based on the photo capture mode, a capture order for capturing the plurality of clinically relevant photos.

22. The method of claim 1, wherein preprocessing the preliminary photos comprises detecting whether the preliminary photos satisfy the one or more photo parameters.

23. The system of claim 15, wherein preprocessing the preliminary photos comprises detecting whether the preliminary photos satisfy the one or more photo parameters.

24. The method of claim 1, wherein providing the automated instructions comprises providing automated instructions for display.

25. The method of claim 1, wherein providing the automated instructions comprises providing mirrored automated instructions for display to be viewed in a mirror.

* * * * *